United States Patent
Lennox et al.

(10) Patent No.: US 8,454,671 B2
(45) Date of Patent: *Jun. 4, 2013

(54) METHOD AND APPARATUS FOR REDUCING BODY TEMPERATURE OF A SUBJECT

(75) Inventors: Charles D. Lennox, Hudson, NH (US); Steven M. Johnson, Westford, MA (US); Susan Beinor, Sutton, MA (US); Maria Benson, West Boylston, MA (US); Don Paul Nogueira, Salem, MA (US); John W. Carroll, Pepperell, MA (US); Helen Maslocka, Watertown, MA (US)

(73) Assignee: MedCool, Inc., Wellesley, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/623,823

(22) Filed: Nov. 23, 2009

(65) Prior Publication Data
US 2010/0137951 A1     Jun. 3, 2010

Related U.S. Application Data

(63) Continuation of application No. 11/284,114, filed on Nov. 21, 2005, now Pat. No. 7,621,945, which is a continuation of application No. 10/706,327, filed on Nov. 12, 2003, now Pat. No. 7,052,509.

(60) Provisional application No. 60/432,884, filed on Dec. 12, 2002.

(51) Int. Cl.
*A61F 7/02* (2006.01)

(52) U.S. Cl.
USPC .................................... 607/104; 607/108

(58) Field of Classification Search
USPC .............. 34/96, 97, 99; 607/96–114
See application file for complete search history.

(56) References Cited

U.S. PATENT DOCUMENTS

| 26,663 A | 1/1860 | French |
|---|---|---|
| 998,804 A | 7/1911 | Salisbury |

(Continued)

FOREIGN PATENT DOCUMENTS

| JP | 05220186 | 8/1993 |
|---|---|---|
| JP | 05220187 | 8/1993 |

(Continued)

OTHER PUBLICATIONS

Hachimi-Idrissi et al., "Mild Hypothermia Induced by a Helmet Device: A Clinical Feasibility Study," Resuscitation 51:275-281 (2001).

(Continued)

*Primary Examiner* — Aaron Roane
(74) *Attorney, Agent, or Firm* — Thomas J. Engellenner; Pepper Hamilton LLP

(57) ABSTRACT

A cooling system includes a console and a tissue cooling device such as a head-cooling device. An operator applies the head-cooling device to the head of a patient at risk for ischemic injury. The console provides a cooling fluid to a fluid circulation space located between the cooling device and the patient's head under a positive gage pressure. Direct contact between the cooling fluid and the patient's head provides a relatively rapid induction of systemic hypothermia in the patient, thereby minimizing or preventing ischemic injury in the patient. The console also removes air from a channel disposed about an inner rim of the cooling device, using a negative gage pressure. Such removal of the air from the channel seals the rim of the cooling device to the head of the patient, including portions of the channel in contact with hair of the patient's head, and minimizes leaking of the cooling fluid beyond the rim of the cooling device.

21 Claims, 34 Drawing Sheets

U.S. PATENT DOCUMENTS

| | | |
|---|---|---|
| 2,043,721 A | 6/1936 | Warwick |
| 2,224,876 A | 12/1940 | Matys |
| 2,255,751 A | 9/1941 | Bancel |
| 2,272,481 A | 2/1942 | Rinkes et al. |
| 2,416,788 A | 3/1947 | Andrews |
| 2,512,990 A | 6/1950 | Akerman |
| 2,540,547 A | 2/1951 | Rodert |
| 2,566,600 A | 9/1951 | Colon |
| 2,706,988 A | 4/1955 | Weber |
| 3,085,405 A | 4/1963 | Frantti |
| 3,153,720 A | 10/1964 | Petronio et al. |
| 3,229,681 A | 1/1966 | Gluckstein |
| 3,348,236 A | 10/1967 | Copeland |
| 3,378,004 A | 4/1968 | Claycomb et al. |
| 3,449,761 A | 6/1969 | Long |
| 3,477,424 A | 11/1969 | Tracy |
| 3,548,827 A * | 12/1970 | Abel .............................. 604/318 |
| 3,587,577 A | 6/1971 | Solyanka et al. |
| 3,610,323 A | 10/1971 | Troyer |
| 3,648,289 A | 3/1972 | Moreland |
| 3,738,367 A | 6/1973 | Hardy |
| 3,786,809 A | 1/1974 | Kitrilakis |
| 3,839,621 A | 10/1974 | Hariu |
| 3,892,225 A | 7/1975 | Twose |
| 3,905,367 A | 9/1975 | Dapcich |
| 3,908,655 A | 9/1975 | Lund |
| 3,946,498 A | 3/1976 | Waters et al. |
| 4,067,064 A | 1/1978 | Cerniway et al. |
| 4,074,369 A | 2/1978 | Harmon |
| 4,108,146 A | 8/1978 | Golden |
| 4,114,620 A | 9/1978 | Moore et al. |
| 4,139,004 A | 2/1979 | Gonzalez, Jr. |
| 4,149,529 A | 4/1979 | Copeland et al. |
| 4,149,541 A | 4/1979 | Gammons et al. |
| 4,167,932 A | 9/1979 | Zebuhr |
| 4,172,495 A | 10/1979 | Zebuhr et al. |
| 4,194,247 A | 3/1980 | Melander |
| 4,224,941 A | 9/1980 | Stivala |
| 4,237,877 A | 12/1980 | Boehler |
| 4,286,439 A | 9/1981 | Pasternack |
| 4,294,225 A | 10/1981 | Mayo |
| 4,353,359 A | 10/1982 | Milbauer |
| 4,390,997 A | 7/1983 | Hinz et al. |
| 4,398,535 A | 8/1983 | Guibert |
| 4,418,745 A | 12/1983 | Roehr |
| 4,425,916 A | 1/1984 | Bowen |
| 4,523,594 A | 6/1985 | Kuznetz |
| 4,566,455 A | 1/1986 | Kramer |
| 4,572,188 A | 2/1986 | Augustine et al. |
| 4,575,097 A | 3/1986 | Brannigan et al. |
| 4,691,762 A | 9/1987 | Elkins et al. |
| 4,738,119 A | 4/1988 | Zafred |
| 4,747,408 A | 5/1988 | Chuan-Chih |
| 4,753,242 A | 6/1988 | Saggers |
| 4,770,169 A | 9/1988 | Schmoegner et al. |
| 4,781,193 A | 11/1988 | Pagden |
| 4,844,072 A | 7/1989 | French et al. |
| 4,869,250 A | 9/1989 | Bitterly |
| 4,886,063 A | 12/1989 | Crews |
| 4,920,963 A | 5/1990 | Brader |
| 4,969,880 A | 11/1990 | Zamierowski |
| 4,987,618 A | 1/1991 | Tolbert |
| 4,998,415 A | 3/1991 | Larsen |
| 5,062,424 A | 11/1991 | Hooker |
| 5,097,829 A | 3/1992 | Quisenberry |
| 5,100,261 A | 3/1992 | Plemon |
| 5,167,227 A | 12/1992 | Meserlian |
| 5,168,576 A | 12/1992 | Krent et al. |
| 5,174,285 A | 12/1992 | Fontenot |
| 5,230,335 A | 7/1993 | Johnson, Jr. et al. |
| 5,235,709 A | 8/1993 | Terlep |
| 5,241,951 A | 9/1993 | Mason et al. |
| 5,251,938 A * | 10/1993 | Erickson ........................... 285/5 |
| 5,261,399 A * | 11/1993 | Klatz et al. .................... 607/104 |
| 5,269,369 A | 12/1993 | Faghri |
| 5,292,347 A | 3/1994 | Pompei |
| 5,300,105 A | 4/1994 | Owens |
| D347,491 S | 5/1994 | Holloway |
| 5,314,455 A | 5/1994 | Johnson, Jr. et al. |
| 5,330,519 A | 7/1994 | Mason et al. |
| 5,342,411 A | 8/1994 | Maxted et al. |
| 5,383,918 A | 1/1995 | Panetta |
| 5,383,919 A | 1/1995 | Kelly et al. |
| 5,411,493 A | 5/1995 | Rodriguez |
| 5,415,222 A | 5/1995 | Colvin et al. |
| 5,417,720 A | 5/1995 | Mason |
| 5,423,087 A | 6/1995 | Krent et al. |
| 5,429,534 A | 7/1995 | Cano |
| 5,438,707 A | 8/1995 | Horn |
| 5,449,379 A | 9/1995 | Hadtke |
| 5,456,701 A | 10/1995 | Stout |
| 5,470,353 A | 11/1995 | Jensen |
| 5,486,206 A | 1/1996 | Avery |
| 5,486,207 A | 1/1996 | Mahawili |
| 5,496,357 A | 3/1996 | Jensen et al. |
| 5,507,103 A | 4/1996 | Merritt |
| 5,507,792 A | 4/1996 | Mason et al. |
| 5,533,354 A | 7/1996 | Pirkle |
| 5,562,604 A | 10/1996 | Yablon et al. |
| 5,603,728 A | 2/1997 | Pachys |
| 5,609,619 A | 3/1997 | Pompei |
| 5,634,890 A | 6/1997 | Morris |
| 5,643,336 A | 7/1997 | Lopez-Claros |
| 5,683,438 A | 11/1997 | Grahn |
| 5,697,920 A | 12/1997 | Gibbons |
| 5,792,216 A | 8/1998 | Kappel |
| 5,800,483 A | 9/1998 | Vought |
| 5,871,526 A | 2/1999 | Gibbs et al. |
| 5,913,885 A | 6/1999 | Klatz et al. |
| 5,947,914 A | 9/1999 | Augustine |
| 5,954,680 A | 9/1999 | Augustine |
| 5,960,469 A | 10/1999 | Nuckols et al. |
| 5,964,721 A | 10/1999 | Augustine |
| 5,964,723 A | 10/1999 | Augustine |
| 5,976,176 A | 11/1999 | Webb, II |
| 5,986,163 A | 11/1999 | Augustine |
| 6,030,412 A | 2/2000 | Klatz et al. |
| 6,045,518 A | 4/2000 | Augustine |
| 6,050,099 A | 4/2000 | Lopa et al. |
| 6,086,609 A * | 7/2000 | Buckley ........................ 607/104 |
| 6,109,338 A | 8/2000 | Butzer |
| 6,113,561 A | 9/2000 | Augustine |
| 6,113,626 A | 9/2000 | Clifton et al. |
| 6,117,164 A | 9/2000 | Gildersleeve et al. |
| 6,126,680 A | 10/2000 | Wass |
| 6,128,784 A | 10/2000 | Frank |
| 6,149,674 A | 11/2000 | Borders |
| 6,156,059 A | 12/2000 | Olofsson |
| 6,178,562 B1 | 1/2001 | Elkins |
| 6,197,045 B1 | 3/2001 | Carson |
| 6,210,427 B1 | 4/2001 | Augustine et al. |
| 6,213,966 B1 | 4/2001 | Augustine |
| 6,217,535 B1 | 4/2001 | Augustine |
| 6,230,501 B1 | 5/2001 | Bailey et al. |
| 6,238,427 B1 | 5/2001 | Matta |
| 6,241,697 B1 | 6/2001 | Augustine |
| 6,241,698 B1 | 6/2001 | Augustine |
| 6,241,756 B1 | 6/2001 | Kappel |
| 6,245,094 B1 | 6/2001 | Pompei |
| 6,245,096 B1 | 6/2001 | Tomic-Edgar et al. |
| 6,264,622 B1 | 7/2001 | Augustine |
| 6,276,155 B2 | 8/2001 | Siman-Tov et al. |
| 6,277,143 B1 | 8/2001 | Klatz et al. |
| 6,312,453 B1 | 11/2001 | Stefanile et al. |
| 6,349,412 B1 | 2/2002 | Dean |
| 6,352,550 B1 | 3/2002 | Gildersleeve et al. |
| 6,371,976 B1 | 4/2002 | Vrzalik et al. |
| 6,375,673 B1 | 4/2002 | Clifton et al. |
| 6,375,674 B1 | 4/2002 | Carson |
| 6,406,447 B1 | 6/2002 | Thrash et al. |
| 6,406,448 B1 | 6/2002 | Augustine |
| 6,407,307 B1 | 6/2002 | Augustine |
| 6,419,651 B1 | 7/2002 | Augustine |
| 6,419,691 B1 | 7/2002 | Hanner |
| 6,423,018 B1 | 7/2002 | Augustine |
| 6,461,379 B1 * | 10/2002 | Carson et al. .................. 607/104 |
| 6,500,200 B1 | 12/2002 | Kushnir |

| | | |
|---|---|---|
| 6,520,982 B1 | 2/2003 | Boynton et al. |
| 6,551,347 B1 | 4/2003 | Elkins |
| 6,581,400 B2 | 6/2003 | Augustine et al. |
| 6,602,277 B2 | 8/2003 | Grahn et al. |
| 6,605,051 B2 | 8/2003 | Augustine |
| 6,620,187 B2 | 9/2003 | Carson et al. |
| 6,645,232 B2 | 11/2003 | Carson |
| 6,648,905 B2 | 11/2003 | Hoglund et al. |
| 6,656,208 B2 | 12/2003 | Grahn et al. |
| 6,660,027 B2 | 12/2003 | Gruszecki et al. |
| 6,669,715 B2 | 12/2003 | Hoglund et al. |
| 6,692,518 B2 | 2/2004 | Carson |
| 6,699,267 B2 | 3/2004 | Voorhees et al. |
| 6,799,063 B2 | 9/2004 | Carson |
| 6,802,855 B2 | 10/2004 | Ellingboe et al. |
| 6,818,012 B2 | 11/2004 | Ellingboe |
| 6,827,728 B2 | 12/2004 | Ellingboe et al. |
| 2002/0103520 A1 | 8/2002 | Latham |
| 2002/0161419 A1 | 10/2002 | Carson et al. |
| 2003/0163183 A1 | 8/2003 | Carson |

FOREIGN PATENT DOCUMENTS

| | | |
|---|---|---|
| WO | WO 82/04184 | 12/1982 |
| WO | WO 92/20309 | 11/1992 |
| WO | WO 98/16176 | 4/1998 |

OTHER PUBLICATIONS

International Search Report from Intl. Appl. No. PCT/US03/13091, mailed Dec. 4, 2003.

International Search Report from Intl. Appl. No. PCT/US03/35930, mailed Jul. 1, 2004.

International Search Report from Intl. Appl. No. PCT/US04/24937, mailed Jul. 6, 2005.

International Search Report from Intl. Appl. No. PCT/US06/1561, mailed Apr. 23, 2007.

Supplementary European Search Report, from EP Appl. No. 03 79 6381, mailed Aug. 31, 2007.

Tooley et al., Head Cooling with Mild Systemic Hypothermia in Anesthetized Piglets is Neuroprotective, Annals of Neurology 53(1):65-72 (2003).

Tooley et al., "Significant Selective Head Cooling Can Be Maintained Long-Term After Global Hypoxia Ischemia in Newborn Piglets," Pediatrics 109(4):643-649 (2002).

* cited by examiner

METHOD AND APPARATUS FOR REDUCING BODY TEMPERATURE OF A SUBJECT

RELATED APPLICATIONS

This application is a continuation of U.S. application Ser. No. 11/284,114 filed Nov. 21, 2005, which is a continuation of U.S. application Ser. No. 10/706,327 filed Nov. 12, 2003, now U.S. Pat. No. 7,052,509 issued May 30, 2006, which claims the benefit of U.S. Provisional Application Ser. No. 60/432,884, filed Dec. 12, 2002, all of these applications are hereby incorporated by reference herein.

This application is also related to U.S. application Ser. No. 10/424,391 filed Apr. 25, 2003, now U.S. Pat. No. 7,008,445 issued Mar. 7, 2006, which claims the benefit of U.S. Provisional Application Ser. No. 60/376,249 filed Apr. 29, 2002. All of these application are also hereby incorporated by reference herein.

BACKGROUND

Patients that suffer from stroke, cardiac arrest, or trauma, such as head trauma, as well as patients that have undergone invasive brain or vascular surgery, are at risk for ischemic injury. Ischemic injury occurs as a result of a lack of oxygen (e.g. lack of oxygenated blood) to an organ, such as caused by a blockage or constriction to a vessel carrying blood to the organ. For example, in the case where a patient suffers a heart attack, typically, a clot can block one of the coronary arteries that carries blood and oxygen to the patient's heart muscle. As a result of the blockage (e.g., an ischemic condition) the patient's heart can experience ischemic tissue injury or heart damage. In the case where a patient suffers from a stroke, typically, a clot blocks the blood supply to a portion of the patient's brain. The blockage, in turn, causes ischemic damage to the brain tissue. For example, as a result of the stroke, the brain experiences a critical or terminal rise in intra-cranial pressure, brain cell death, and a loss of brain function.

Induction of systemic hypothermia (e.g., a hypothermic state) in a patient may minimize ischemic injury when the patient suffers from a stroke, cardiac arrest, heart attack, trauma, or surgery. For example, in the case where the patient suffers a heart attack, the effectiveness of hypothermia is a function of the depth (e.g., within a temperature range between approximately 30° C. and 35° C. for example) and duration of the hypothermic state as applied to the heart. The effectiveness of the hypothermia is also a function of the amount of time that elapses between the original insult (e.g., heart attack) and achievement of protective levels of hypothermia. Also, for trauma and stroke patients, hypothermia aids in controlling swelling of the patient's brain. Furthermore, surgeons typically use hypothermia during brain and other invasive surgeries to protect the brain from surgical interruptions in blood flow.

Systemic hypothermia has historically been applied, such as by immersion of the patient's body in a cool bath, where the depth and duration of hypothermia is limited by the patient's ability to tolerate the therapy. Currently, there are several conventional systemic hypothermia systems available. Such conventional systems include blankets or pads where cooled water is circulated through channels in the walls of the blanket or pad and the patient's body contacts the walls of the blanket.

Attempts have been also made to induce hypothermia in a patient by local cooling the surface of the patient's head. For example, a conventional head-cooling device involves a head cap with a gel substance contained within the walls of the cap. Prior to use, for example, a user (e.g., medical technician) places the head-cooling device in a freezer to reduce the temperature of the gel within the cap. During operation, the user fits the reduced-temperature cap to the head of a patient. The gel within the walls of the cap absorbs heat from the head, thereby cooling the head of the patient.

Other conventional devices induce systemic hypothermia in a patient by providing contact between a tissue region of interest and a cooling fluid. For example, one conventional device includes a flexible hood having multiple ribs or studs disposed on the inner surface of the hood. When a user places the hood on a head of a patient, the ribs or studs contact the head and maintain a fluid circulation space between the head and the hood and an edge, defined by the hood, contacts the patient's skin. A negative pressure source draws a cooling fluid through the flexible hood, under negative pressure, to cause the fluid to contact the scalp of the patient and draw heat away from (e.g., cool) the scalp. Furthermore, application of the negative pressure seals the edges of the hood against the skin of the patient (e.g., a region substantially free of hair).

SUMMARY

Conventional techniques for providing systemic hypothermia to a patient suffer from a variety of deficiencies.

As indicated above, systemic hypothermia reduces ischemic injury from stroke, cardiac arrest, heart attack, trauma, and surgery. However, there are several drawbacks to the approaches described above. For example, application of systemic hypothermia can take several hours to lower a patient's body to therapeutic temperatures. Such a time period delays achieving therapeutic temperatures within the patient and, therefore, allows the progression of irreversible injury to the brain or heart. In another drawback to known systemic hypothermia systems, systemic hypothermia cannot be initiated until after the patient has been admitted to the hospital.

As indicated above, attempts have been made to induce systemic hypothermia by using head-cooling devices to cool the surface of the head, such as a head cap with a gel substance contained within the walls of the cap. For example, during operation, the user fits the reduced-temperature cap to the head of a patient. The gel within the walls of the cap absorbs heat from the head, thereby cooling the head of the patient. Reports from clinical trials using such devices indicate, however, that while these devices induce systemic hypothermia, such induction is performed at a relatively slow rate. A significant problem is that hair, especially dry hair, is a very effective insulator. There is significant variation from patient to patient in the thickness of hair on the head and its distribution on the head. A device that does not address the insulating effect of hair, and its variability among patients will be ineffective in rapidly inducing systemic hypothermia in a patient.

A second significant deficiency with conventional head-cooling devices relates to the separation of the cooling medium (e.g., gel or circulating water) from the head by a material forming the device. Typically, head-cooling devices are made of plastic or woven material, both of which are highly insulative and greatly reduce the amount of heat that is transferred from the head into the cooling medium.

Also as indicated above, conventional head-cooling devices include a flexible hood placed on the head of a patient. A cooling fluid is drawn through the flexible hood under negative pressure to contact the scalp of the patient and draw heat away from (e.g., cool) the patient's scalp. Because the flexible hood, however, relies on a negative pressure to draw the cooling fluid within a region between the scalp and the hood apparatus, a large number of regularly spaced ribs or studs are required to form fluid channels between the scalp and the apparatus. Furthermore, application of the negative pressure seals the edges of the hood against the skin of the tissue region. However, such sealing is ineffective when the edges are positioned over hair, such as hair protruding from a patient scalp. In the case where the edges contact the hair of a patient's scalp, the hair minimizes the seal between the hood and the patient, thereby allowing leakage of the cooling fluid from the hood apparatus.

By contrast, embodiments of the present invention significantly overcome such deficiencies and provide techniques for inducing systemic hypothermia in a patient. A cooling system includes a console and a tissue cooling device, such as a head-cooling device. An operator applies the head-cooling device to the head of a patient at risk for ischemic injury. The console provides a cooling fluid to a fluid circulation space located between the cooling device and the patient's head under a positive gage pressure. Direct contact between the cooling fluid and the patient's head provides a relatively rapid induction of systemic hypothermia in the patient, thereby minimizing or preventing ischemic injury in the patient. The console also removes air from a channel disposed about an inner rim of the cooling device, using a negative gage pressure. Such removal of the air from the channel seals the rim of the cooling device to the head of the patient, including portions of the channel in contact with hair of the patient's head, and minimizes leaking of the cooling fluid beyond the rim of the cooling device.

In one arrangement, the invention relates to a cooling device for inducing hypothermia. The head-cooling device includes a cap having an outer surface and an inner surface. The head-cooling device has a first sealing member disposed on the inner surface of the cap about a circumference defined by the cap. The first sealing member defines a first inner surface of the cap and a second inner surface of the cap where the first sealing member, the first inner surface of the cap, and a first portion of a head define a fluid circulation space. The head-cooling device has a second sealing member disposed on the second inner surface of the cap about a rim defined by the cap where the first sealing member, the second inner surface of the cap, and the second sealing member define an aspiration channel. The head-cooling device has a fluid inlet in communication with the fluid circulation space configured to receive a cooling fluid from a fluid source via a positive gage pressure and an aspiration channel outlet in communication with the aspiration channel. The aspiration channel is configured to remove air from the aspiration channel, via a negative gage pressure, to seal the rim of the cap to a second portion of the head. Such a configuration of the head-cooling device induces systemic hypothermia in a patient and minimizes leakage of the cooling fluid past the rim of the head-cooling device.

In one arrangement, the aspiration channel is configured to retrieve fluid from the fluid circulation space and the aspiration channel outlet is configured to remove fluid retrieved by the aspiration channel. In another arrangement, the head-cooling device includes a fluid collection reservoir in communication with the cap, the fluid collection reservoir in fluid communication with the fluid circulation space and in fluid communication with the aspiration channel.

In one arrangement, the head-cooling device includes a fluid outlet in communication with the cap and in fluid communication with the fluid circulation space, the fluid outlet configured to allow egress of the cooling fluid from the fluid circulation space. Such a configuration allows removal of the fluid from the fluid circulation space via gravity. In one arrangement, the head-cooling device defines a vent opening within the cap, the vent opening configured to maintain the pressure within the fluid circulation space at substantially atmospheric pressure.

In one arrangement the head-cooling device is coupled with a tissue cooling device, such as a body-cooling device that provides additional cooling to a patient to induce systemic hypothermia in the patient. The body-cooling device includes a fluid distribution membrane defining a plurality of fluid jets and a heat transfer membrane attached to the fluid distribution membrane and configured to cover a body portion, the fluid distribution membrane and the heat transfer membrane defining a fluid circulation chamber. In one arrangement, the jets create fluid turbulence within the fluid circulation chamber. Such turbulence increases the heat transfer between a cooling fluid within the fluid circulation chamber and the heat transfer membrane, thereby providing relatively rapid and efficient cooling to the body portion.

In one arrangement, the body-cooling device is configured as a neck-cooling device having a collar, a first body-cooling module attached to the collar, and a second body-cooling module attached to the collar. The first body-cooling module has a first fluid distribution membrane defining a plurality of fluid jets and has a first heat transfer membrane attached to the first fluid distribution membrane configured to cover a first neck portion. The first fluid distribution membrane and the first heat transfer membrane define a first fluid circulation chamber. The second body-cooling module has a second fluid distribution membrane defining a plurality of fluid jets and has a second heat transfer membrane attached to the second fluid distribution membrane configured to cover a second neck portion. The second fluid distribution membrane and the second heat transfer membrane define a second fluid circulation chamber.

In one arrangement, the cap comprises a flexible material and the head-cooling device comprises a substantially rigid shell in communication with the outer surface of the cap. The rigid shell minimized expansion or "ballooning" of the cap when, for example, a positive gage pressure source applies a positive gage pressure to the fluid circulation space.

In one arrangement, the fluid inlet and the fluid outlet each include a swivel joint configured to allow rotation of an inlet connector relative to the head-cooling device. The swivel joints, therefore, minimize kinking of an umbilical connecting the head-cooling device to a console (e.g., a console having a positive gage pressure source and a negative gage pressure source) during operation.

In one arrangement, the head-cooling device includes a movement stabilizer component in communication with the outer surface of the cap. The movement stabilizer component contacts a support surface (e.g., a gurney or stretcher) and minimizes rotation of the patient's head during operation of the head-cooling device.

In one arrangement, the aspiration channel defined by the first sealing member, the second inner surface of the cap, and the second sealing member includes a fluid absorption material, such as a sponge or foam. The absorption material, for example, aids in directing the fluid from the fluid circulation space into the aspiration channel and maintains the fluid within the aspiration channel to minimize leakage of the fluid.

In one arrangement, the head-cooling device has a third sealing member disposed on the inner surface of the cap about a circumference defined by the cap, the third sealing member oriented between the first sealing member and the second sealing member. The third sealing member creates a secondary seal between a patient's head and the head-cooling device during operation to minimize cooling fluid from flowing beyond the rim of the head-cooling device during operation.

Another aspect of this invention relates to a method for rapidly inducing systemic hypothermia in a patient's body to a predetermined temperature and then maintaining the patient's body at the predetermined temperature for an extended period of time. The head of the patient is cooled by a head-cooling device. Substantially simultaneously, the neck of the patient is cooled using a neck-cooling device for a period of time sufficient for at least some part of the patient's body to reach the predetermined temperature. Head cooling is then discontinued by de-activating or removing the head-cooling device from the patient's head. Neck cooling is continued in a manner sufficient to maintain at least some portion of the patient's body at the predetermined temperature for an extended period of time.

In one arrangement, the invention relates to a tissue cooling device for inducing hypothermia. The tissue cooling device has a tissue covering portion having an outer surface and an inner surface and a first sealing member disposed on the inner surface of the tissue covering portion about an inner edge defined by the tissue covering portion. The first sealing member defines a first inner surface of the tissue covering portion and a second inner surface of the tissue covering portion, the first sealing member, the first inner surface of the tissue covering portion, and a first portion of a tissue region of interest define a fluid circulation space. The tissue cooling device has a second sealing member disposed on the second inner surface of the tissue covering portion about an outer edge defined by the tissue covering portion. The first sealing member, the second inner surface of the tissue covering portion, and the second sealing member define an aspiration channel. The tissue cooling device has a fluid inlet in communication with the fluid circulation space that is configured to receive a cooling fluid from a fluid source via a positive gage pressure. The tissue cooling device has an aspiration channel outlet in communication with the aspiration channel that is configured to remove air from the aspiration channel, via a negative gage pressure, to seal the outer edge of the tissue covering portion to a second portion of the tissue region of interest. Such sealing of the outer edge of the tissue covering portion to a second portion of the tissue region of interest minimizes leaking of the cooling fluid beyond the outer edge of the tissue covering portion.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

Embodiments of the present invention provide techniques for inducing systemic hypothermia in a patient. A cooling system includes a console and a tissue covering device, such as a head-cooling device. An operator applies the head-cooling device to the head of a patient at risk for ischemic injury. The console provides a cooling fluid to a fluid circulation space located between the cooling device and the patient's head under a positive gage pressure. Direct contact between the cooling fluid and the patient's head provides a relatively rapid induction of systemic hypothermia in the patient, thereby minimizing or preventing ischemic injury in the patient. The console also removes air from a channel disposed about an inner rim of the cooling device, using a negative gage pressure. Such removal of the air from the channel seals the rim of the cooling device to the head of the patient, including portions of the channel in contact with hair of the patient's head, and minimizes leaking of the cooling fluid beyond the rim of the cooling device.

Figure 1:
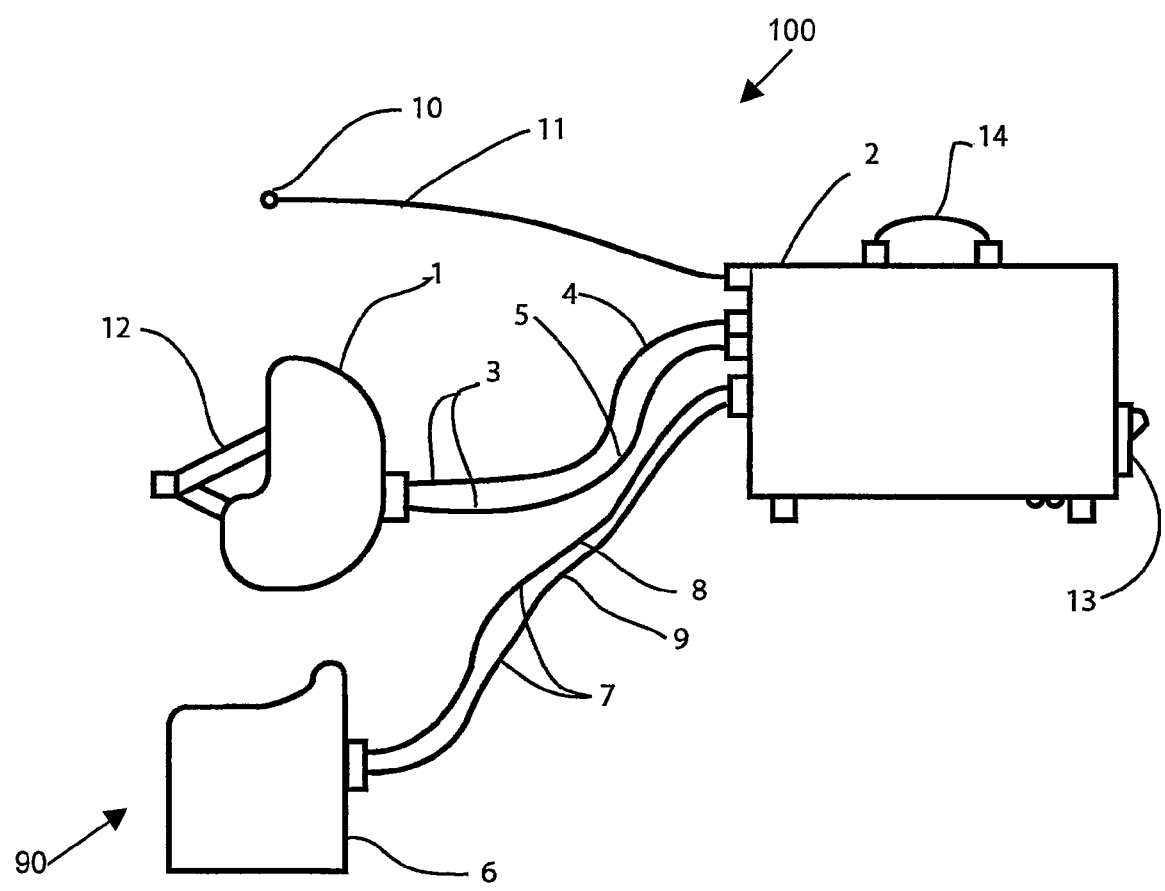
FIG. 1 depicts a cooling system showing a head-cooling device, a neck-cooling device, a body temperature sensor, and a console, according to one embodiment of the invention.

FIG. 1 depicts an arrangement of a cooling system 100. The cooling system includes a tissue covering device, such as a head-cooling device 1, a console 2, a tissue covering device, such as a body-cooling device 6, and a body temperature sensor 10.

The head-cooling device 1, in one arrangement, is removably connected to console 2 by umbilical 3 having, for example, a cooling fluid infusion tube 4 and a cooling fluid aspiration tube 5. The body-cooling device 6, such as a neck-cooling device 90, is removably connected to console 2 by umbilical 7 having, for example, a cooling fluid inlet tube 8 and a cooling fluid outlet tube 9.

The body temperature sensor 10, in one arrangement, is removably connected to console 2 by a body temperature sensor lead 11. The body temperature sensor 10 is configured to attach onto (e.g., on an outer surface) or within (e.g., within a natural orifice) a patient's body to measure the temperature of the patient during operation of the cooling system 100. In one arrangement, the body temperature sensor 10 is an esophageal temperature sensor configured to insert within an esophagus of a patient to measure core body temperature. In another arrangement, the body temperature sensor in a bladder temperature sensor or a tympanic temperature sensor configured to insert within a bladder or ear, respectively, of a patient.

The console 2 has a cooling fluid supply, such as a reservoir 56, for provision of cooling fluid to the head-cooling device 1 and the body-cooling device 6 under positive gage pressure (e.g., from a pressure source or positive gage pressure source, such as a water pump, associated with the console 2). The console 2 also has, in one arrangement, a suction source or negative gage pressure source, such as an air pump, configured to scavenge cooling fluid from head-cooling device 1 and neck-cooling device 90. The console 2 also has, in one arrangement, a fluid cooling mechanism for cooling the fluid (e.g., after scavenging the cooling fluid from the head-cooling device 1 and the body-cooling device 6) and a flow rate adjustment mechanism to adjust the flow of cooling fluid from console 2 to the head-cooling device 1 and the body-cooling device 6 according to signals received from the body temperature sensor 10, during operation, in order to control body cooling (e.g., the duration of application of cooling fluid to the patient during operation of the cooling system 100). In one arrangement, the console 2 has a handle 14 that allows a user to grasp and transport the console 2 to a patient.

In one arrangement, electrical power is supplied to the console 2 by an internal power source, such as a rechargeable battery (e.g., such as illustrated in FIG. 11), and by an external power source connected to the console 2 by an AC power adapter (not shown). The battery allows a user (e.g., operator or emergency technician) to transport the cooling system 100 to a patient at risk for ischemic injury at a location outside of a hospital (e.g., at an emergency site where an external power source or supply, such as provided from a wall outlet, is unavailable). For example, during operation, the console 2 provides cooling to a patient for greater than approximately 5 hours using internal power source. The console 2 then provides cooling to the patient for an indefinite time period using power from an external power supply, such as a wall outlet (e.g., after the patient is transferred to a patient care facility).

During operation, upon presentation of a patient with an ischemic condition, the cooling system 100 is applied to the patient. For example, the head-cooling device 1 is placed on top of the patient's head and is secured using a chinstrap 12. The neck-cooling device 90 is applied to the patient's neck, such as by using Velcro fasteners (see FIG. 9 for construction details). The body temperature sensor 10 is applied to the surface of the patient or inserted into a natural orifice of the patient (e.g., this step can be accomplished at a later time. In another arrangement, the system operates without the temperature sensor 10 prior to the patient's body reaching a pre-determined temperature). The head-cooling device 1, the neck-cooling device 90, and the body temperature sensor 10 are connected to the console 2.

Figure 12:
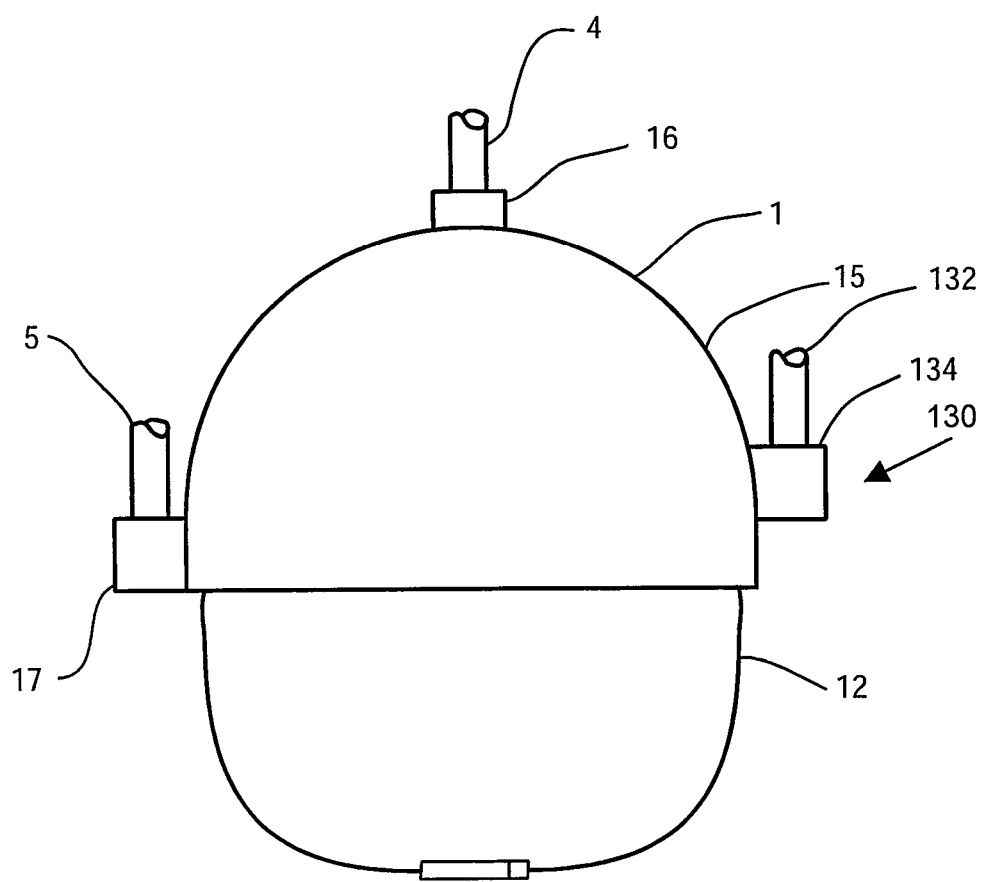
FIG. 12 illustrates a head-cooling device, according to another embodiment of the invention.

The fluid reservoir 56, as shown in FIG. 12, is filled with a cooling fluid, such as saline and brine ice, water and ice, saline, or water, for example. A user activates the system 10 by positioning the on/off switch 13 to the "on" position. In one arrangement, the console 2 of the cooling system 100 provides cooling fluid to the head-cooling device 1 via positive gage pressure and removes fluid from the head-cooling device 1 via negative gage pressure. The cooling system 100 utilizes the body temperature sensor 10 (e.g., measurements taken by the temperature sensor 10) to modulate cooling (e.g., provision of cooling fluid to the patient) in order to maintain the patient's body at a predetermined hypothermic temperature. For example, the console 2 provides cooling fluid to the head-cooling device 1 until the patient's body reaches a pre-determined (e.g., preset) hypothermic temperature, as measured by the body temperature sensor 10, at which time the system modulates cooling by modulating the flow of cooling fluid to the head-cooling device 1 and the body-cooling device 6 according to signals received from body temperature sensor 10.

In one arrangement, the console 2 forms a closed loop fluid circulation system between the head-cooling device 1 and the reservoir 56 of the console 56. Such a closed loop system allows continuous cooling of the cooling fluid, such as by a thermal battery 342, as described below. In another arrangement, a user can operate the cooling system 100 for an extended period of time by re-supplying the reservoir 56 with brine ice or ice to reduce the temperature of the cooling fluid within the reservoir 56.

The cooling system 100 allows for relatively rapid induction of systemic hypothermia to a patient at risk of ischemic injury for minimization or prevention of ischemic injury in the patient. For example, the cooling system 100 allows for induction of protective levels of hypothermia in a brain of a patient at risk of ischemic injury. The cooling system 100 also allows for non-invasive application and induction of systemic hypothermia in the pre-hospital setting by emergency medical personnel with minimal specialized (e.g., surgical) skills.

The cooling system 100 allows emergency medical personnel, in the pre-hospital setting, to relatively rapidly induce of systemic hypothermia in a patient to a predetermined temperature and maintain the systemic hypothermia for an extended period of time (e.g., after the patient arrives at the hospital). In one arrangement, the console 2 is sized to allow for portability of the cooling system 100 outside of the hospital setting to minimize ischemic injury in patients at-risk for ischemic injury prior to the patients arriving at the hospital.

Figure 2:
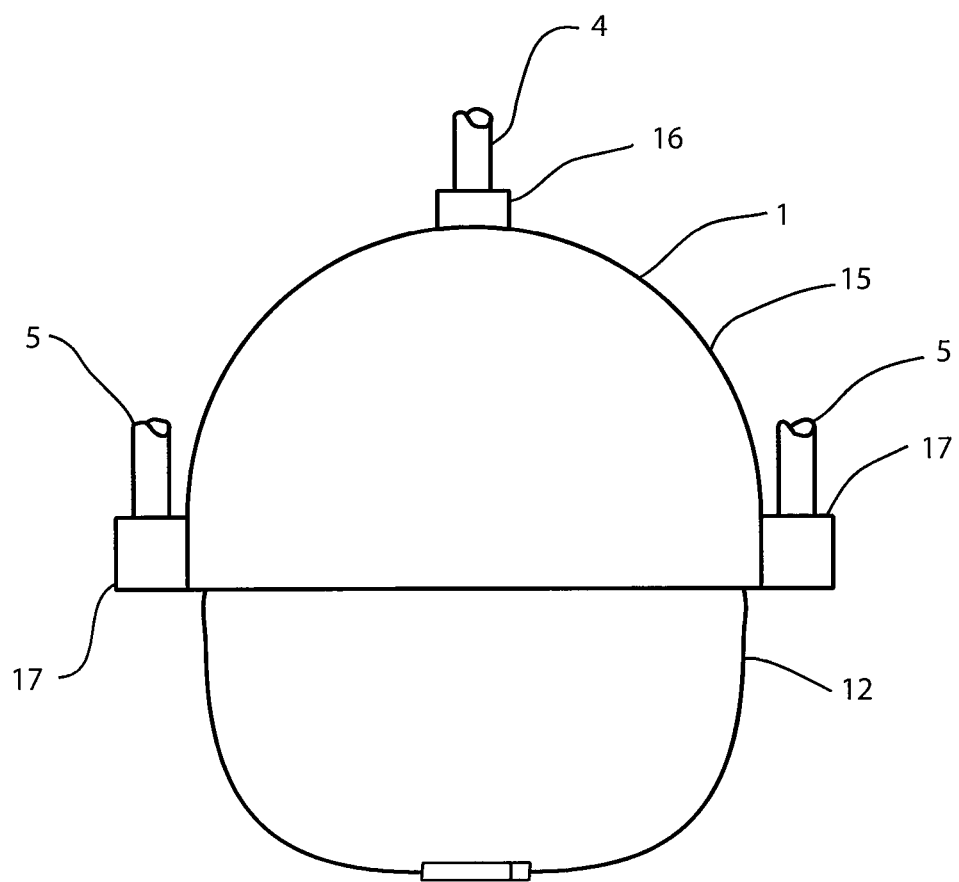
FIG. 2 depicts the head-cooling device of FIG. 1, according to one embodiment of the invention.

FIG. 2 depicts an arrangement of the head-cooling device 1. Head-cooling device 1 includes a tissue covering portion, such as a head cap 15, a chinstrap 12, cooling fluid infusion tube 4, cooling fluid aspiration tube 5 (e.g., two bifurcated cooling fluid aspiration tubes 5 are shown which join into a single tube by a "Tee" connector—not shown), infusion manifold 16, and one or more aspiration manifolds 17 (e.g., aspiration channel outlets 252). Cooling fluid enters head-cooling device 1 through cooling fluid infusion tube 4 and infusion manifold 16 under positive gage pressure between approximately 2 and 40 PSI. In one arrangement, cooling fluid is removed from head-cooling device 1 by cooling fluid aspiration tubes 5 and aspiration manifold 17 under negative gage pressure between approximately −0.1 and −10 PSI. Head cap 15 can be formed from either a rigid structure molded from thermoplastic, such as nylon, vinyl, polycarbonate, or from a flexible structure molded from an elastomer such as silicone rubber. Chinstrap 12 holds head-cooling device 1 to the patient's head.

Figure 3:
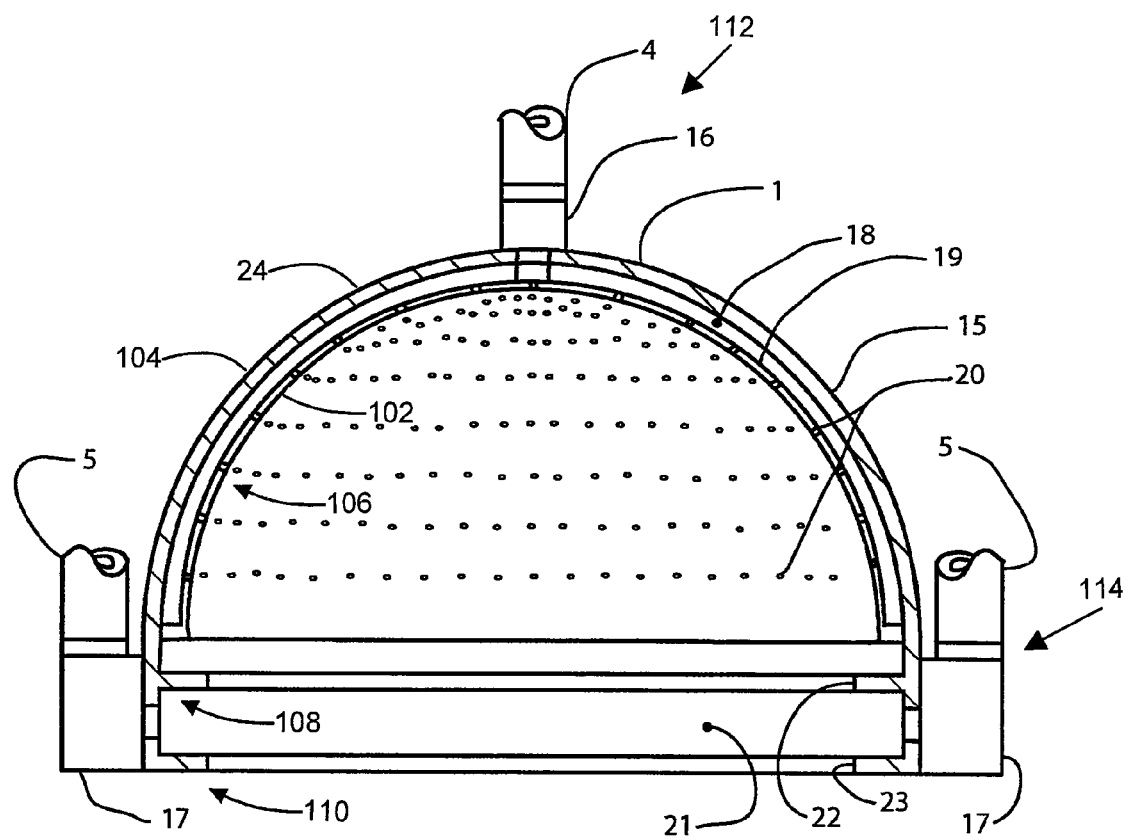
FIG. 3 depicts a sectional-view of the head-cooling device of FIG. 2, according to one embodiment of the invention.

FIG. 3 depicts, in sectional view, an arrangement of the head-cooling device 1. The head cooling device 1 has a head cap 15 having an inner wall 19 having an inner surface 102, an outer wall 24 having an outer surface 104, fluid channels 18 formed between inner wall 19 and outer wall 24, and fluid jets 20 formed in inner wall 19 over fluid channels 18.

The head-cooling device 1 has a first sealing member or inner seal 22 disposed on the inner surface 102 of the cap 15 about an inner edge or circumference defined by the cap 15. The first sealing member 22 divides (e.g., defines) the inner surface 102 of the cap 15 into a first inner surface 106 and a second inner surface 108. In such a configuration, the first sealing member 22, the first inner surface 102 of the cap 15, and a first portion of a patient's head defines a fluid circulation space 25. The head-cooling device 1 also has a second sealing member 23 disposed on the second inner surface 108 of the cap 15 about an outer edge or rim 110 defined by the cap. In such a configuration, the first sealing member 22, the second inner surface 108 of the cap 15, and the second sealing member 23 define an aspiration channel, an aspiration channel 21.

The head-cooling device 1 has a fluid inlet 112, such as infusion manifold 16, in communication with the fluid circulation space 25 and configured to receive a cooling fluid from a fluid source via a positive gage pressure. In one arrangement, the infusion manifold 16 is bonded to the head cap 15 or, alternately is integrally molded into head cap 15. The infusion manifold 16 provides fluid communication between cooling fluid infusion tube 4 (e.g., in fluid communication with the positive gage pressure source) and fluid channels 18.

The head-cooling device 1 has an aspiration channel outlet, such as aspiration manifolds 17, in communication with the aspiration channel 21. The aspiration channel outlet is configured to remove air from the aspiration channel 21, via a negative gage pressure, to seal the rim 110 of the cap 15 to a second portion 118 of the head 29. In one arrangement, the aspiration manifolds 17 are bonded to head cap 15 or, alternately, are integrally molded into head cap 15. The aspiration manifolds 17 provide fluid communication between cooling fluid aspiration tube 5 (e.g., in fluid communication with the negative gage pressure source) and aspiration channel 21.

Fluid channels 18 distribute cooling fluid substantially throughout the head cap 15 and communicate cooling fluid from infusion manifold 16 to, in one arrangement, fluid jets 20 that direct streams of cooling fluid at an angle substantially normal to the scalp of the patient. The fluid channels 18, in one arrangement, are configured in a radial fashion where each channel 18 originates at the infusion manifold 16 and terminates prior to the aspiration channel 21 as shown. In another arrangement, the fluid channels 18 are configured as a series of circumferential channels in combination with radial channels. The fluid channels 18 are configured to provide distribution of cooling fluid through a substantially even distribution of fluid jets 20 throughout the head cap 15. In one arrangement, the fluid jets 20 are formed as perforations or holes in the inner wall 19 and are closed until pressure is applied. For example, the holes have a major diameter between approximately 0.005 and 0.030 inches. The fluid channels 18 provide distribution of the fluid to the patient's head such that the thickness or distribution of the hair on the head, face, or neck of the patient does not substantially affect (e.g., limit) cooling of the patient's head (e.g., does not substantially affect induction of hypothermia).

Figure 4:
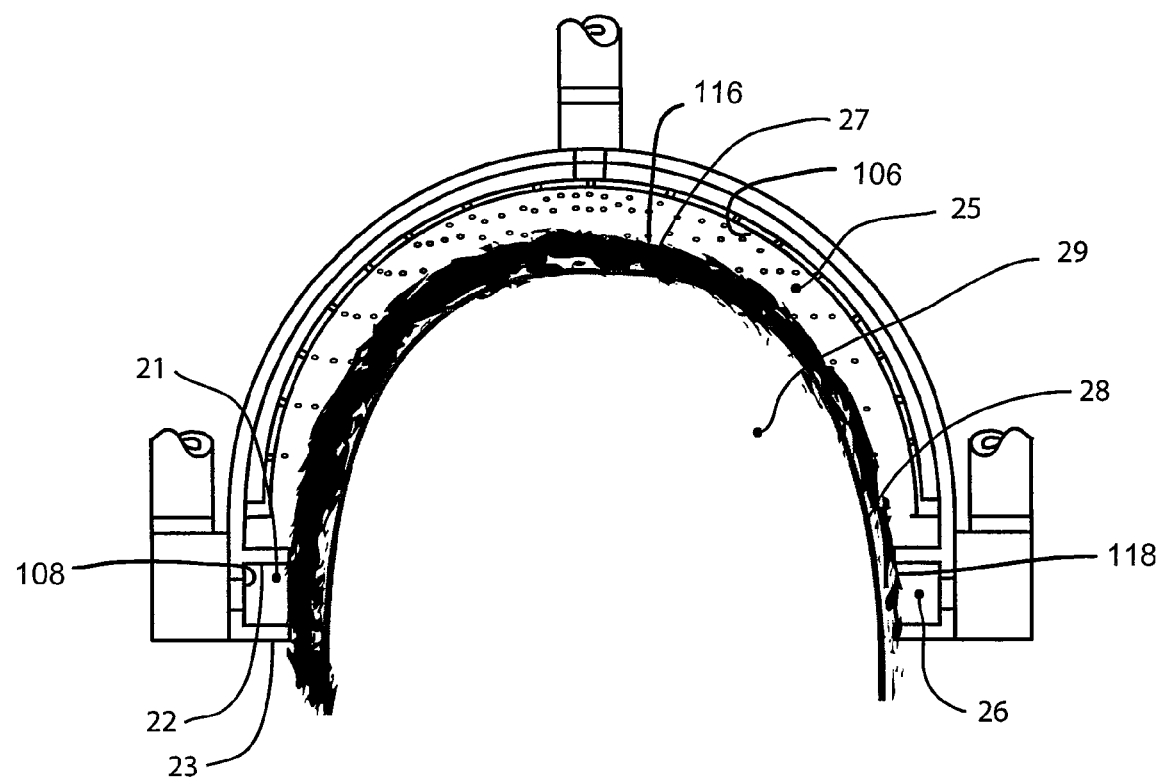
FIG. 4 depicts the head-cooling device in sectional view mounted on the head of a patient, according to one embodiment of the invention.

FIG. 4 depicts, in one arrangement, a sectional view of the head-cooling device mounted on the head 29 of a patient showing the cooling fluid circulation space 25, the cooling fluid aspiration space 26, and the functional relationship between the cooling fluid circulation space 25 and the cooling fluid aspiration space 26. Cooling fluid circulation space 25 comprises the volumetric space between inner wall 19 (e.g., the first inner surface 102 of the cap 15), patient's scalp 28 (e.g., the first portion of the head 116 or first portion of the tissue region of interest), and inner seal 22 (e.g., the first sealing member), and includes the volumetric space occupied by the patient's hair 27 within the defined cooling fluid circulation space 25.

In one arrangement, during operation, the console 2 of the cooling system 100 (e.g., the positive gage pressure source) maintains the fluid circulation space 25 (e.g., the region over the scalp and between the scalp and the head-cooling device 1) at a positive gage pressure. Typically, substantial contact between an inner surface 102 of a head-cooling device and the scalp results in diminished heat transfer effectiveness due to a reduction in the surface area of the scalp available for heat exchange with the cooling fluid. Positive gage pressure within the fluid circulation space 25 limits the ability for the inner surface 102 of the head-cooling device 1 to contact the patient's scalp (e.g., head), thereby maximizing the efficiency of the cooling fluid with respect to removal of heat from the patient's head 29.

Cooling fluid aspiration space 26 includes the volumetric space between the patient's scalp 28 (e.g., the second portion of the head 118 or second portion of the tissue region of interest) and a space within aspiration channel 21 comprising inner seal 22, outer seal 23 and second inner surface 108. The aspiration channel 21, in one arrangement, is molded from an elastomer material such as silicone rubber. The aspiration channel 21, in one arrangement, is disposed about the entire circumference of the inner surface 102 at the bottom edge 110 (e.g., rim) of the head cap 15 as shown and, in one arrangement, is sized such that the inner diameter of aspiration channel 21 as defined by the inner diameter of inner seal 22 and/or outer seal 23 is approximately 2 to 30 percent smaller than the circumference of the patient's head 29. Since the circumference of the aspiration channel 21 is smaller than the patient's head 29, when the head cap 15 is placed on the patient's head, the inner seal 22, and the outer seal 23 contacts the patient's scalp 28 with a force proportional to the difference in circumference between that aspiration channel 21 and the patient's head 29. In such an arrangement, the force generated by the aspiration channel 21 on the patient's head maintains the head cap 15 on the patient's head 29 during operation of the cooling system 100 and minimizes cooling fluid from leaking past the rim 110 of the head cap 15 during operation.

In one arrangement, the inner seal 22 is configured by geometry and material selection to resist the flow of fluid from fluid circulation space 25 through the hair 27 into fluid aspiration space 26 such that cooling fluid in fluid circulation space 25 remains at a positive gage pressure between approximately 0.1 and 10 PSI with a fluid flow into head cap 15 of between 0.1 and 1.0 gallons per minute. The outer seal 23, in one arrangement, is configured by geometry and material selection to resist the flow of air through the hair 27 from outside head cap 15 into aspiration channel 21 such that, during operation, pressure within aspiration channel 21 is maintained at a negative gage pressure between approximately −0.1 and −10 PSI by the negative gage pressure source provided by console 2. Cooling fluid is scavenged completely from the head cap 15, via aspiration channel outlet, provided that the pressure within the aspiration channel 21 remains at a negative gage pressure.

For example, during operation the positive gage pressure source of the console 2 provides cooling fluid, under positive gage pressure, to the cooling device via inlet 112. The cooling fluid enters the infusion manifold 16 and travels through the fluid channels 18 and, in one arrangement, through the fluid jets 20, into the fluid circulation space 25. The positive gage pressure source aids in maintaining the pressure within the fluid circulation space 25 between approximately 0.1 and 10 PSI. Also during operation, the negative gage pressure source of the console 2 removes air from within the aspiration channel 21 (e.g., from within the aspiration space), thereby sealing the rim 110 of the cap 15 against the second portion 118 of the head (e.g., a periphery of the tissue region of interest) to minimize leakage of the cooling fluid beyond the rim 110 of the cap 15.

In one arrangement, the aspiration channel 21 receives cooling fluid from the fluid circulation space 25. For example, during operation cooling fluid enters the aspiration channel 21 by wicking through the patient's hair past the first sealing member 22 (e.g., cooling fluid from the fluid circulation space 25 migrates, via the hair between the first portion 116 of the head and the second portion 118 of the head, into the aspiration channel 21). In such a case, the negative gage pressure applied to the aspiration channel 21 removes the cooling fluid from the aspiration channel 21 via the aspiration channel outlet (e.g., manifold 17). The aspiration channel 21, therefore, minimizes leakage of the cooling fluid beyond the rim 110 of the cap 15.

Figures 5A, 5B:
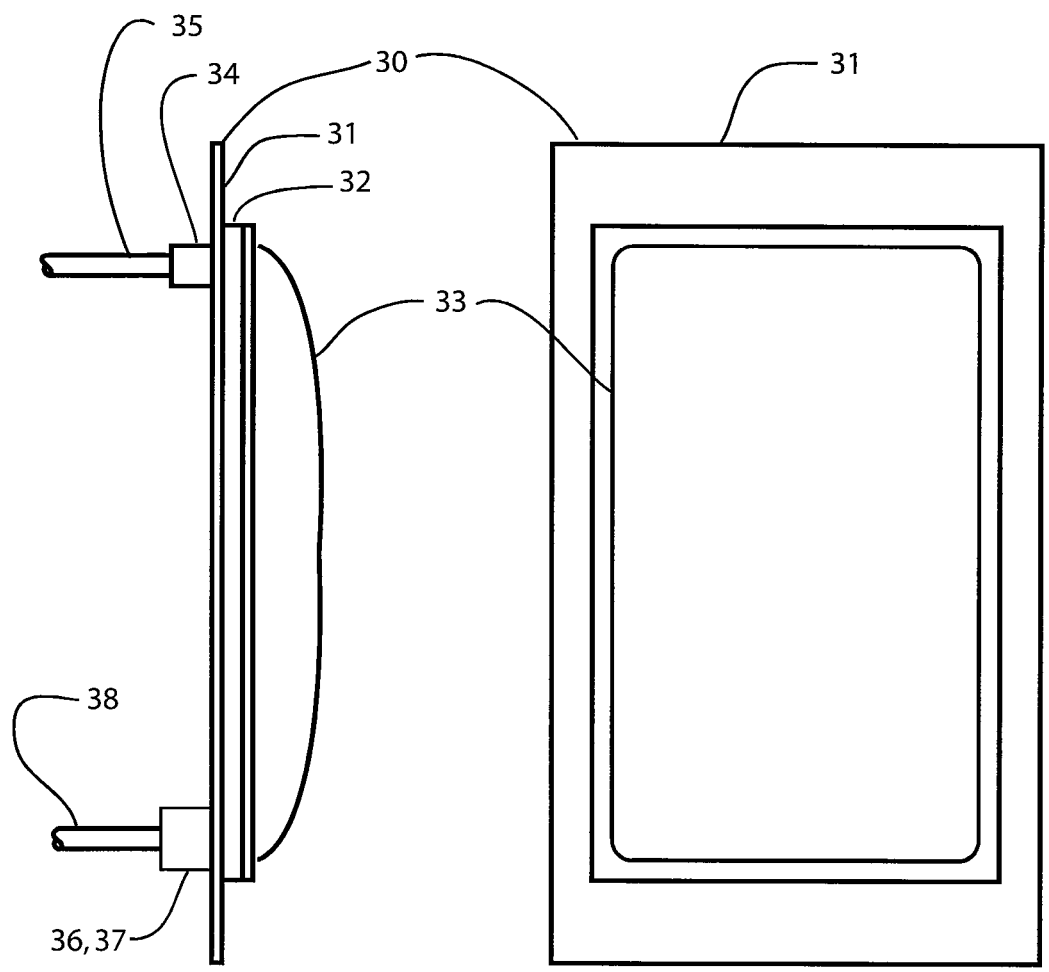
FIG. 5A depicts a side view of a body-surface cooling module under operational pressure, according to one embodiment of the invention.
FIG. 5B depicts a front view of the body-surface cooling module, of FIG. 5A, under operational pressure, according to one embodiment of the invention.

FIG. 5A depicts a side view of generic body-surface cooling module 30 (e.g., tissue covering portion) of a tissue cooling device configured as a body-cooling device 6 under operational pressure. FIG. 5B depicts a front view of a generic body-surface cooling module 30 under operational pressure. The body-surface cooling module 30, in one arrangement, includes substrate 31, fluid distribution membrane 32, heat transfer membrane 33, fluid inlet fitting 34, fluid inlet tube 35, fluid outlet fitting 36 containing fluid outlet pressure relief valve 37 (not shown), and fluid outlet tubing.

During operation, cooling fluid (not shown) enters body-surface cooling module 30 at a gage pressure between approximately 5 and 20 PSI through fluid inlet tube 35 and fluid inlet fitting 34. Fluid distribution membrane 32 directs jets of cooling fluid at the side of heat transfer membrane 33 that is opposite the side shown (see FIGS. 6, 7, 8 & 9 for construction details). Cooling fluid exits body-surface cooling module 30 through fluid outlet pressure relief valve 37, fluid outlet fitting 36, and fluid outlet tube 38. Fluid outlet pressure relief valve is constructed such that a backpressure is maintained in the body-surface cooling module between approximately 0.2 and 5 PSI gage. Back pressures within body-surface cooling module 30 causes heat transfer membrane 33 to distend and contact a body surface of the patient. The construction of substrate 31 is determined by the location on the patient's body where the body-surface cooling module 30 is to be applied. The substrate 31, in one arrangement, is configured with straps and fasteners having particular geometric shapes in order to accommodate specific parts of the body. For example, FIG. 9 depicts a substrate comprising a collar intended for neck cooling.

Figure 6:
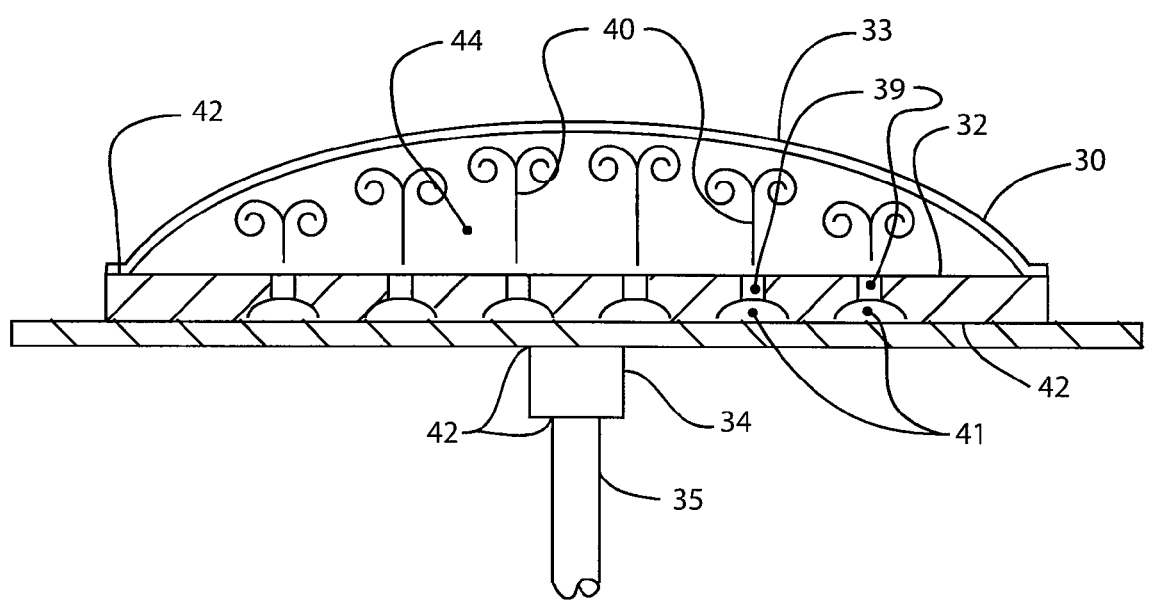
FIG. 6 depicts a sectional view of the body-surface cooling module of FIG. 5A showing the operational relationship between a heat transfer membrane, a cooling fluid distribution membrane, a fluid circulation space, fluid jets, and fluid channels.

FIG. 6 depicts in sectional view the construction details and operational function of a generic body-surface cooling module 30. Cooling fluid (not shown) enters fluid channels 41 (e.g., such as formed by adhesive bonding, via adhesive 42, of fluid distribution membrane 32 and substrate 31) under positive gage pressure of, for example, about 5 to 20 PSI through fluid inlet tube 35 and fluid inlet fitting 34. Cooling fluid exits fluid channels 41 through fluid jets 39 into fluid circulation chamber 44 (e.g., formed between fluid distribution membrane 32 and heat transfer membrane 33) substantially perpendicular to the heat transfer membrane 33. The fluid is maintained at a predetermined gage pressure between approximately 0.2 and 5 PSI by outlet pressure relief valve 37, not shown. Since cooling fluid pressure within fluid channels 41 is at a higher pressure than cooling fluid pressure within fluid circulation chamber 44, cooling fluid from the jets is accelerated by the difference in pressure. The jets of fluid 40 are directed at the inner surface of heat transfer membrane 33 and create fluid turbulence at the inner surface of heat transfer membrane 33 (e.g., providing a relatively high Reynolds number at the surface of the heat transfer membrane while maintaining a low and positive fluid gage pressure within the fluid chamber). Such turbulence increases the heat transfer from the patient's body, across heat transfer membrane 33, and into cooling fluid contained in fluid circulation chamber 44.

The amount of fluid turbulence at the inner surface of heat transfer membrane 33 is a function of the fluid pressure differential between pressure in fluid channels 41 and the pressure in fluid circulation chamber 44 and the number and spacing of fluid jets 39, and the size of fluid jets 39. A pressure differential of between approximately 5 and 15 PSI with a fluid jet 39 spacing of between approximately 0.25 and 0.5 inches in a 2 dimensional grid, and a fluid jet 39 diameter between approximately 0.10 and 0.040 inches will provide sufficient turbulence at the inner surface of heat transfer membrane 33 to effect efficient heat transfer.

Substrate 31, fluid distribution membrane 32, heat transfer membrane 33, fluid inlet fitting 34, and fluid outlet fitting (not shown) may be molded from silicone rubber by conventional processes and may be assembled as shown using silicone adhesive 42. In one arrangement, the heat transfer membrane 33 has a thickness between approximately 0.001 and 0.015 inches. In one arrangement, the fluid distribution membrane has a thickness between approximately 0.06 and 0.18 inches. The fluid inlet tube 35 and fluid outlet tube, in one arrangement, have an inner diameter between approximately 0.12 and 0.38 inches, and may be made of an elastomer material, such as silicone rubber, or a thermoplastic material such as nylon, vinyl, or polycarbonate. Fluid inlet tube 35 and fluid outlet tube 38 can be insulated with foam rubber, for example. Fluid inlet tube 35 and fluid outlet tube 38 may be integrated into a single assembly to form an umbilical.

Figures 7A, 7B:
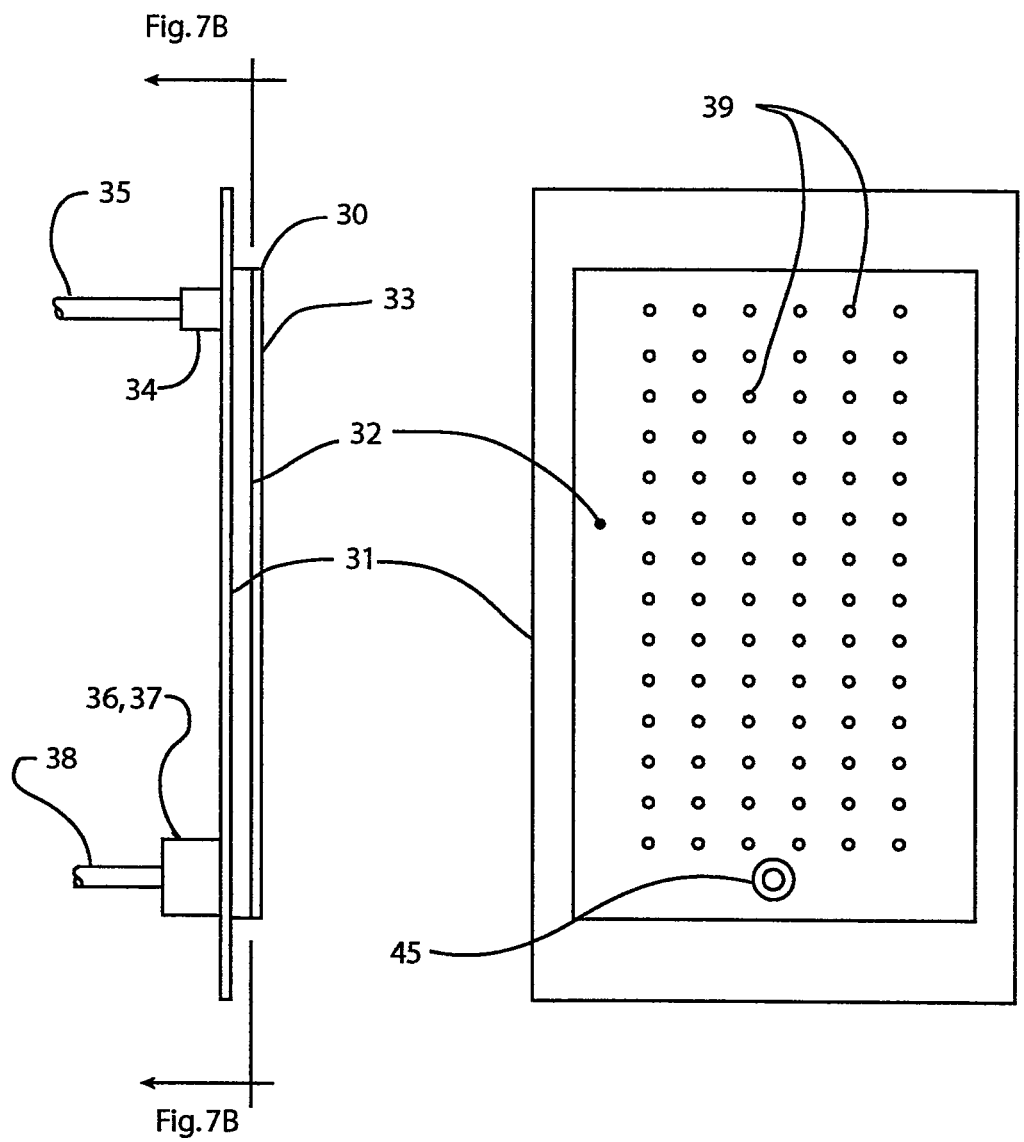
FIG. 7A depicts a side view of a body-surface cooling module, according to another embodiment of the invention.
FIG. 7B depicts a sectional view of the body-surface cooling module of FIG. 7A showing the fluid jets and the cooling fluid outlet port.

FIG. 7A depicts a side view of an unpressurized body-surface cooling module 30. FIG. 7B depicts in sectional view between heat transfer membrane 33 and fluid distribution manifold 32 showing the surface of fluid distribution manifold 32 and the distribution of fluid jets 39, and fluid outlet port 45. Fluid jets 39 are arranged in a substantially even distribution about the face of fluid distribution membrane 32, as shown. Fluid outlet port 45 provides fluid communication from fluid circulation chamber 44 (see FIG. 6) to fluid outlet pressure relief valve 37, fluid outlet fitting 36, and fluid outlet tube 38.

Figure 8A:
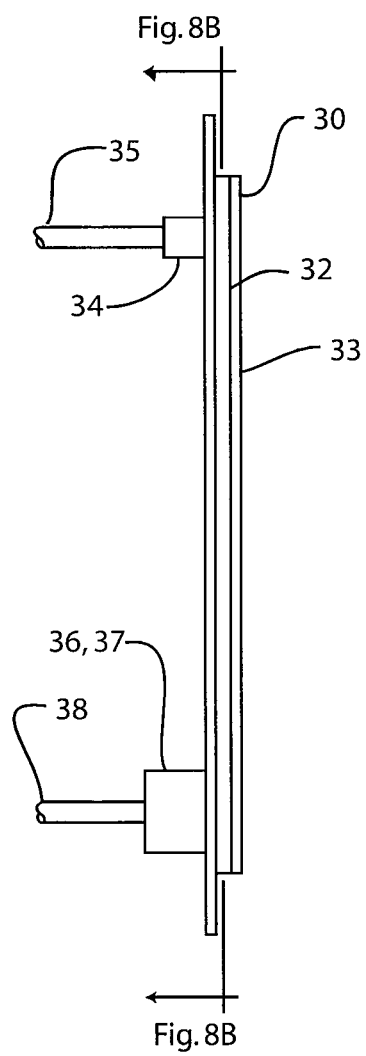
FIG. 8A depicts a side view of a body-surface cooling module, according to another embodiment of the invention.
Figure 8B:
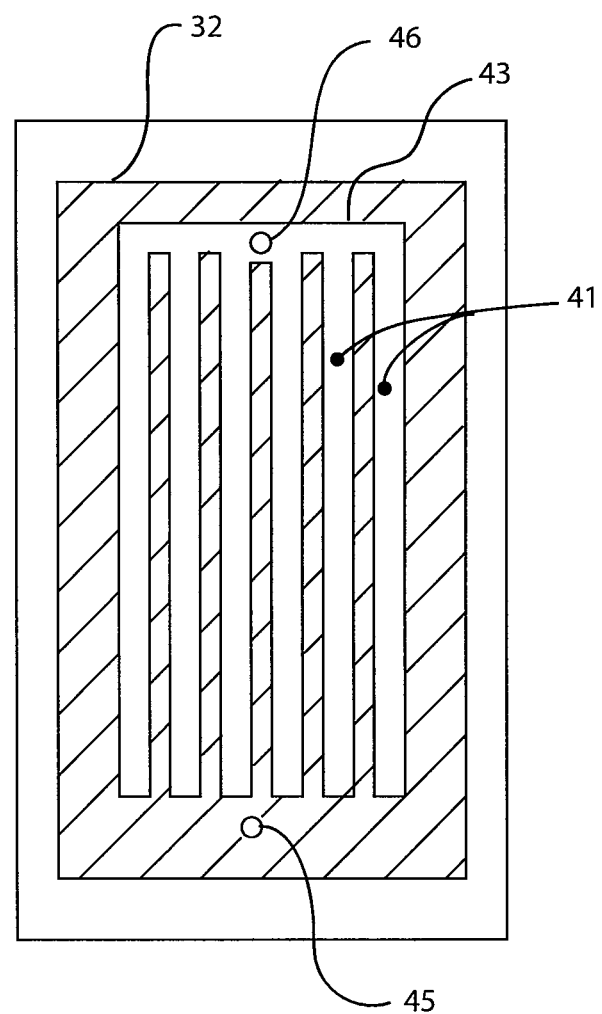
FIG. 8B depicts a sectional view of the body-surface cooling module of FIG. 8A showing the fluid manifold, cooling fluid inlet port, and cooling fluid outlet port.

FIG. 8A depicts a side view of a generic body-surface cooling module 30 un-pressurized. FIG. 8B depicts in sectional view of generic body-surface cooling module 30 showing fluid manifold 43 of fluid distribution membrane 32 comprising multiple fluid channels 41, and fluid inlet port 46. The fluid manifold 43 distributes cooling fluid to the fluid jets 39 (see FIG. 7B). Fluid inlet port 46 communicates cooling fluid from fluid inlet tube 35 and fluid inlet fitting 34 to fluid manifold 43.

Figure 9A:
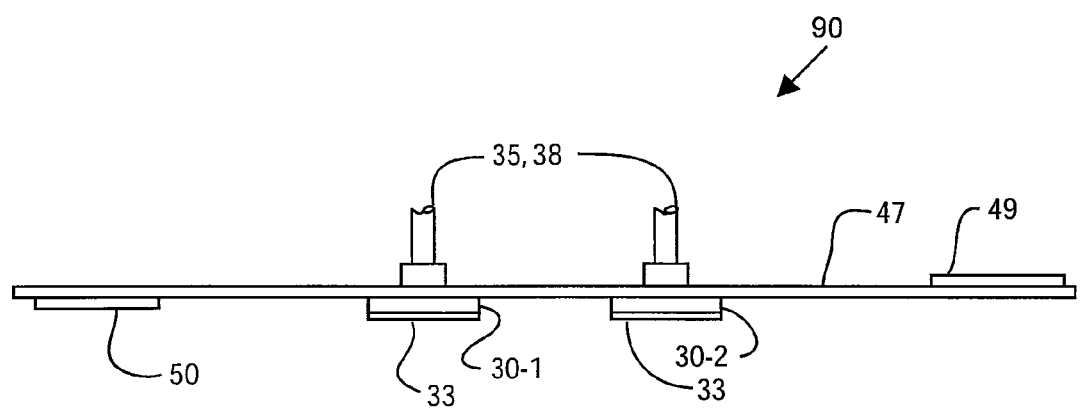
FIG. 9A depicts a side view of a neck-cooling device, according to one embodiment of the invention.
Figure 9B:
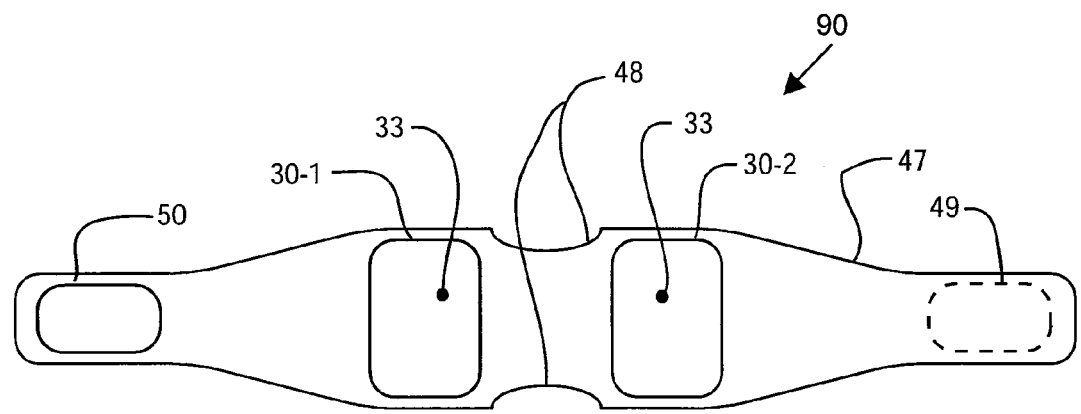
FIG. 9B depicts a front view of the neck-cooling device of FIG. 9A, according to one embodiment of the invention.

FIG. 9A depicts a side view of the body-cooling device 6 configured as a neck-cooling device 90. FIG. 9B depicts a top view of the neck-cooling device 90. Neck-cooling device 90 has a collar 47 (equivalent to substrate 31 in FIGS. 5, 6, 7 & 8), a first body-surface cooling module 30-1, and a second body-surface cooling module 30-2. For the neck-cooling device 90, each body-surface cooling module 30-1, 30-2 is approximately 3.5 inches high, approximately 2 inches wide, and approximately 0.12 inches thick. The two body-surface cooling modules 30 are spaced approximately 1.5 inches apart centered on either side of the chin cutout 48.

In one arrangement, the first body-surface cooling module 30-1 is configured to cover a first neck portion (e.g., constructed to cool the surface of the neck of the patient in the vicinity of the left carotid artery and the left jugular vein) and the second body-surface cooling module 30-2 is configured to cover a second neck portion (e.g., constructed to cool the surface of the neck of the patient in the vicinity of the right carotid artery and the right jugular vein). In such an arrangement, the neck-cooling device effectively cools the blood flowing through the carotid arteries and jugular veins without substantially cooling the major muscles in the back of the neck thereby minimizing muscle spasm that result from substantial cooling of the major muscles of the neck.

To apply to the neck-cooling device 90 to the patient, in one arrangement, the cooling modules are placed over the throat of the patient with each cooling module positioned on either side of the Adams Apple. The collar is then fastened behind the neck with the Velcro loop pad 50, and Velcro hook pad 49. Fluid inlet tubes 35 from each module may be joined by a "tee" fitting or integrally formed manifold into a single conduit. Fluid outlet tubes 38 from each module may be joined by a tee fitting or integrally formed manifold into a single conduit. Fluid inlet and fluid outlet conduits may then be assembled into a single umbilical.

Figure 10A:
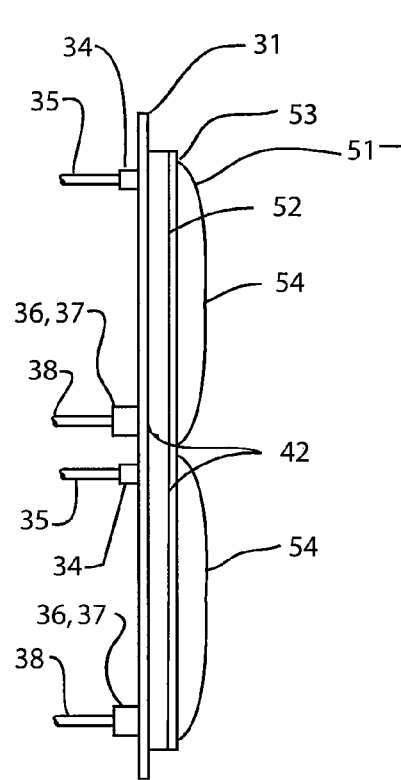
FIG. 10A depicts a side view of a body-surface cooling appliance having multiple body-surface cooling modules, according to one embodiment of the invention.
Figure 10B:
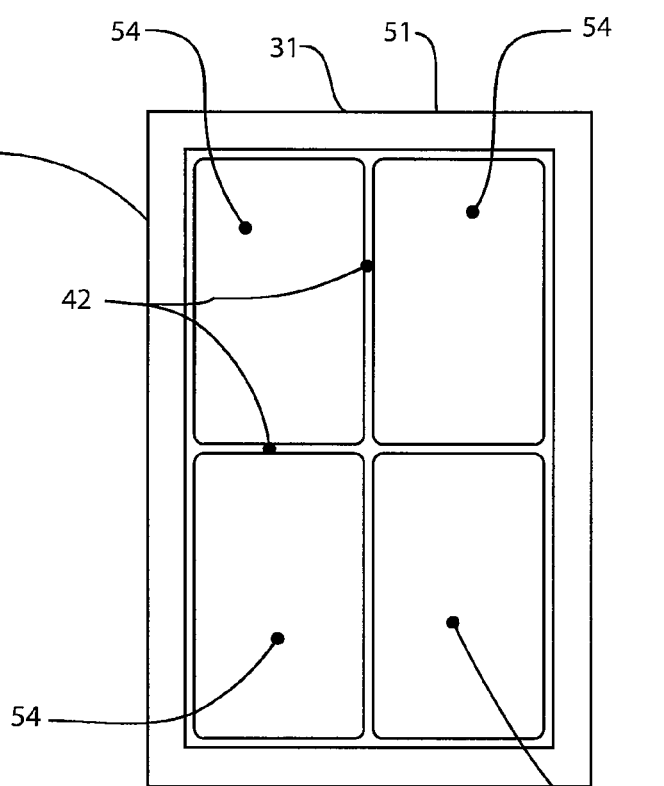
FIG. 10 B depicts a top view of the body-surface cooling appliance of FIG. 10A, according to one embodiment of the invention.
FIG. 10C depicts a front view of the body-surface cooling appliance of FIG. 10A, according to one embodiment of the invention.
Figure 10C:
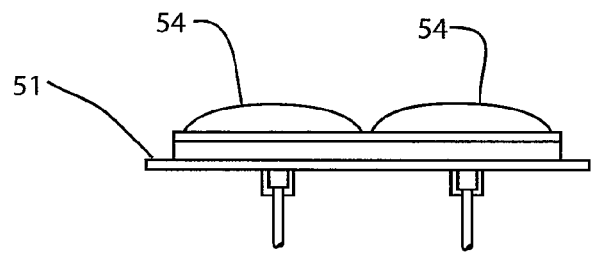

FIG. 10A depicts a side view of an arrangement of body-surface cooling appliance 51 having multiple (4 in this example) body-surface cooling modules 30. FIG. 10B depicts a front view of body-surface cooling appliance 51. FIG. 10C depicts a second side view of body-surface cooling appliance 51.

In one arrangement, the body-surface cooling appliance 51 has substrate 31, multiple module fluid distribution membrane 52, multiple module heat transfer membrane 53, four fluid inlet tubes 35, four fluid outlet tubes 38, four fluid inlet fittings 34, four fluid outlet fittings 36 containing four outlet pressure relief valves 37, and adhesive 42. The multiple module fluid distribution membrane 52 is molded, for example, with four fluid manifolds 43, four fluid inlet ports 46, and four fluid outlet ports 45 (see FIGS. 8A and 8B). Each fluid manifold 43, fluid inlet port 46, and fluid outlet port 45 are configured as a single body-surface cooling module in a four-quadrant arrangement as shown. The multiple module heat transfer membrane 53 is sized to match the size of multiple module fluid distribution membrane 52, and is bonded to multiple module fluid distribution membrane 52 using silicone adhesive 42 in the pattern shown to form four separate fluid circulation chambers 41 (see FIG. 6). Each individual cooling module has its own fluid inlet and fluid outlet means previously described. Various body-surface cooling appliances may be constructed using the multiple cooling module construction technique disclosed above including cooling blankets, cooling vests, cooling trousers, and cooling suits.

Figure 11A:
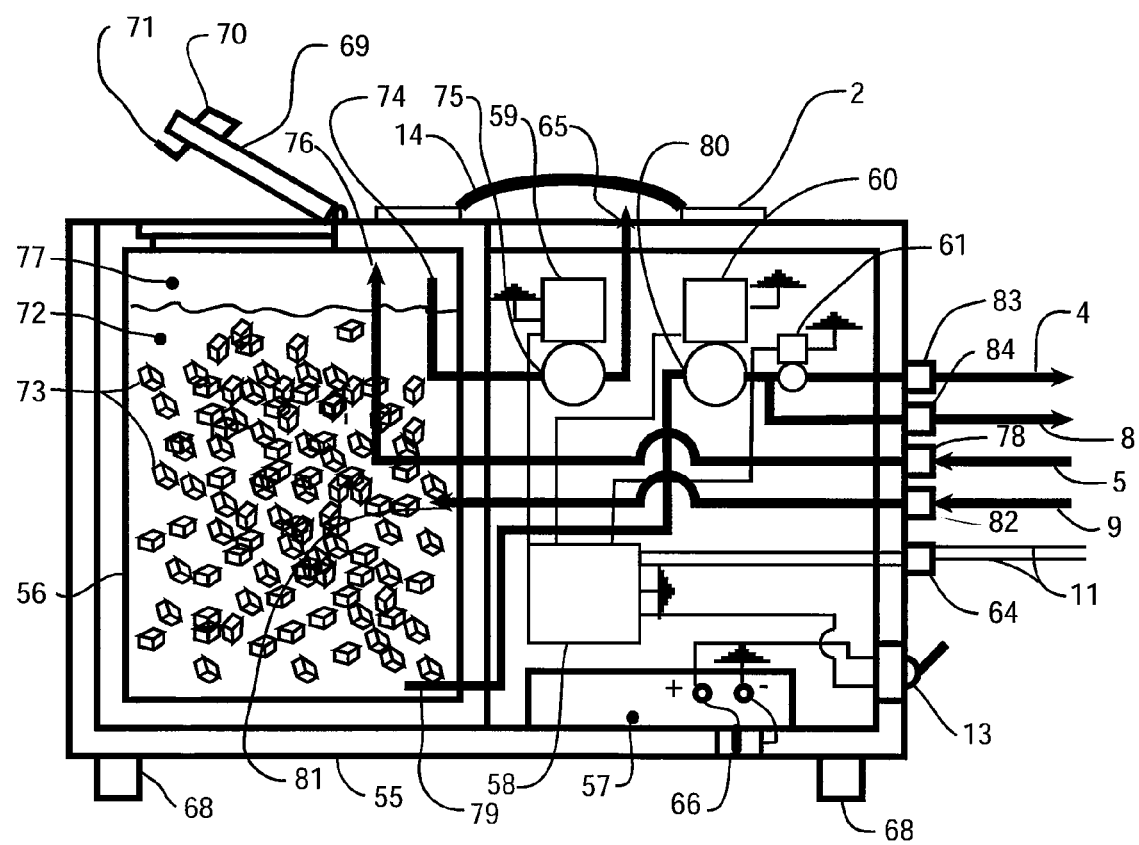
FIG. 11A depicts a schematic of a console, according to one embodiment of the invention.

FIG. 11A depicts, in schematic form, an arrangement of the console 2. The console 2 has a case or housing 55, reservoir 56, battery 57, a controller (e.g., such as a processor and memory) or mother board 58, negative gage pressure source (e.g., aspiration pump) 59, positive gage pressure source (e.g., fluid infusion pump) 60, fluid control valve 61, on/off switch 13, fluid tube connectors 78, 82, 83, & 84, temperature sensor connector 64, aspiration pump outlet 65, and battery recharger receptacle 66.

In one arrangement, the console case 55 has a molded plastic structure that mechanically integrates all system components described above into a single small portable unit as shown. Console case includes carrying handle 14, and feet 68. Carrying case 55 may be fabricated from molded plastic, sheet metal, or a combination of molded plastic and sheet metal. The console 2, in one arrangement is sized (e.g., has dimensions) and has a weight that provides portability to the console 2 and allows a user, such as an emergency medical technician, to transport the console 2 to a patient at risk of ischemic injury (e.g., a patient with cardiac arrest, a patient with acute myocardial infarction, a patient with brain trauma, or a patient with stroke) and provide hypothermia therapy to the patient prior to the patient's arrival at a hospital.

In one arrangement, the reservoir 56 is a sealable, insulated compartment within carrying case 55. In one arrangement, the reservoir 56 is removable from the console 2. For example, the reservoir 56 has a volume of approximately two US gallons. Access door 69 including latch 70, and water/air tight seal 71 provide a means for filling the reservoir 56 with cooling fluid (e.g., saline 72 and brine ice 73) prior to use, and draining the reservoir 56 once hypothermia therapy is completed. Access door 69 is closed thereby sealing reservoir 56 during operation of the system. Reservoir 56 includes fluid vacuum tube 74 which provides a fluid conduit between the air space 77 at the top of reservoir 56 and suction port 75 of aspiration pump 59, reservoir aspiration tube 76 provides a fluid conduit from the air space 77 at the top of reservoir 56 to aspiration tube coupling 78, suction tube 79 provides a fluid conduit from the bottom of reservoir 56 to low pressure port 80 of fluid infusion pump 60, and fluid return tube 81 which provides a fluid conduit between reservoir 56 and fluid outlet tube coupling 82.

The negative gage pressure source (e.g., aspiration pump) 59, for example, is a centrifugal air pump and pumps air from air space 77 in reservoir 56 out of carrying case 55 through air vent 65 as shown thereby causing a partial vacuum in air space 77. In one arrangement the aspiration channel 21 is in fluid communication, via aspiration tube 5, with the air space 77 having the vacuum. In such a configuration, the vacuum creates the negative gage pressure within the aspiration channel 21.

The aspiration pump 59 has a power of approximately ¹/₂₀ to ⅓ of a horsepower. In one arrangement the infusion pump 60 is a positive displacement liquid pump, such as a vane pump. Infusion pump 60 pumps saline from reservoir 56 to fluid infusion tube coupling 83 through fluid flow control valve 61 and to fluid inlet tube coupling 84 under a positive gage pressure between approximately 10 and 25 PSI. The pressure of the fluid supplied to fluid infusion tube coupling 83 and fluid inlet tube coupling 84 can be controlled by adjusting the speed of the motor of infusion pump 60 by motherboard 58 or by a pressure relief/bypass valve (not shown).

In one arrangement, the fluid flow control valve 60 controls the flow of fluid from console 2 to head-cooling device 1 in an on/off manner. Fluid flow control valve 61 can be a solenoid actuated liquid valve. In one arrangement, motherboard (e.g., controller) 58 has electronic circuits that control the operation of all electrical components of the system by embedded hardware or software logic. A predetermined therapeutic body temperature can be embedded into the control logic of the motherboard 58, or can be set by the user by a user control setting on the console 2 (not shown). The motherboard 58 can also receive signals from other system sensors to provide safety interlocks, or to provide additional therapeutic functional controls. Temperature sensor connector 64 provides a removable connection between body temperature sensor lead 11 and console 1. Fluid couplings 78, 82, 83, and 84 include a receptacle mounted on carrying case 55, and a plug mounted on corresponding fluid tube. The receptacle and the plug of each coupling contain a valve such that when the plug and the receptacle are not coupled the valve in the receptacle and the valve in the plugs close preventing fluid from escaping from the console 1 through the receptacle, or from the fluid tube trough the plug. There are several lines of such valved couplings commercially available. Battery 57 is rechargeable through an external power adapter (not shown) that may be connected to the console 2 by receptacle 66.

In one arrangement, the cooling system 100 functions as described below. The head-cooling device 1, body-cooling device 6, and temperature sensor 10 are placed on a patient. The fluid tubes 4, 5, 8, and 9 and temperature sensor lead 11 are connected to console 2. The reservoir 56 is filled with cooling fluid, such as approximately 10 pounds of brine ice 73 and two quarts of saline 72 or equivalent amounts of ice and water. Access door 69 is shut and sealed using latch mechanism 70. The on/off switch 13 is positioned to the "on" position which causes the motherboard 58 to open fluid control valve 61 and activate aspiration pump 59 and fluid infusion pump 60. Aspiration pump 59 causes a partial vacuum in air space 77 resulting in a vacuum in aspiration channel 21 of head-cooling device 1 which therefore results in fluid return from head-cooling device to reservoir 56 as previously described. Simultaneously, fluid infusion pump 60 is supplying cold saline 72 to head-cooling device 1 and body-cooling device 6 under pressure. Fluid returns from the body-cooling device 6 to reservoir 56 passively by means shown.

Once the patient's body temperature reaches the predetermined temperature as sensed by body temperature sensor 10, motherboard 58 closes fluid control valve 61 thereby stopping the flow of cold saline to head-cooling device 1 and the flow of cold saline is continued to body-cooling device 6. Body temperature is maintained at predetermined temperature according to body temperature sensor 10 by modulating the speed of the motor of infusion pump 60, or by modulating infusion pump 60 "on" or "off" to control body temperature. Head-cooling device 1 may be removed from the patient once the predetermined body temperature is reached. Ice is replenished in reservoir 56 as required. Console may be plugged into a wall outlet using an AC adapter (not shown) once the patient reaches the hospital and run indefinitely. Once the therapy is completed the on/off switch 13 is moved to the "off" position, and body-cooling device 6 and head-cooling device 1 is removed from the patient.

During operation, the positive gage pressure source (e.g., fluid infusion pump) 60 supplies cooling fluid from the cooling fluid reservoir 56 to the head-cooling device 1 under positive gage pressure. The negative gage pressure source (e.g., aspiration pump) 59 scavenges cooling fluid from the head-cooling device 1 (e.g., via cooling fluid wicking through the patient's hair and into the aspiration channel 21). The controller 58 receives temperature signals from the body temperature sensor (e.g., via the temperature sensor connector 64). Based upon the temperature signals, the controller 58

(e.g., a temperature control circuit associated with the controller) adjusts the positive gage pressure source 60, negative gage pressure source 59, or the cooling fluid flow control valve 61 to increase or decrease the amount of cooling fluid provided to the patient and thereby control cooling of the patient.

Figure 11B:
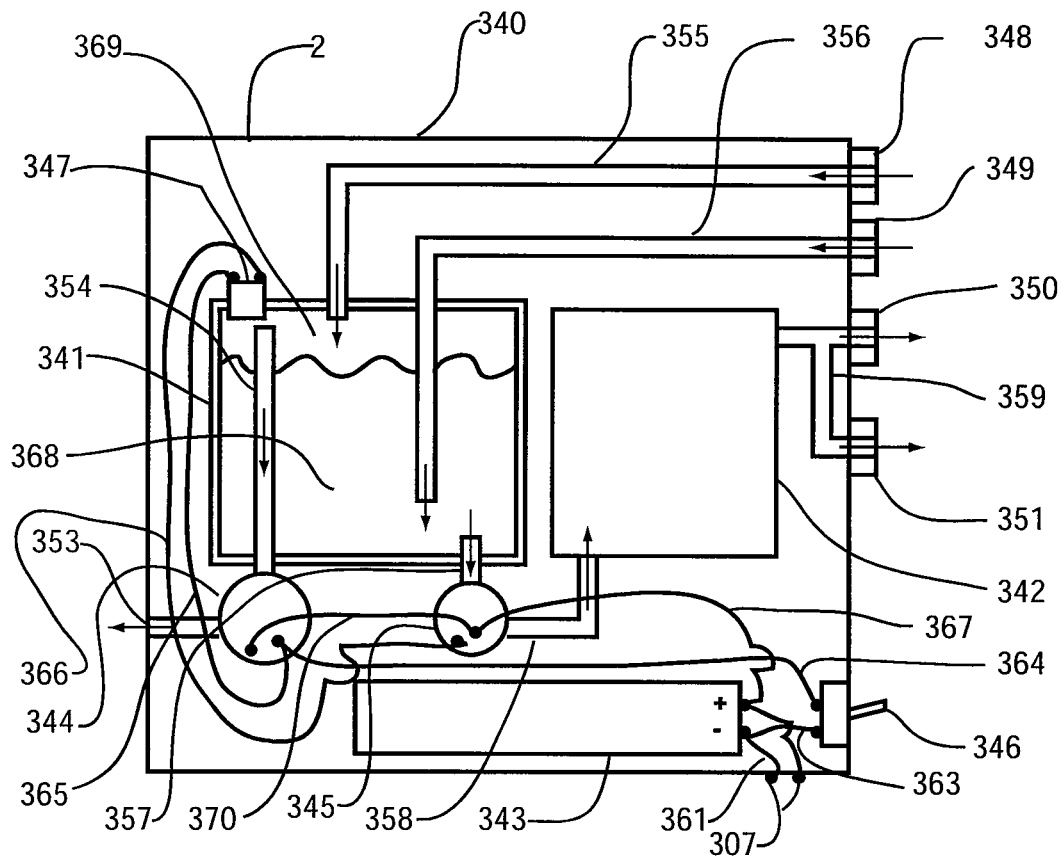
FIG. 11B depicts a schematic of the console, according to another embodiment of the invention.

FIG. 11B depicts another arrangement of the console 2 in schematic form. The console 2 has a housing or case 340 that has a cooling fluid reservoir 341, thermal battery 342, electrical battery 343, air pump 344, water pump 345, on/off switch 346, pressure switch 347, head-cooling device aspiration tube receptacle 348, body-cooling device fluid return tube receptacle 349, cooling cap fluid inlet tube receptacle 350, body-cooling device fluid inlet tube receptacle 351, air vent 353, vacuum tube 354, aspiration tube 355, fluid tubes 356, 357, 358, 359 and 360, wires 361, 362, 363, 364, 365, 366, and 367, and 369, and electrical contacts 37.

The reservoir 341 is air-tight and, in one arrangement, contains a cooling fluid, such as saline 368, and air 369. The air pump 344, when activated, pumps air 369 from reservoir 341, through vacuum tube 354, out of case 340 trough air vent 353 which creates a pressure within reservoir 341 below atmospheric pressure. The water pump 345, when activated, pumps saline 368 from reservoir 341, through thermal battery 342, to head-cooling device 1 and body-cooling device 6 and back to reservoir 341 through aspiration tube 355, and fluid tube 356. Thermal battery 342 removes heat from the saline 368 as the saline 368 traverses through the thermal battery 342, thereby lowering or reducing the temperature of the saline 368 (e.g., cooling fluid). The electrical battery 343 provides electrical power to air pump 344 and water pump 345, and may be recharged by an external charging source through electrical contacts 307 mounted on the external surface of the console case 340.

In one arrangement, the air pump 344 aspirates the head-cooling device 1 (e.g., the aspiration channel 21) and the water pump 345 supplies saline 368 under pressure to the head-cooling device 1 and body-cooling device 6. The thermal battery 342 is configured to cool the saline 368 during operation. The cooling cap aspiration tube receptacle 348 is mounted on console case 340, and provides removable connection of the cooling fluid aspiration tube 5 to the console 2. The body-cooling device fluid return tube receptacle 349 is coupled to the console case 340 and provides removable connection of the cooling fluid outlet tube 9 to the console 2. The cooling cap fluid inlet tube receptacle 350 is mounted on console case 340 and provides removable connection of cooling cap 1 a cooling fluid infusion tube 4 to console 2. The body-cooling device fluid tube receptacle 351 is mounted on console case 340 and provides removable connection of the cooling fluid inlet tube 8 to console 2. Receptacles 348, 349, 350 and 351 provide a valve mechanism where when a respective tube is connected to receptacle, fluid communication is provided between the tube and the receptacle, and where if a tube is not connected to the receptacle, a valve within the receptacle closes and prevents fluid communication outside of console 2.

Fluid tube 355 provides fluid communication between cooling cap aspiration tube receptacle 348 and reservoir 341, as shown. Fluid tube 356 provides fluid communication between cooling collar fluid return tube receptacle 349 and reservoir 341 as shown. Fluid tube 357 provides fluid communication between reservoir 341 and water pump 345 as shown. Fluid tube 358 provides fluid communication between water pump 345 and thermal battery 342 as shown. Bifurcated fluid tube 359 provides fluid communication between thermal battery 342 and cooling cap fluid inlet tube receptacle 50 and cooling collar fluid inlet tube receptacle 51 as shown. Wire 361 connects the negative terminal of electrical battery 343 to a first recharging contact 307. Wire 362 connects positive terminal of electrical battery 343 to a second recharging contact 307. Wire 63 connects positive terminal of battery 343 to one terminal of on/off switch 346. Wire 364 connects the second terminal of on/off switch 346 to positive terminal of air pump 344. Wire 365 connects positive terminal of air pump 344 to one terminal of pressure switch 347. Wire 366 connects second terminal of pressure switch 347 to positive terminal of water pump 345. Wire 367 connects negative terminal of water pump 345 to negative terminal of battery 343. Wire 370 connects negative terminal of air pump 344 to negative terminal of water pump 345.

During operation of the body cooling system 100 using the console 2 of FIG. 11B, a user fits a head-cooling device 1 and a body cooling device 6 is fitted to a patient. The user connects the umbillicals 3,7 of the head-cooling device 1 and body-cooling cooling to receptacles 348, 349, 350 and 351. The user places the on/off switch 346 into the "on" position to activate the air pump 44. The pressure switch 347 moves from the normally open position to the closed position and activates water pump 345 once pressure within reservoir 341 is reduced by operation of air pump 344 to a preset pressure of between approximately 1 to 10 PSI below atmospheric pressure. If pressure within reservoir 341 rises above the preset pressure stated above, pressure switch 347 moves from the closed position to the normally open position and deactivates water pump 45. The user moves the on/off switch 346 to the off position once hypothermia therapy is concluded and removes the cooling cap 1 and body cooling device 8 from the patient.

Figure 11C:
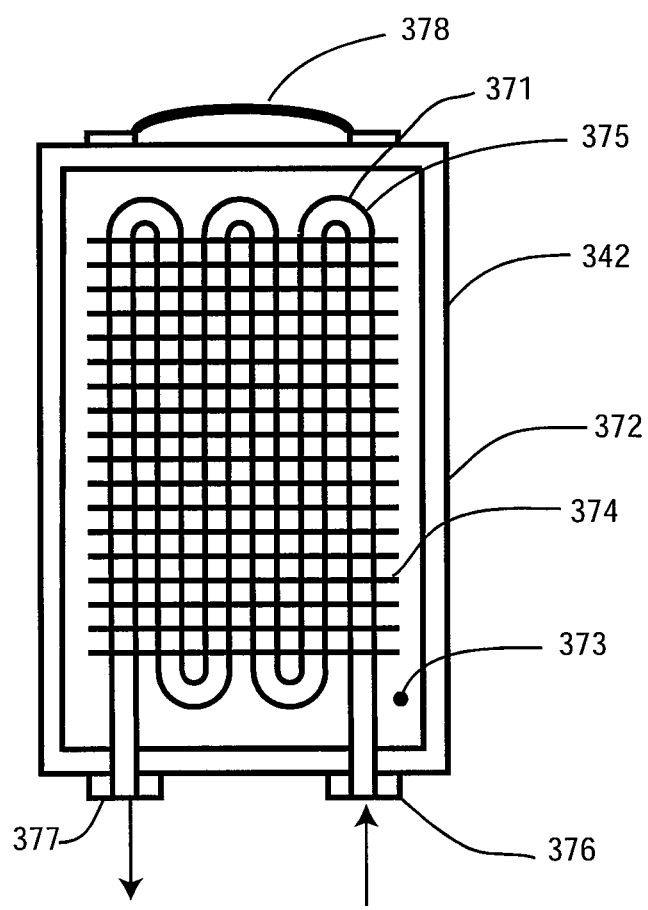
FIG. 11C depicts a sectional view of a thermal battery, according to one embodiment of the invention.

FIG. 11C depicts an arrangement of the thermal battery 342 of FIG. 11B. The thermal battery 342 has a housing 372, heat exchanger 371 having a heat exchanger tube 375 and, optionally, heat exchanger fins 374, a fluid inlet fitting 376, a fluid outlet fitting 377, cooling medium 373, and a handle 378. The housing 372 contains heat exchanger 371 and cooling medium 373 and, in one arrangement, is molded from a polymer such as high-density polyethylene. Cooling medium 373, in one arrangement, is a liquid solution or water having the property of freezing and melting at a constant temperature. Heat exchanger 371 consists of a length of heat exchanger tube 375 which provides a fluid path for saline 368 internal to housing 732 where heat exchanger tube 375 is surrounded by and in thermal contact with cooling medium 373. In one arrangement, the heat exchanger tube 375 is constructed from stainless steel tubing having an inner diameter between approximately 0.25 inches and 0.5 inches and a wall thickness between approximately 0.005 and 0.020 inches. The shape heat exchanger tube 375 may be serpentine as shown or some other shape. The straight-line length of heat exchanger tube 375 is between 12 inches and 120 inches. Metal heat exchanger fins 374 may be bonded to heat exchanger tube 375 to enhance heat transfer from cooling medium 373 to saline 368 as it passes through heat exchanger tube 375. Housing 372 is constructed so that thermal battery 342 functions as a cassette and may be placed into, and removed from console 2. Console 2 is designed to receive thermal battery 342 as a cassette and is configured to provide easy user access to thermal battery 342 and is configured to provide thermal insulation to thermal battery 342 to prevent absorption of ambient heat. Fluid inlet fitting 376, and fluid outlet fitting 377, provide fluid connection to console 2 and mate with receptacles in console 2. Handle 378 facilitates placement and removal of thermal battery 342 from console 2.

In one arrangement, a user charges the thermal battery 342 by placing the thermal battery 342 into a freezer for a period of time sufficient to convert cooling medium 373 from a liquid state to a solid state. Cooling medium 373 reverts back to a liquid state during use in patient cooling by absorbing heat from the patients body as transferred to the thermal battery 342 by circulation of saline 368 as previously described. In one arrangement, the cooling medium 373 is formulated to freeze and melt at a temperature between approximately −15 and +10 degrees centigrade. Cooling medium 373, for example, is a solution of salt water, a solution of water and another substance, or is water. In one arrangement, the thermal battery 342 contains between 1 and 10 pounds of cooling medium 373, and provides for patient cooling for a duration of between approximately 15 and 240 minutes.

Figure 11D:
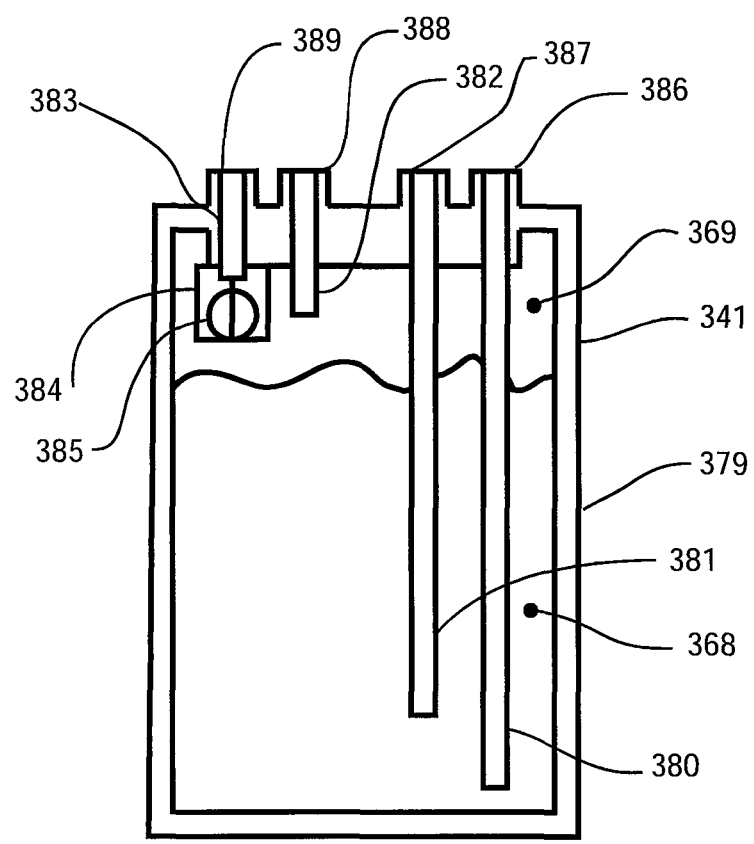
FIG. 11D depicts a sectional view of a fluid reservoir.

FIG. 11D depicts an arrangement of the reservoir 341 of FIG. 11B. The reservoir 341 has a housing 79, containing saline 368 and air 369, fluid outlet pipe 380, fluid return pipe 381, aspiration pipe 382, vacuum pipe 383, cage 384, ball 385, fluid outlet pipe fitting 386, fluid return pipe fitting 387, aspiration pipe fitting 388, and vacuum pipe fitting 389. Housing 379 is molded from a suitable polymer, such as high-density polyethylene, and has a fluid capacity of 1 to 4 liters. Fluid outlet pipe 380 and fluid outlet pipe fitting 386 provides connection to the low-pressure side of water pump 345 and is analogous to fluid tube 357. Fluid return pipe 381 and fluid return pipe fitting 387 provide connection to cooling collar fluid return tube receptacle 349 and is analogous to fluid tube 356. Aspiration pipe 382 and aspiration pipe fitting 388 provides connection to cooling cap aspiration tube receptacle 348 and is analogous to fluid tube 355. Vacuum pipe 383 and vacuum pipe fitting 389 provide connection to the low pressure side of air pump 44 and is analogous to vacuum tube 354. Ball 384 is buoyant in water and is held in close proximity of the internal end of vacuum pipe 383 by cage 385. Ball 384 and cage 385 function as a valve to prevent any saline from being drawn into vacuum tube 383 in the event the reservoir 341 does not remain upright as shown. Housing 379 is constructed so that reservoir 341 functions as a cassette and may be placed into, and removed from console 2. Console 2 is designed to receive reservoir 341 as a cassette and is configured to provide easy user access to reservoir 341, and is configured to provide thermal insulation to reservoir 41 prevent absorption of ambient heat. Connection of the reservoir 341 to apparatus contained in console 2 as described above is provided by a receptacle (not shown) that is integral with console 2.

FIG. 12 depicts another arrangement of the head-cooling device 1 (e.g., tissue cooling device). Head-cooling device 1 includes a tissue covering portion or head cap 15, chinstrap 12, cooling fluid infusion tube 4, infusion manifold 16, air manifold 17, and air tube 5. Head cap 15 may be either a rigid structure molded from thermoplastic such as nylon, vinyl, or polycarbonate, or may be a flexible structure molded from an elastomer such as silicone rubber. Chinstrap 12 holds head-cooling device 1 to the patient's head 29.

Cooling fluid enters head-cooling device 1 through cooling fluid infusion tube 4 and infusion manifold 16 under positive gage pressure between approximately 0.2 and 40 PSI. Cooling fluid exits head-cooling device 1 by a fluid outlet 130 in communication with the cap 15 and in fluid communication with the fluid circulation space 25. For example, in one arrangement, the fluid outlet 130 includes a fluid return manifold 134 and a cooling fluid return tube 132. The fluid outlet 130 is configured to allow egress of the cooling fluid from the fluid circulation space 25. For example, in one arrangement, the fluid outlet 130 allows the cooling fluid to exit the fluid circulation space 25 under a positive gage pressure between approximately 0.2 and 2 PSI. A check valve 136 (e.g., as illustrated in FIG. 13) forms part of the fluid return manifold 134 and operates to maintain a positive gage pressure within head-cooling device 1 (e.g., within the fluid circulation space 25) so that a siphoning effect, and resulting negative gage pressure within head-cooling device 1 is prevented.

Figure 13:
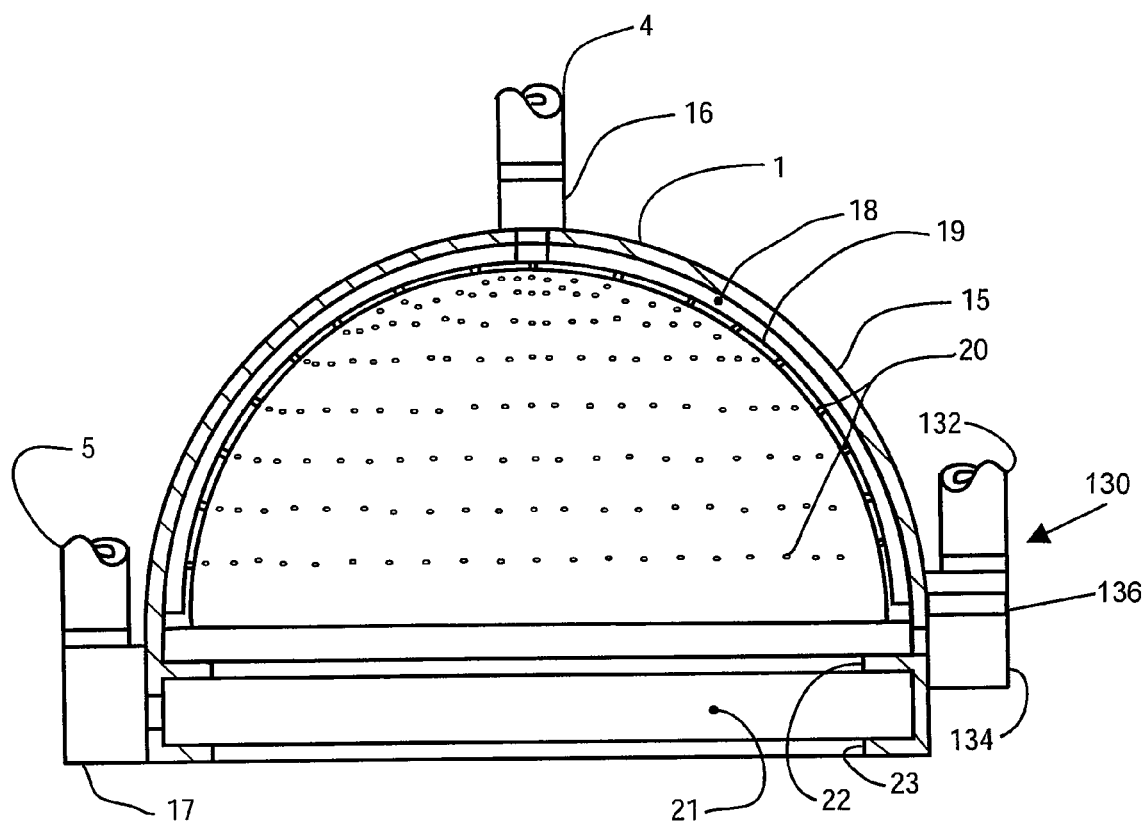
FIG. 13 depicts a sectional view of the head-cooling device of FIG. 12, according to one embodiment of the invention.

FIG. 13 depicts, in sectional view, the construction of head cap 15 of head-cooling device 1. Head cap 15 has inner wall 19, outer wall 24, fluid channels 18 formed between inner wall 19 and outer wall 24, fluid jets 20 formed in inner wall 19 over fluid channels 18, channel 21 formed by inner seal 22 and outer seal 23 and outer wall 24. Infusion manifold 16 is bonded to head cap 15 or may be integrally molded into head cap 15. Infusion manifold 16 provides fluid communication between cooling fluid infusion tube 4 and fluid channels 18. Fluid return manifold 134 is bonded to head cap 15 or may be integrally molded into head cap 15. Fluid return manifold 134 provides fluid communication between cooling fluid return tube 132 and fluid circulation space 25 (see FIG. 14). Air manifold 17 is bonded to head cap 15 or may be integrally molded into head cap 15. Air manifold 17 provides fluid communication between air tube 5 and channel 21 (see FIGS. 13 & 14).

Figure 14:
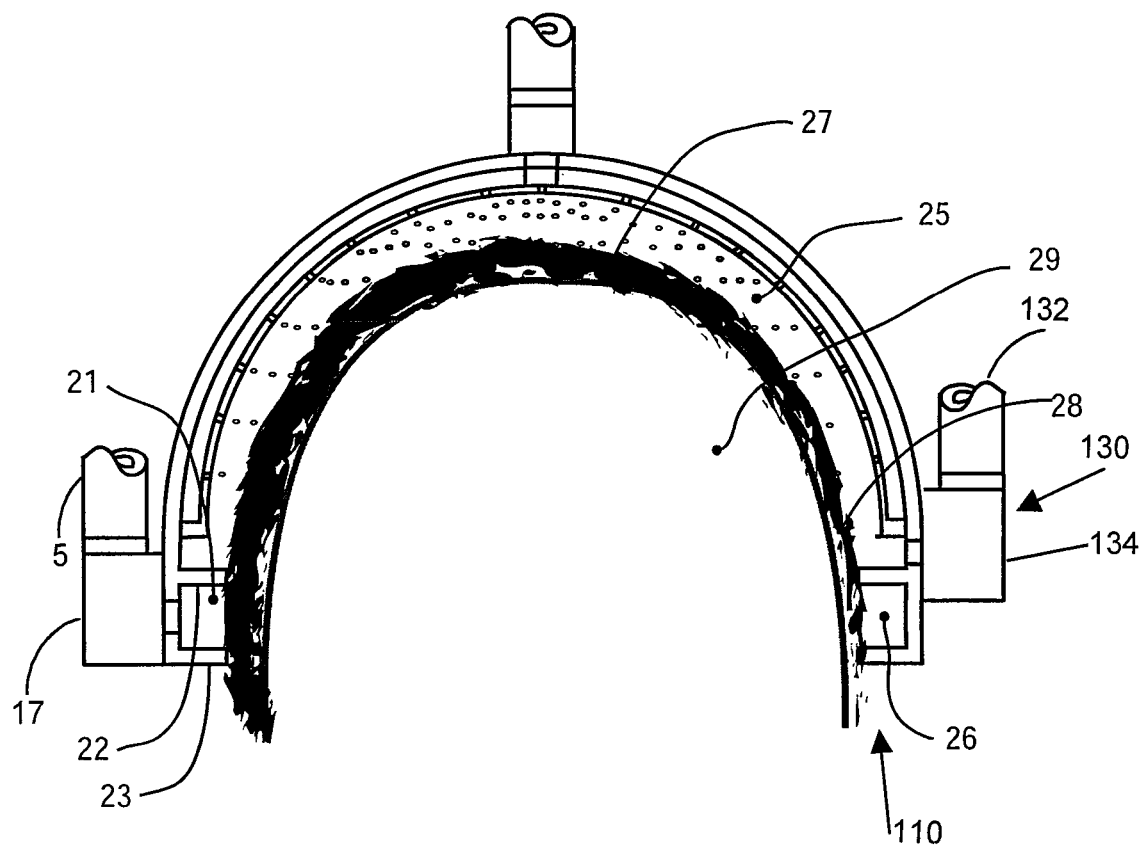
FIG. 14 depicts the head-cooling device of FIG. 12 in sectional view mounted on the head of a patient, according to one embodiment of the invention.

FIG. 14 depicts in sectional view the head-cooling device mounted on the head of a patient showing the cooling fluid circulation space 25, air space 26, and the functional relationship between the cooling fluid circulation space 25 and the air space 26. Cooling fluid circulation space 25 includes the volumetric space between inner wall 19, patient's scalp 28, and inner seal 22, and includes the volumetric space occupied by the patient's hair 27 within the just defined cooling fluid circulation space 25. The air space 26 includes the volumetric space between the patient's scalp 28 and channel 21 comprising inner seal 22, outer seal 23 and outer wall 24, and is maintained at a higher gage pressure than fluid in circulation space 25. Channel 21 is molded from an elastomer material such as silicone rubber.

In one arrangement, during operation, the air manifold 17 connects, via air tube 5, to a positive gage pressure source that, in one arrangement, provides pressurized air to the channel 21. The pressure within the channel 21 is greater than the pressure within the fluid circulation space 25, thereby sealing the rim 110 of the cap 15 to the patient's head. Inner seal 22 is configured by geometry and material selection to resist the flow of pressurized air from channel 21 through the hair 27 into fluid circulation space 26 such that pressurized air in channel 21 remains at a higher gage pressure than fluid in circulation space 25. Since air in channel 21 is at a higher gage pressure than fluid in circulation space 25, fluid in circulation space 25 is prevented from exiting fluid circulation space 25 through inner seal 22. Outer seal 23 is configured by geometry and material selection to resist the flow of air through the hair 27 from inside channel 21 such that pressure within aspiration channel is maintained at a positive gage pressure between approximately 0.2 and 10 PSI by an air pressurization source (e.g., positive gage pressure source) provided by console 2. Cooling fluid is scavenged from the head cap 15 through fluid return tube 132 provided that the pressure within channel 21 remains at a positive gage pressure greater than the gage pressure within fluid circulation space 25.

Figure 15:
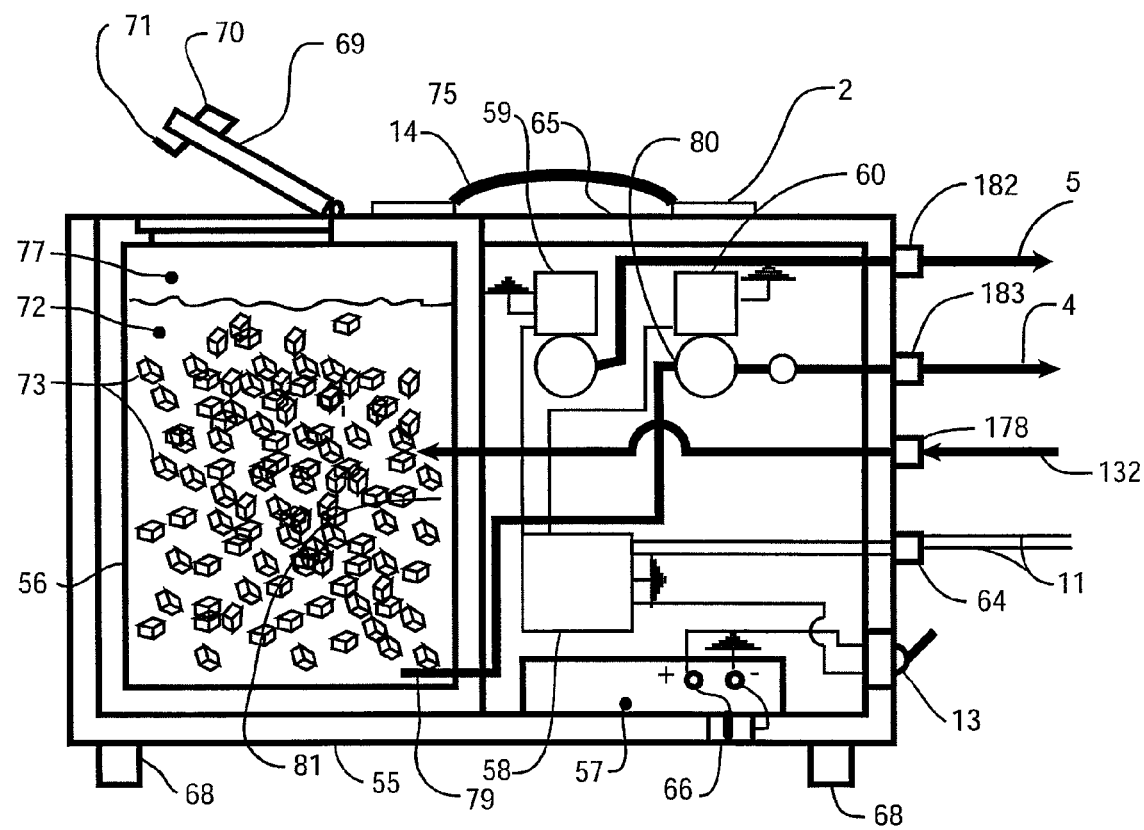
FIG. 15 depicts a schematic of a console, according to another embodiment of the invention.

FIG. 15 depicts in schematic form, an arrangement of the portable console 2 for use with the cooling device illustrated in FIGS. 12-14. The portable console 2 has a housing or console case 55, reservoir 56, battery 57, mother board 58, compressor 59, fluid infusion pump 60, on/off switch 13, fluid tube connectors 178 and 183, air tube connector 182, temperature sensor connector 64, and battery recharger receptacle 66. Fluid couplings 178, 182, and 183 comprise a receptacle mounted on carrying case 55, and a plug mounted on corresponding fluid tubes 132, 5, and 4.

A vent (not shown) is provided within the reservoir so that reservoir 56 remains at ambient pressure at all times. Suction tube 79 provides a fluid conduit from the bottom of reservoir 56 to low pressure port 80 of fluid infusion pump 60, and fluid return tube 81 which provides a fluid conduit between reservoir 56 and fluid return tube coupling 78. Compressor 59 may be a centrifugal air pump and pumps air under positive pressure to channel 21 (FIGS. 13 & 14). Compressor 59 has a power of approximately ½0 to ⅓ of a horsepower. Infusion pump 60 is a positive displacement liquid pump, such as a vane pump.

During operation, the infusion pump 60 pumps a cooling fluid from reservoir 56 to fluid inlet tube coupling 183 under a positive gage pressure between approximately 2 and 25 PSI. The pressure of the fluid supplied to fluid infusion tube coupling 183 can be controlled by adjusting the speed of the motor of infusion pump 60 by motherboard 58 or can be controlled by a pressure relief/bypass valve (not shown). A positive gage pressure pump 80, such as an air pump, provides air to the channel 21 via connector 183 and tube 4 to pressurize the channel 21 and seal the cap 15 to the patient's head. Also during operation, fluid returns to the console 2 from the fluid circulation space 25, defined by the head-cooling device 1, via the fluid return tube 132. For example, in one arrangement, the cooling fluid exits the head-cooling device 1 when the pressure within the fluid circulation space 25 causes the valve 136 within the fluid return manifold 134 to open. In another arrangement, the fluid exits the head-cooling device 1 and returns to the console 2 via gravity (e.g., a gravity feed system).

Returning to FIGS. 12-14, in one arrangement, during operation, the air manifold 17 connects, via air tube 5, to a negative gage pressure source that removes air from the channel 21. During operation, the pressure within the channel 21 (e.g., aspiration channel) is less than the pressure within the fluid circulation space 25, thereby sealing the rim 110 of the cap 15 to the patient's head. Such sealing maintains the cooling fluid within the fluid circulation space 25 and minimizes leakage of the fluid past the rim 110 of the cap 15. In such a configuration, cooling fluid exits the head cap 15 through fluid outlet 130 and fluid return tube 132.

Figure 16:
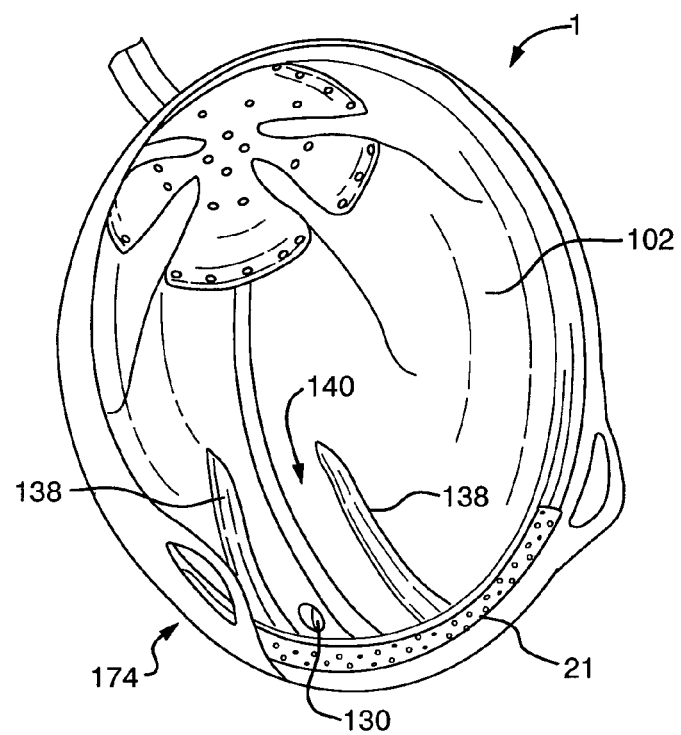
FIG. 16 illustrates a perspective view of the head-cooling device of FIG. 12, according to one embodiment of the invention.

FIG. 16 illustrates an arrangement of the head-cooling device 1 illustrated in FIGS. 12-14. The head-cooling device 1 has head supports or protrusions 138 disposed on the inner surface 102 of the cap 15. The protrusions 138 are configured to contact the back of a patient's head to separate the patient's head from a back portion 174 of the head-cooling device 1. The head supports 138, therefore, define a fluid collection reservoir 140 in fluid communication with the fluid circulation space 25. During operation, in one arrangement, the fluid collection reservoir 140 acts as a sink for cooling fluid pumped into the fluid circulation space 25 and directs the cooling fluid to the second fluid outlet 130. In one arrangement, the cooling fluid exits the fluid collection reservoir 140, via the second fluid outlet 130, under a positive gage pressure. In another arrangement, the second fluid outlet 130 is open to the atmosphere, thereby allowing removal of the cooling fluid from the fluid collection reservoir 140 via gravity (e.g., a gravity feed).

Figure 17:
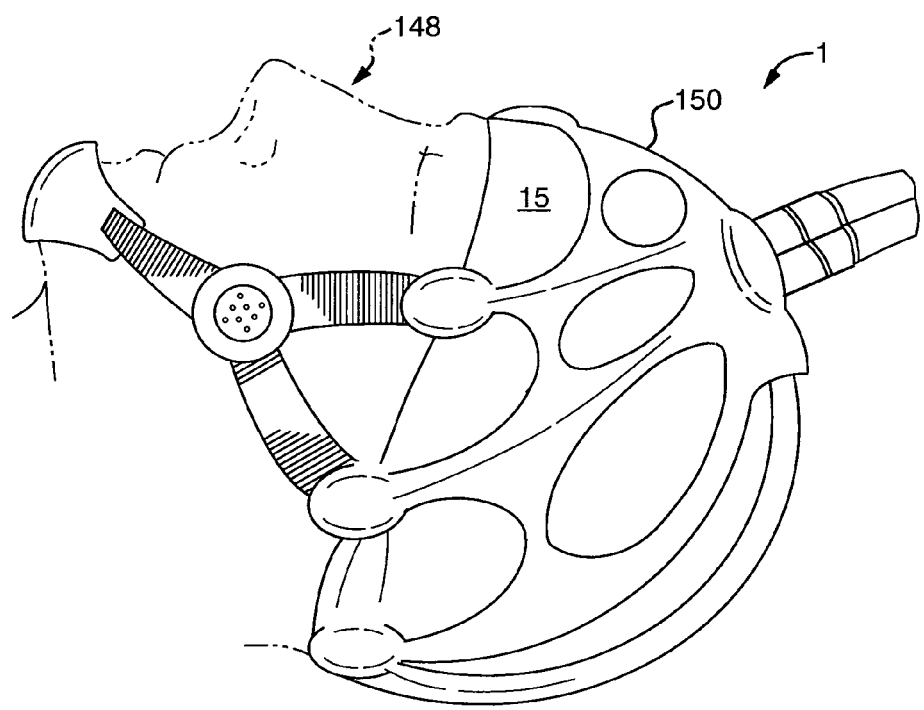
FIG. 17 illustrates the head-cooling device having a rigid outer shell, according to one embodiment of the invention.

FIG. 17 illustrates one arrangement of the head-cooling device 1 where the cap 15 is formed of a flexible material and includes a substantially rigid shell 150 coupled to the outer surface 104 of the cap 15. For example, the rigid shell 150 is formed of a polyethylene (PET) plastic material. During operation the positive gage pressure source of the console 2 provides cooling fluid to the head-cooling device 1 and aids in maintaining the pressure within the fluid circulation space 25 between approximately 0.1 and 10 PSI. Also during operation, the negative gage pressure source of the console 2 removes air from within the aspiration channel 21 and maintains the pressure within the aspiration channel 21 between approximately −0.1 and −10 PSI. In certain cases, the pressure within the fluid circulation space 25 causes the cap 15 (e.g. the portion of the cap 15 defining the fluid circulation space 25) to expand or "balloon" relative to a head 148 of the patient. The rigid shell 150 minimizes expansion of the cap 15 during operation, thereby limiting the potential for the fluid circulation space 25 to break the seal formed by the aspiration channel 21 and cause fluid to leak from the cap 15.

Figure 18:
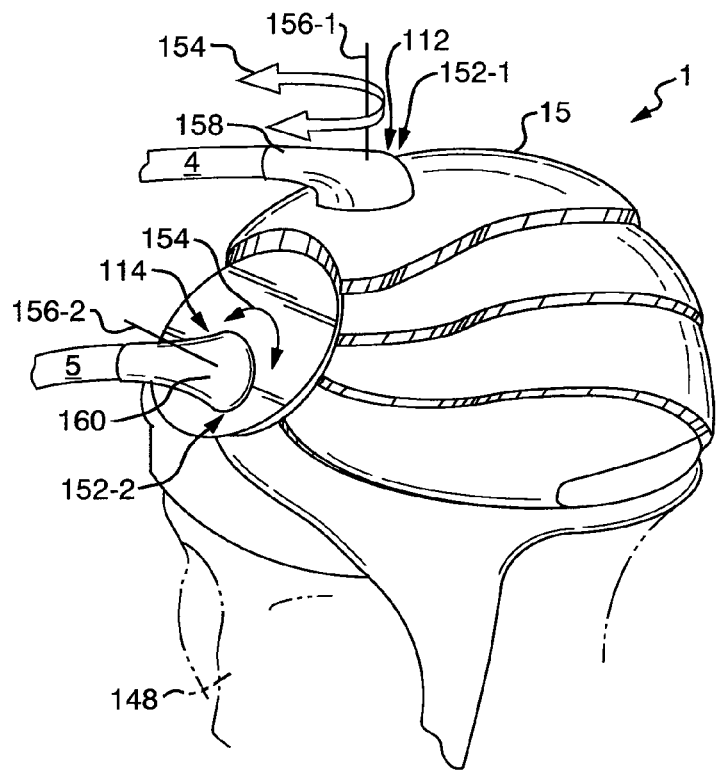
FIG. 18 illustrates the head-cooling device having an inlet swivel joint, according to one embodiment of the invention.

FIG. 18 illustrates an arrangement of the head-cooling device 1 where the fluid inlet 112 and the fluid outlet 114 of the head-cooling device 1 are configured to include swivel joints 152. For example, the fluid inlet 112 includes inlet swivel joint 152-1 and the fluid outlet 114 includes outlet swivel joint 152-2. The inlet swivel joint 152-1 allows rotation 154 of the inlet connector 158 (e.g., connected to the respective cooling fluid infusion tube 4) relative to an axis 156-1 substantially perpendicular to the outer surface 104 of the head-cooling device 1. The outlet swivel joint 152-2 allows rotation 154 of the outlet connector 160 (e.g., connected to the respective cooling fluid aspiration tube 5) relative to an axis 156-2 substantially perpendicular to the outer surface 104 of the cap 15. The swivel joints 152-1, 152-2 allow positioning of the head-cooling device 1 at various locations or orientations relative to the console 2 while minimizing strain on, or bending and kinking of, the tubes 4, 5. For example, when a user positions the head-cooling device 1 relative to the console 2, the swivel joints 152 allow the connectors 158, 160 and associated tubes 4, 5 to rotate relative to the head-cooling device 1.

Figure 19:
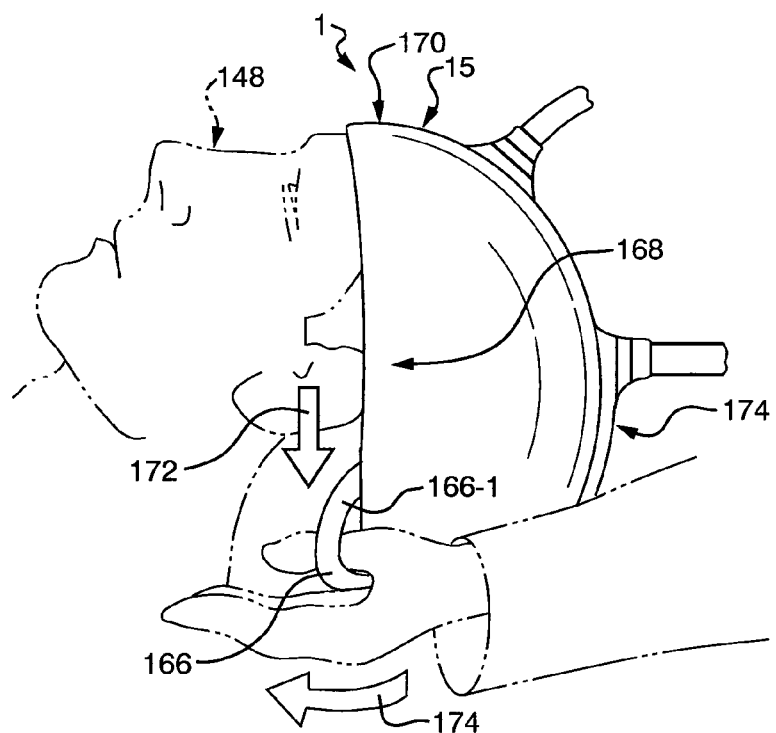
FIG. 19 illustrates the head-cooling device having handles, according to one embodiment of the invention.

FIG. 19 illustrates an arrangement of the head-cooling device 1 where the cap 15 has handles 166 integrally formed with the cap 15. In one arrangement, the cap 15 has a first handle 166-1 oriented on a first side 168 of the head-cooling device 1 and a second handle (not shown) oriented on a second side of the head-cooling device 1 (e.g., opposing the first side 168 of the head-cooling device 1). The handles 166 allow a user (e.g., an emergency medical technician) to grasp the head-cooling device 1 and position the head-cooling device 1 onto a patient's head 148. For example, assume the cooling device is formed from a flexible material. During installation, the user inserts his thumbs within the handles 166 and places a front portion 170 of the head-cooling device 1 in contact with a forehead of a patient's head 148. Using the handles 166, the user applies a force in a first direction 172, substantially perpendicular to the front portion 170 of the head-cooling device 1. The user then uses the handles 166 to apply a force in a second direction 174 (e.g., substantially perpendicular to the force applied in the first direction 172) to place a back portion 174 of the head-cooling device 1 in contact with a back of the patient's head 148.

Figure 20:
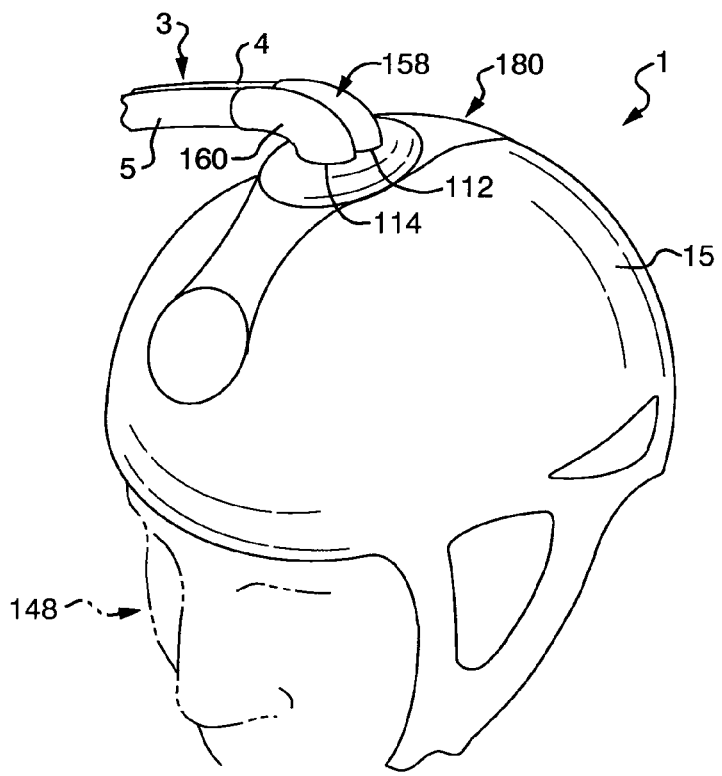
FIG. 20 illustrates the head-cooling device having a fluid inlet positioned in proximity to a fluid outlet, according to one embodiment of the invention.

FIG. 20 illustrates one arrangement of the head-cooling device 1 where the cap 15 is configured such that the fluid inlet 112 is located in proximity to the fluid outlet 114. For example, as shown, both the fluid inlet 112 and the fluid outlet 114 are oriented on a top portion 180 of the cap 15. Such a configuration allows use of a single umbilical 3 having both the cooling fluid infusion tube 4 and the cooling fluid aspiration tube 5 with associated connectors 158, 160. Such a configuration minimizes the need for separate tubes 4, 5 (e.g., attached to the cap 15 in non-proximal locations) to attach the head-cooling device 1 to the console 2, thereby minimizing the amount of time required by the user to initiate hypothermia treatment to a patient at risk for ischemic injury, for example.

Figure 21:
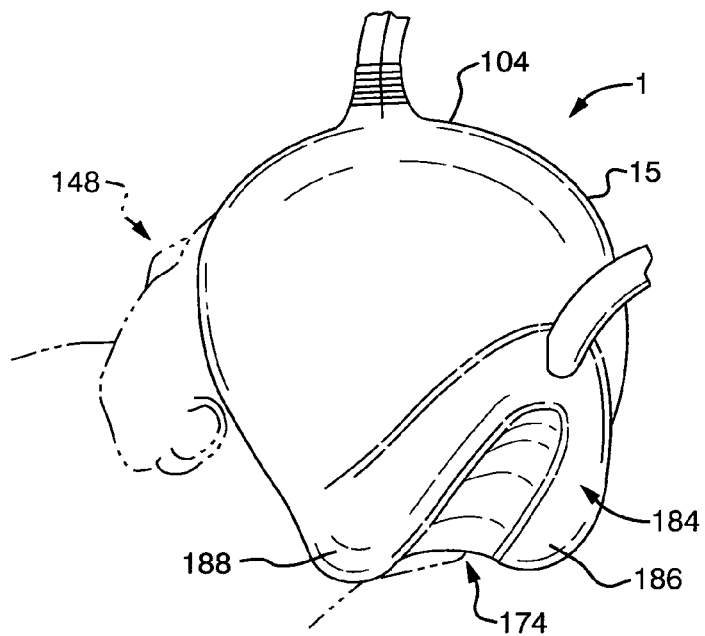
FIG. 21 illustrates a side view of the head-cooling device having a stabilizer mechanism, according to one embodiment of the invention.
Figure 22:
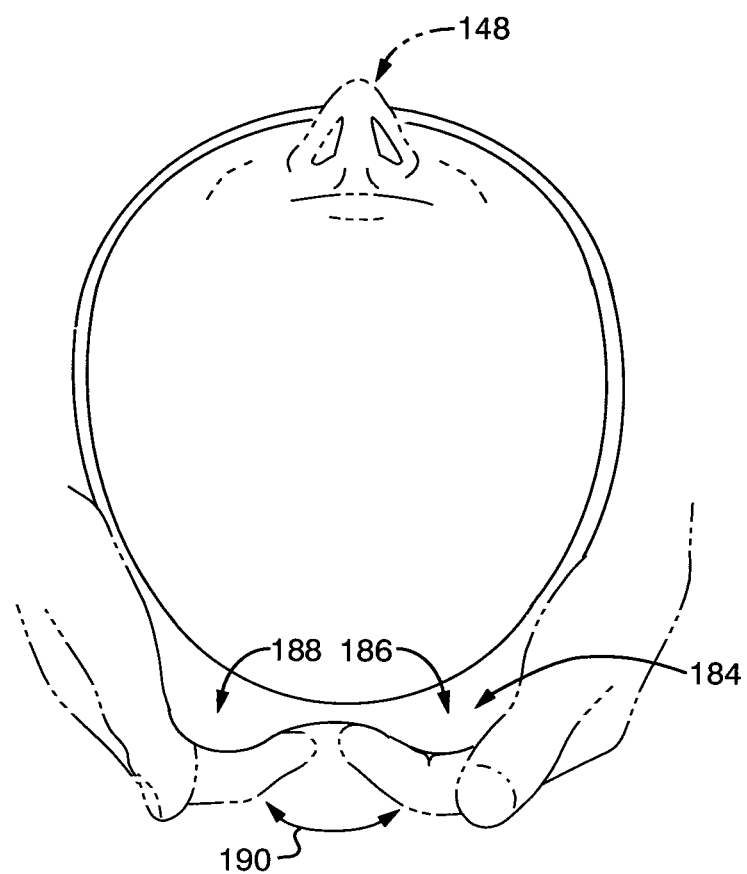
FIG. 22 illustrates the head-cooling device of FIG. 21, according to one embodiment of the invention.

FIGS. 21 and 22 illustrate an arrangement of the head-cooling device 1 where the head-cooling device 1 has a movement stabilizer component 184 located on the outer surface 104 of the cap 15. For example, the movement stabilizer component 184 is integrally formed along a back portion 174 of the cap 15. In one arrangement, the movement stabilizer component 184 has a first stabilizer portion 186 and a second stabilizer portion 188. During operation, after a user places the head-cooling device 1 on the head 148 of a patient, the user places the patient's head 148 onto a resting surface, such as a bed or a table. The first stabilizer portion 186 and the second stabilizer portion 188 of the movement stabilizer component 184 contact the resting surface and minimize rotation of the head 148 during hypothermia treatment. As shown in FIG. 22, the first stabilizer portion 186 and the second stabilizer portion 188 of the movement stabilizer component 184 also provide gripping surfaces for the head-cooling device 1 to allow user adjustment of the patient's head 148. For example, a user grasps the first stabilizer portion 186 and the second stabilizer portion 188 to rotate 190 the head 148 relative to a resting surface to ensure adequate contact (e.g., minimize gaps) between the movement stabilizer component 184 and the resting surface to minimize inadvertent motion of the patient's head during operation of the head-cooling device 1.

Figure 23:
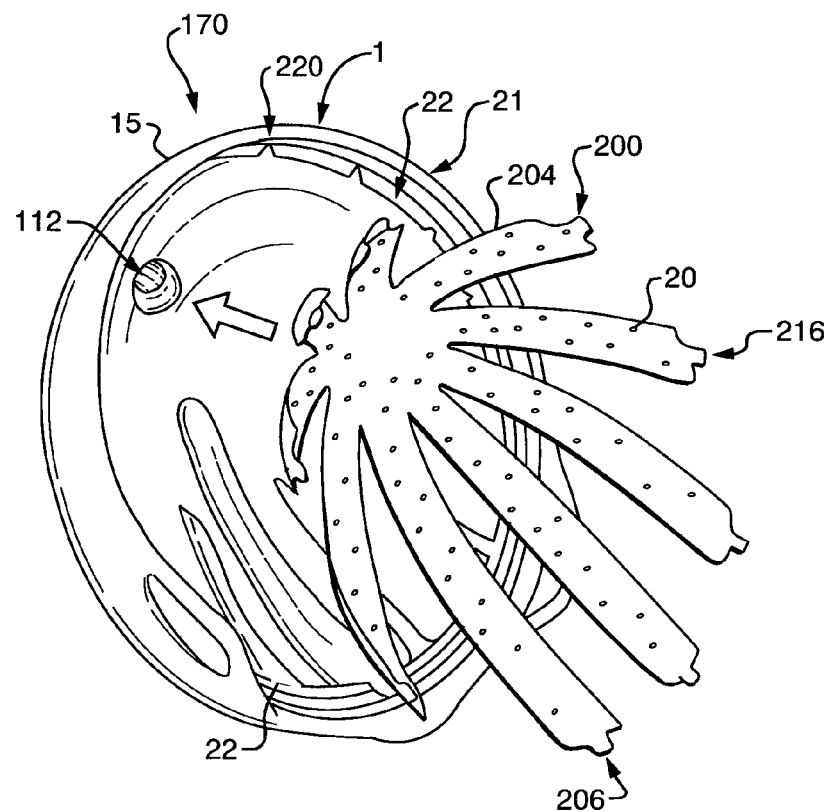
FIG. 23 illustrates the head-cooling device having a fluid distribution manifold, according to one embodiment of the invention.
Figure 24:
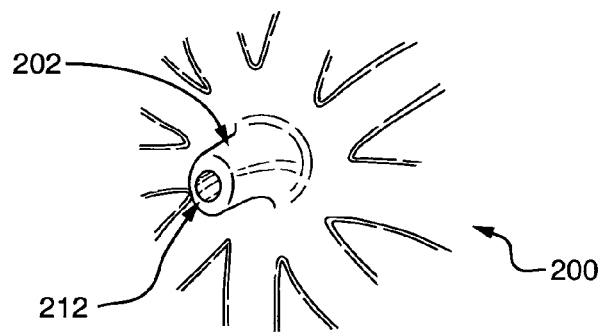
FIG. 24 illustrates the fluid distribution manifold of FIG. 23, according to one embodiment of the invention.

FIGS. 23 and 24 illustrate one arrangement of the head-cooling device 1 where the cap 15 has a fluid distribution manifold 200 configured to removably couple to the fluid inlet 112 of the cap 15. In one arrangement, the fluid distribution manifold 200 is formed from a polyethylene (PET) plastic material. The fluid distribution manifold 200 has a connector portion 202, arms 204 defining jets 20, and attachment mechanisms 206 associated with each arm 204. Use of the removable fluid distribution manifold 200 allows a user to replace the fluid distribution manifold 200 in the case where the jets 20 become clogged or degrade after repeated use of the head-cooling device 1.

The connector portion 202, in one arrangement, is configured to insert within the fluid inlet 112 of the cap 15, via a friction or interference fit, to secure a first end 212 of the fluid distribution manifold 200 to the cap 15. The connector portion 202 receives cooling fluid from the cooling fluid source (e.g., reservoir of the console 2) and allows flow of the fluid within the arms 204 of the fluid distribution manifold 200. The attachment mechanisms 206 associated with each arm 204 are configured to insert within the first sealing member 22 of the channel 21 in one arrangement. The attachment mechanisms 206 secure a second end 216 of the fluid distribution manifold 200 to the cap 15.

Figure 25:
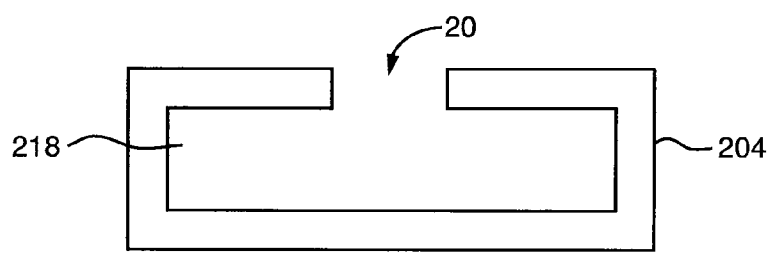
FIG. 25 illustrates a sectional view of an arm of the fluid distribution manifold of FIG. 23, according to one embodiment of the invention.

FIG. 25 illustrates a cross-sectional view of an arm 204 of the fluid distribution manifold 200. Each arm 204 defines openings or jets 20 used to distribute cooling fluid, from the fluid source, to the fluid circulation space 25. Cooling fluid travels from the connector portion 202 through the arms 204 via a channel 218 defined by the arms 204. The cooling fluid exits the fluid distribution manifold 200 via the openings 20.

FIG. 23 also illustrates the use of ventilation openings 220 within the cap 15. In one arrangement, the first sealing member 22 defines ventilation openings 220 oriented between the aspiration channel 21 and the fluid circulation space 25. During operation, the aspiration channel 21 attaches to a negative gage pressure source. The negative gage pressure source removes air from the aspiration channel 21 to seal the rim of the cap 15 to a patient's head. During operation, however, air can enter the fluid circulation space 25 and reduce the volume, and therefore the efficiency, of the cooling fluid within the fluid circulation space 25. The ventilation openings 220 provide fluid communication between the aspiration channel 21 and the fluid circulation space 25 such that, during operation, the aspiration channel 21 scavenges or removes air within the circulation space 25, thereby maximizing the amount of cooling fluid within the fluid circulation space 25. In one arrangement, the first sealing member 22 defines the ventilation openings 220 along a front portion 170 of the cap 15, such that the first sealing member 22 defining the ventilation openings 220 contacts a forehead of a patient's head.

Figure 26:
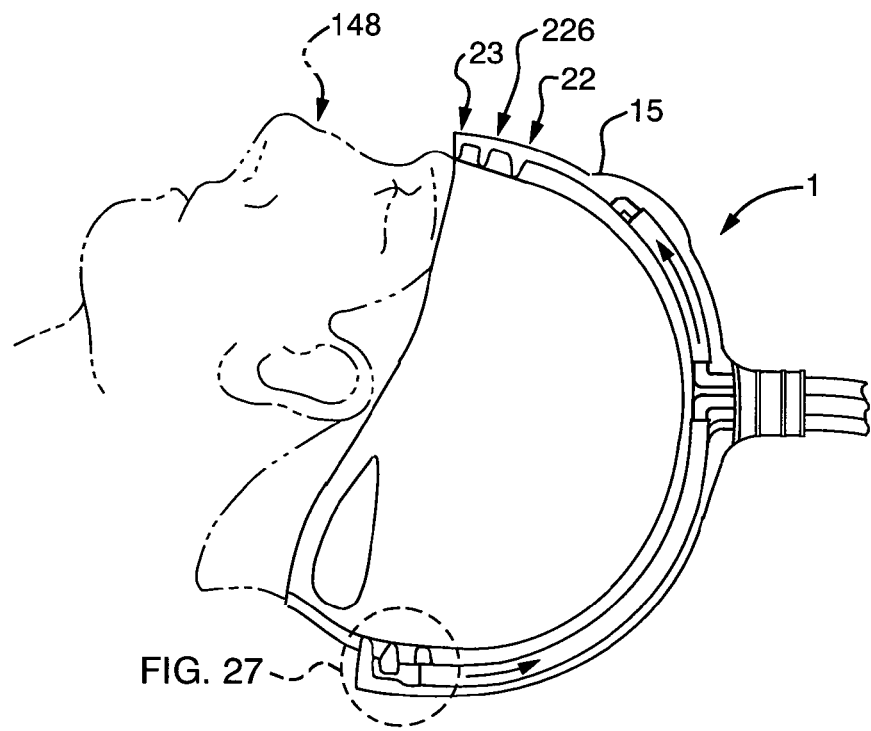
FIG. 26 illustrates the head-cooling device having a third sealing member, according to one embodiment of the invention.
Figure 27:
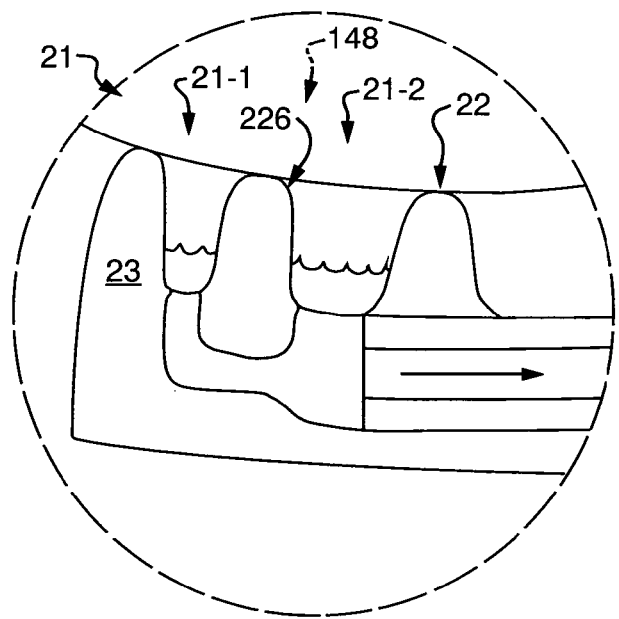
FIG. 27 illustrates the third sealing member of FIG. 26, according to one embodiment of the invention.

FIGS. 26 and 27 illustrate one arrangement of the head-cooling device 1 where the channel 21 has a third sealing member 226 disposed on the inner surface 102 of the cap 15 about a circumference defined by the cap 15. The third sealing member 226 orients between the first sealing member 22 and the second sealing member 23 of the channel 21. The third sealing member 226 divides the channel 21 into a first channel portion 21-1 and a second channel portion 21-2. As illustrated in FIG. 27, both the first channel portion 21-1 and the second channel portion 21-2 are in fluid communication with the aspiration manifold 17 of the cap 15. When a patient wears the head-cooling device 1, the first sealing member 22, the second sealing member 23, and the third sealing member 226 contact the patient's head. During operation, a negative gage pressure source removes air from the first channel portion 21-1 and the second channel portion 21-2 to seal the cap 15 against the patient's head 148. Because the third sealing member 226 divides the channel 21 into separate sealing portions 21-1, 21-2, the third sealing member 226 creates a secondary seal (e.g., second channel portion 21-2) between the patient's head 148 and the head-cooling device 1 during operation. Such a secondary seal minimizes cooling fluid (e.g., cooling fluid that migrates into the channel 21) from flowing beyond the rim 110 of the head-cooling device 1 during operation.

Figure 28:
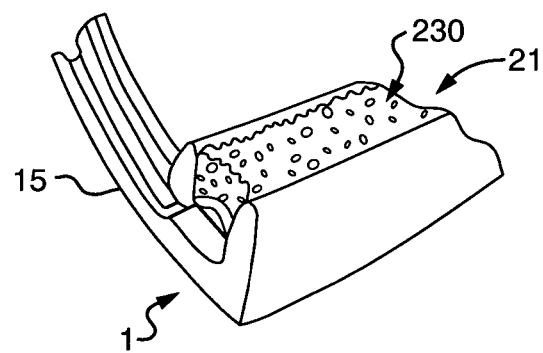
FIG. 28 illustrates the head-cooling device having a wicking material within a channel of the head-cooling device, according to one embodiment of the invention.

FIG. 28 illustrates one arrangement of the head-cooling device 1 where the aspiration channel 21 includes a fluid absorption material 230. For example, the absorption material 230 is formed of a sponge or foam-type material having fluid absorbance properties. In one arrangement, the aspiration channel 21 attaches to a negative gage pressure source and actively removes fluid from the fluid circulation space 25. In such an arrangement, the absorption material 230 aids in directing the fluid from the fluid circulation space 25 into the aspiration channel 21 and maintaining the fluid within the aspiration channel 21 (e.g., minimizes leakage of the fluid). In another arrangement, the aspiration channel 21 is open to the atmosphere (e.g., does not attach to a negative gage pressure source). In such an arrangement, the absorption material 230 aids in directing the cooling fluid from the fluid circulation space 25 into the aspiration channel 21. For example, assume the aspiration channel 21 has an outlet port open to the atmosphere and located at a rear or back portion 174 of the cap 15. The absorption material 230 absorbs cooling fluid from the fluid circulation space, such as via wicking through the patient's hair, and carries the cooling fluid to the outlet port. Because the outlet port is open to the atmosphere, the cooling fluid exits the aspiration channel by way of gravity (e.g., a gravity feed).

Figure 29:
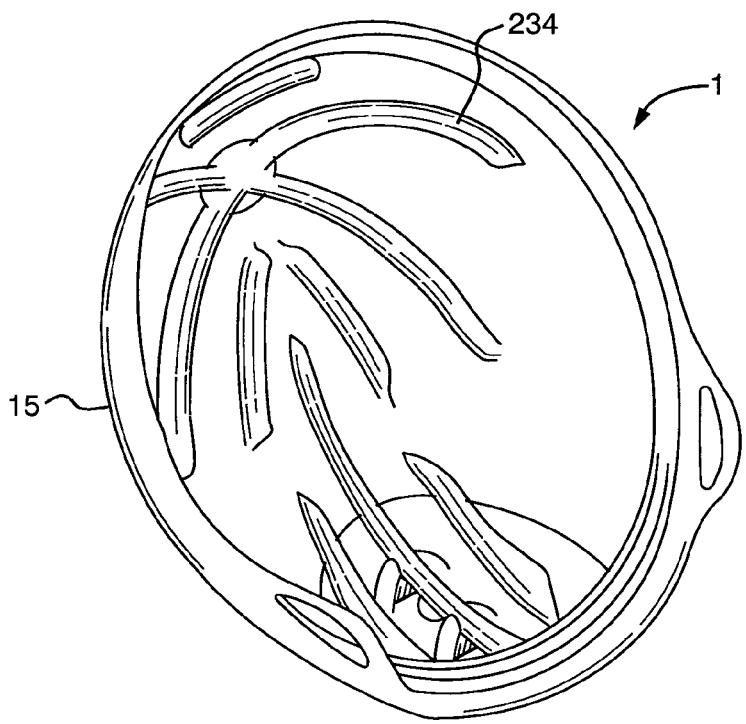
FIG. 29 illustrates the head-cooling device having flow channels, according to one embodiment of the invention.
Figure 30:
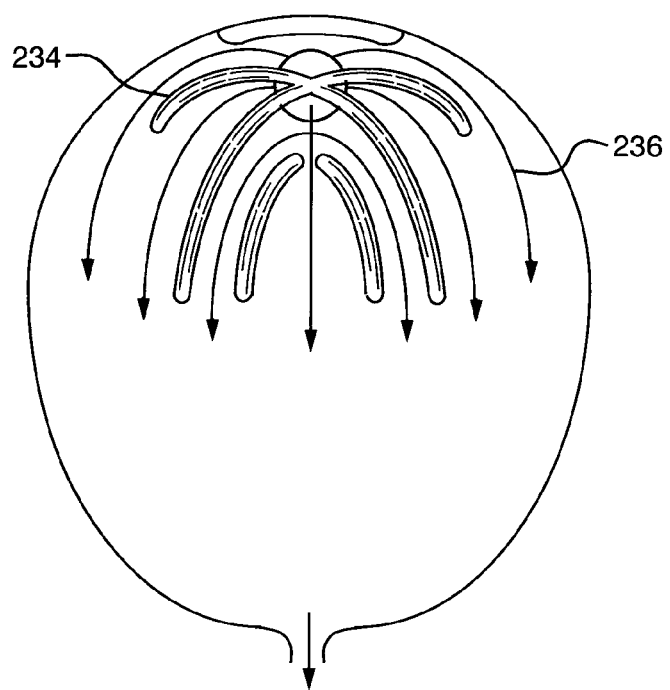
FIG. 30 illustrates the head-cooling device of FIG. 29, according to one embodiment of the invention.

FIGS. 29 and 30 illustrate one arrangement of the head-cooling device 1 where the cap 15 defines flow channels 234 disposed on the inner surface 102 of the cap 15 and in fluid communication with the fluid circulation space 25. In one arrangement, the flow channels 234 are formed as protrusions extending from the inner surface 102 of the cap 15. During operation, cooling fluid enters the cap 15 via an inlet (e.g., inlet manifold 16) and flows 236 across the flow channels 234 within the cap 15. The flow channels 234 distribute the cooling fluid to a patient's head in a substantially uniform manner, as indicated in FIG. 30. Such distribution minimizes non-uniform cooling of the patient's head and minimized the amount of time required to induce systemic hypothermia in the patient.

Figure 31:
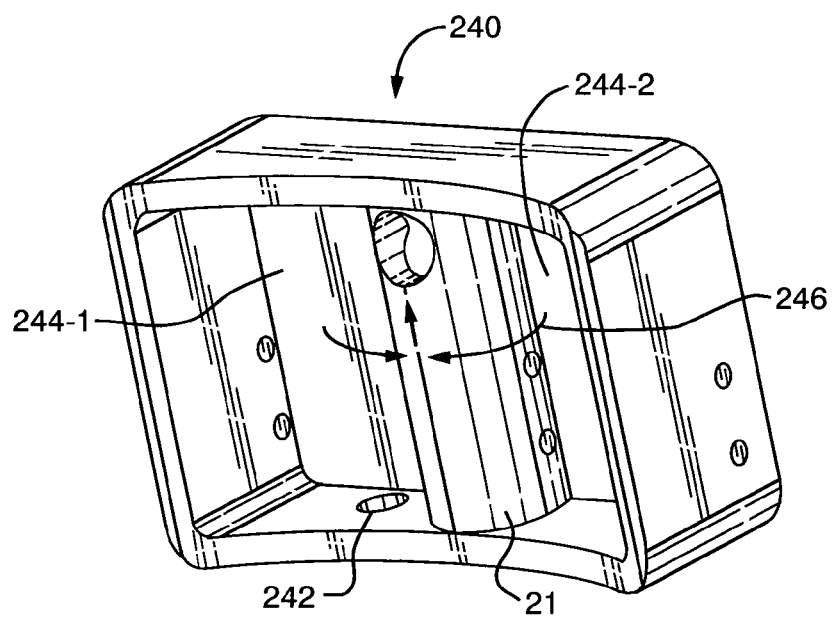
FIG. 31 illustrates a fluid collection reservoir for a head-cooling device, according to one embodiment of the invention.

FIG. 31 illustrates a fluid collection reservoir 240 for use with the head-cooling device 1. The fluid collection reservoir 240 defines collection chambers 244, such as a first collection chamber 244-1 and a second collection chamber 244-2, vent 242 and a suction channel that attaches to the aspiration channel 21 of the cap 15. In one arrangement, the fluid collection reservoir 240 couples to a rear or back portion 174 of the cap 15 such that the fluid collection reservoir 240 is in fluid communication with both the fluid circulation space 25 and the aspiration channel 21 of the cap 15.

For example, during operation, cooling fluid enters the cooling device via an inlet (e.g., inlet manifold 16). The cooling fluid circulates within the fluid circulation space 25, defined by the cap 15. Because the vent 242 of the fluid collection reservoir 240 is open to the atmosphere, the vent 242 causes the cooling fluid to collect within the chambers 244-1, 244-2 of the fluid collection reservoir 240. The suction channel 21 of the fluid collection reservoir 240 attaches to the aspiration channel 21 of the cap 15 that, in turn, attaches to a negative gage pressure source. Suction created by the negative gage pressure source causes the fluid, collected within the chambers 244-1, 244-2 to flow 246 into the suction channel 21, via a Venturi effect. The associated aspiration channel 21 returns the cooling fluid to the console 2 for recooling.

Figure 32:
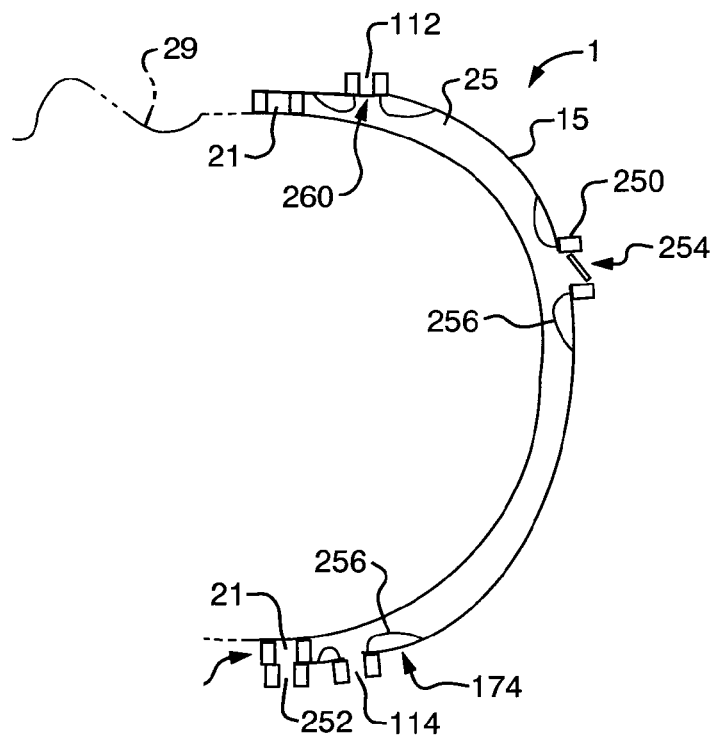
FIG. 32 illustrates a side sectional view of a head-cooling device 1, according to one embodiment of the invention.
Figure 33:
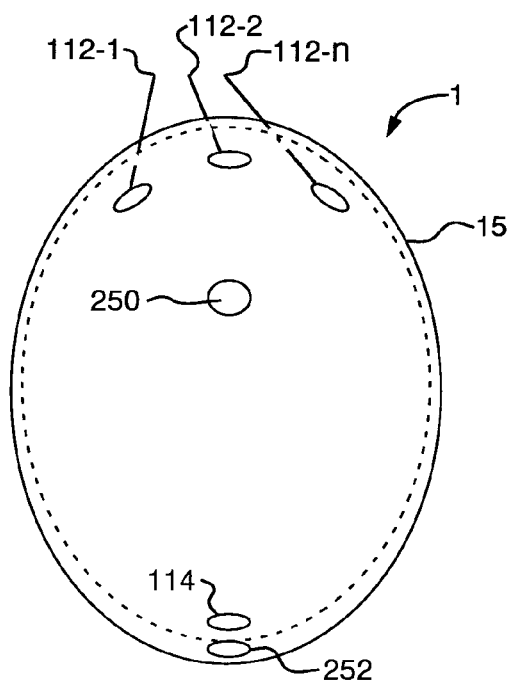
FIG. 33 illustrates a top view of the head-cooling device of FIG. 32, according to one embodiment of the invention.

FIGS. 32 and 33 illustrate an arrangement of the head-cooling device 1. The head-cooling device 1 has an aspiration channel 21 having an aspiration channel outlet 252, such as an aspiration manifold 17, fluid inlets 112, and a fluid outlet 114. The head-cooling device 1 defines a vent opening 250 and defines a support 256 surrounding each of the fluid inlets 112, fluid outlet 114, and the vent opening 250. The supports 256, in one arrangement, are hemispherically shaped and are configured to maintain spacing between, and minimize blockage between, the patient's head 29 and the fluid inlets 112, fluid outlet 114, and the vent opening 250.

The aspiration channel outlet 252 allows the head-cooling device 1 to maintain the aspiration channel 21 (e.g., a volume between the aspiration channel 21 and the patient's head 29) at a negative gage pressure, thereby allowing removal of air from the aspiration channel 21 and sealing the rim 110 of the cap 15 against the patient's head 29. For example, in one arrangement, the aspiration channel outlet 252 connects to a negative gage pressure source within the console 2. During operation, the negative gage pressure source induces a negative gage pressure within the channel 21 to seal the rim 110 of the cap 15 to the head 29.

In one arrangement, the head-cooling device 1 has multiple fluid inlets 112-1, 112-2, 112-N that provide substantially uniform distribution and flow of cooling fluid within the fluid circulation space 25 between the cap 15 and the patient's head 29. In one arrangement, each of the fluid inlets 112 has a respective nozzle 260 that provides a spray of cooling fluid to the patient's head 29. The nozzles 260 provide substantially uniform distribution of cooling fluid within the fluid circulation space 25.

The vent opening 250, defined by the head-cooling device 1, in one arrangement, opens the fluid circulation space 25 to the atmosphere to substantially equalize the pressure within the fluid circulation space 25 to atmospheric pressure. In such an arrangement, the vent opening 250 maintains the fluid circulation space 25 at substantially atmospheric pressure. In one arrangement, the vent opening 250 has a check valve 254. The check valve 254 minimizes the ability of the cooling fluid to exit the fluid circulation space 25 through the vent opening 250, thereby minimizing leakage of the cooling fluid from the head-cooling device 1, and maintains communication between the fluid circulation space 25 and the atmosphere. The fluid outlet 114 is open to the atmosphere and oriented at a back portion 174 of the head-cooling device 1. In such a configuration, with the fluid circulation space 25 maintained at atmospheric pressure (e.g., via the vent opening 250), the fluid outlet 114 allows cooling fluid to exit the fluid circulation space 25 via gravity (e.g., a gravity feed).

Figure 34:
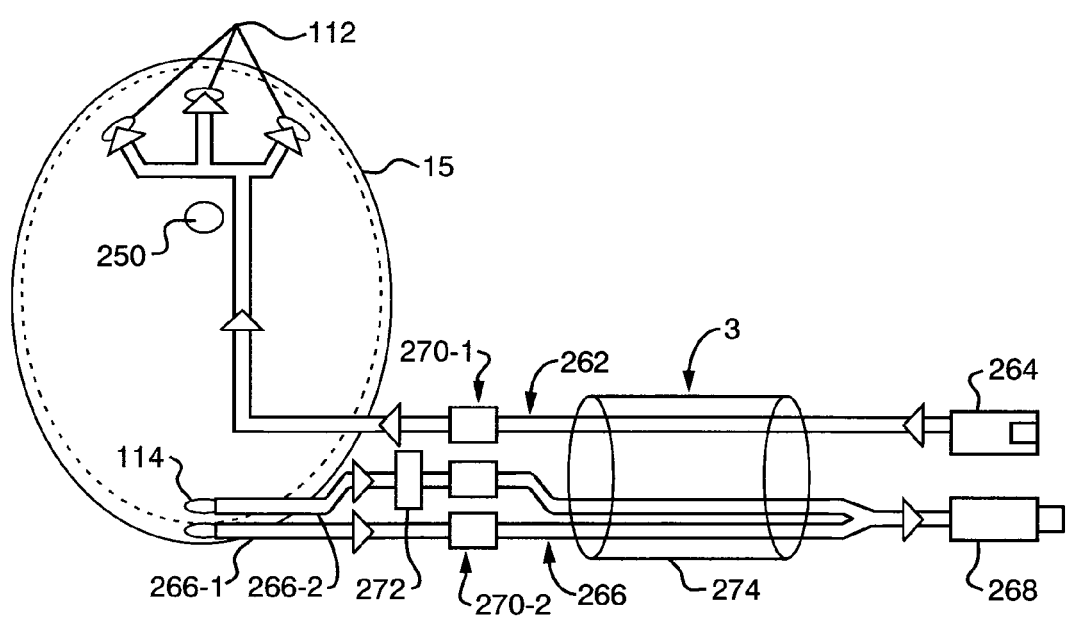
FIG. 34 illustrates an umbilical for use with the head-cooling device of FIG. 32, according to one embodiment of the invention.

FIG. 34 illustrates an arrangement of the umbilical 3 connecting the head-cooling device 1 to a console 2. The umbilical 3 has an inlet tube 262 attached to an inlet tube connector 264, an outlet tube 266 attached to an outlet tube connector 268.

The inlet tube 262 couples the fluid inlets 112 of the head-cooling device 1 to a positive gage pressure source of the console 2. The outlet tube 266 couples the aspiration channel 21 of the head-cooling device 1 to a negative gage pressure source of the console 2. In one arrangement, the outlet tube 266 is configured as a first outlet tube 266-1 and a second outlet tube 266-2 where the first outlet tube 266-1 couples the aspiration channel 21 of the head-cooling device 1 to the negative gage pressure source of the console 2 and the second outlet tube 266-2 couples the fluid outlet 114 of the head-cooling device to the negative gage pressure source of the console 2. In one arrangement, a thermally insulated conduit 274 surrounds both the inlet tube 262 and the outlet tube 266. The thermally insulated conduit 274 minimizes heating of the cooling fluid carried by the tubes 262, 266 to or from the head-cooling device 1.

In one arrangement, the inlet tube 262 has an inlet tube check valve 270-1 located between the head-cooling device 1 and the console 2 while the outlet tube 270 has an outlet tube check valve 270-2 located between the head-cooling device 1 and the console 2. The inlet check valve 270-1 and the outlet check valve 270-2 minimize leakage of cooling fluid from the umbilical 3 when a user removes the head-cooling device 1 from the patient's head 29 (e.g., after application of the cooling fluid to the patient is completed).

In one arrangement, the outlet tube 270 has a debris collector 272, such as a screen, located between the head-cooling device 1 and the console 2. For example, during operation, hair from the patient's head can enter the outlet tube 270 and travel to the console 2, thereby potentially clogging and damaging the pumps (e.g., positive gage pressure source and negative gage pressure source) associated with the console 2. The debris collector 272 minimizes the amount of material (e.g., hair) received by the console 2 from the head-cooling device 1 during operation.

Figure 35:
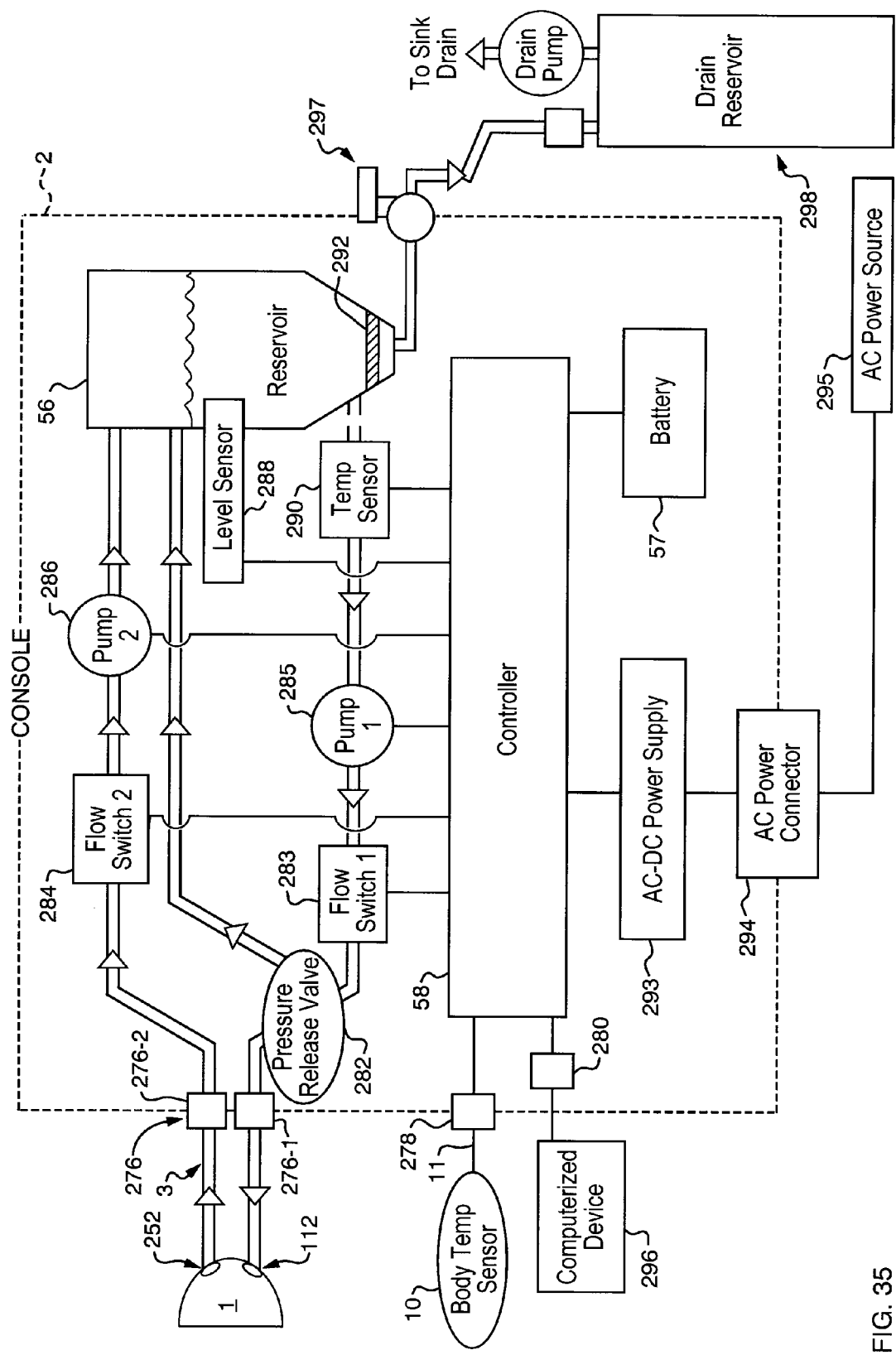
FIG. 35 illustrates a console, according to one embodiment of the invention.

FIG. 35 illustrates an arrangement of the console 2, such as for use with the head-cooling device 1 as shown in FIGS. 32-34. The console 2 has flow connectors 276, a body temperature sensor connector 278, and a computerized device connector 280. The console 2 also has a pressure release valve 282, a first flow switch 283, a second flow switch 284, a positive gage pressure source (e.g., first pump) 285, a negative gage pressure source (e.g., second pump) 286, a reservoir level sensor 288, and a cooling fluid temperature sensor 290.

The controller also has the reservoir 56, controller 58, battery 57, a power supply 293 in electrical communication with the controller 58 and in electrical communication with a power connector 294. The power connector 294, in one arrangement, is configured to provide power to the power supply 293 from a power source 295, such as a wall outlet.

The flow connectors 276, in one arrangement, include a first flow connector 276-1 and a second flow connector 276-2. The first flow connector 276-1 allows connection of the aspiration channel outlet 252 of the head-cooling device 1 to the negative gage pressure source 286 of the console 2. The second flow connector 276-2 allows connection of the fluid inlet 112 of the head-cooling device 1 to the positive gage pressure source 285 of the console 2. The computerized device connector 280 allows connection of a computerized device 296, such as a personal computer, to the controller 58, thereby allowing a user to retrieve and store data (e.g., such as information collected by the sensor 10) collected by the controller 58 of the console 2.

The sensor connector 278 allows connection of a sensor, such as a body temperature sensor 10 to the controller (e.g., motherboard) 58 of the console 2. Such connection allows the controller 58 to display a measurement (e.g., a body temperature measurement), as measured by the sensor, to a user via a display. In one arrangement, the controller 58 uses a patient's body core temperature measurement, as measured and transmitted by the temperature sensor 10, to control operation of the cooling system 100.

For example, in one arrangement, the patient's body core temperature has a set-point range between approximately 32° C.-37° C. The controller 58 is configured with a particular set-point value. During operation, the temperature sensor 10 transmits a temperature signal (e.g., body core temperature signal) to the controller. When the controller 58 detects the temperature signal is, for example, 0.2° C. greater than the set-point value, the controller 58 transmits a signal to the first pump 285 and the second pump 286 that causes the pumps 285, 286 to circulate cooling fluid within the cooling system 100 (e.g., to and from the patient). When the controller 58 detects the temperature signal is, for example, 0.0° C. above the set-point value, the controller 58 transmits a signal to the first pump 285 and the second pump 286 that causes the pumps 285, 286 to stop circulation of cooling fluid within the cooling system 100 (e.g., to and from the patient).

The first flow switch 283 is in fluid communication with the reservoir 56 and in electrical communication with the controller 58. The first flow switch 283 positions, within a fluid flow path, between the reservoir 56 and the fluid inlet 112 of the head-cooling device 1. The second flow switch 284 is in fluid communication with the reservoir 56 and in electrical communication with the controller 58. The second flow switch 284 positions, within a fluid flow path, between the reservoir 56 and the aspiration channel outlet 252 of the head-cooling device 1. The first flow switch 283 and the second flow switch 284 are configured to detect flow along the respective flow paths. For example, in one arrangement, when the first flow switch 283 detects a reduction in cooling fluid flow along the respective flow path (e.g., indicating a blockage along the flow path), the flow switches 283, 284 transmit a signal (e.g., flow warning signal) to the controller 58. In response to the signal, the controller 58 indicates to a user, via a display, blockage of the flow path, thereby allowing the user to unblock the flow path to ensure adequate operation of the cooling system 100.

The pressure release valve 282 positions, within a fluid flow path, between the flow switch 283 and the fluid inlet 112 of the head-cooling device 1. The pressure release valve 282 is configured to regulate pressure of the cooling fluid from the positive gage pressure source 285 to the head-cooling device 1 (e.g., a fluid circulation space 25 defined between the head-cooling device 1 and a patient's head 29). For example, in the case where the fluid pressure within the fluid circulation space 25 exceeds a preset maximum, the pressure regulation valve 282 directs the cooling fluid from the positive gage pressure source 285 to the reservoir 56, thereby minimizing over pressurization and potential failure of the head-cooling device 1.

The level sensor 288, in one arrangement, is in fluid communication with the cooling fluid within the reservoir 56 and is in electrical communication with the controller 58. The level sensor 288 is configured to detect an amount of cooling fluid within the reservoir 56. For example, in one arrangement, when the level sensor 288 detects the amount of fluid within the reservoir 56 falls below a preset level, the level sensor 288 transmits a signal (e.g., level warning signal) to the controller 58. In response to the signal, the controller 58 indicates to a user, via a display, a low level of cooling fluid within the reservoir 56, thereby allowing the user to fill the reservoir 56 with additional cooling fluid to ensure adequate operation of the cooling system 100.

The temperature sensor 290, in one arrangement, is in fluid communication with the cooling fluid within the reservoir 56 and is in electrical communication with the controller 58. The temperature sensor 290 is configured to measure the temperature of the cooling fluid within the reservoir 56. For example, when the temperature sensor 290 detects the temperature of the cooling fluid rises above a preset level, the temperature sensor 290 transmits a signal (e.g., temperature warning signal) to the controller 58. In response to the signal, the controller 58 indicates to a user, via a display, a relatively high temperature of the cooling fluid, thereby allowing the user to reduce the temperature of the cooling fluid or replace the cooling fluid with relatively low temperature cooling fluid to ensure adequate operation of the cooling system 100.

In one arrangement, the reservoir 56 defines a substantially conical shape. For example, the reservoir 56 is formed of a tapered wall such that the taper narrows toward a fluid outlet of the reservoir 56. The conical shape of the reservoir 56 allows substantially complete drainage of the cooling fluid from the reservoir 56 after operation of the cooling system 100. In one arrangement, the reservoir 56 has a reservoir screen 292 oriented in proximity to the reservoir outlet. The reservoir screen 292 minimizes blockage of the reservoir outlet, such as caused by ice or solid substances within the reservoir 56, during draining of the reservoir 56.

In one arrangement, the reservoir outlet has a valve 297 coupled to an external drain 298, such as a drain reservoir. The valve 297 minimizes leakage of the reservoir 56 during operation of the cooling system 100 and allows drainage of the reservoir 56 into the external drain 298.

Figure 36:
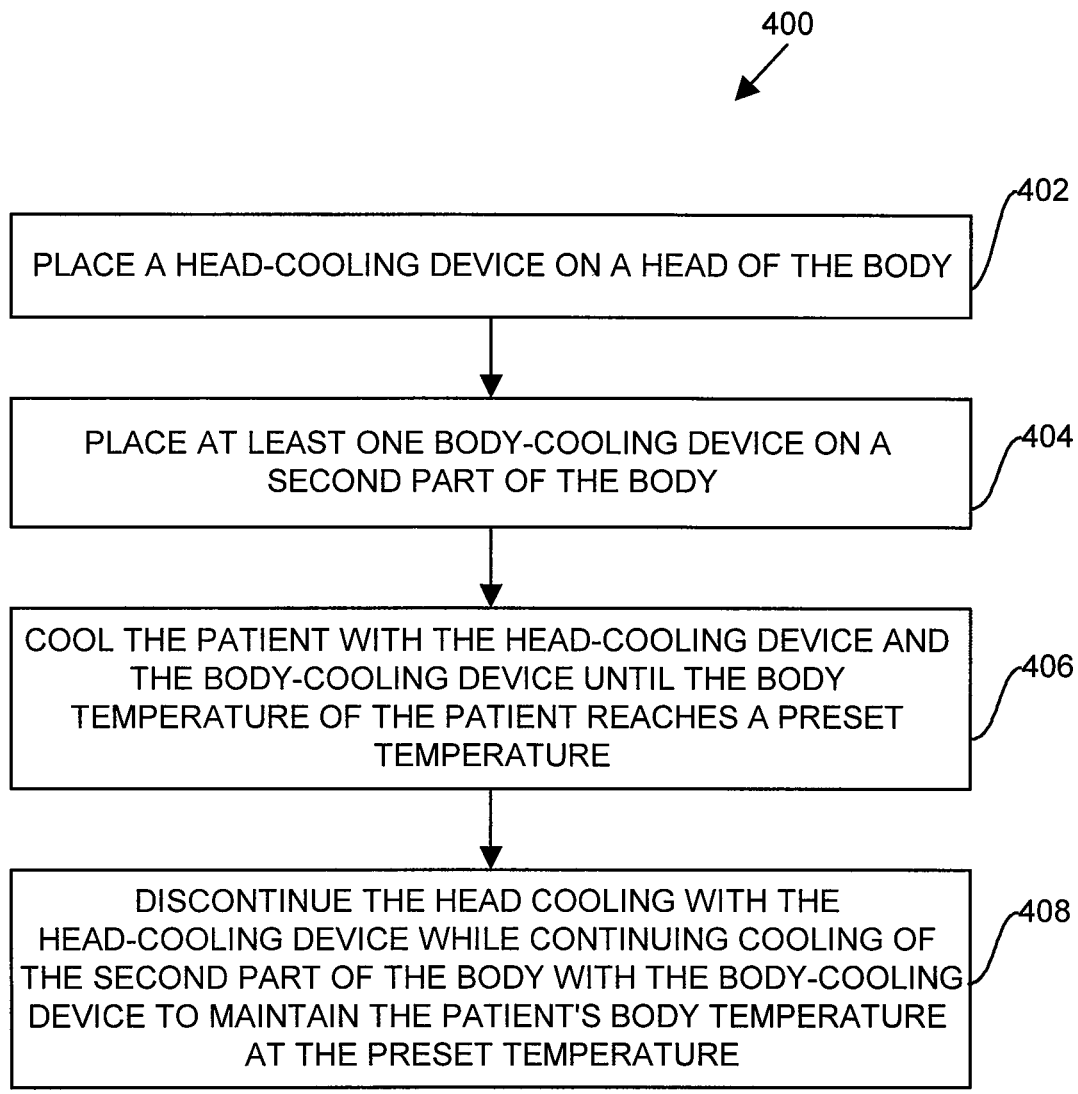
FIG. 36 illustrates a flowchart of a procedure for using a cooling system, according to one embodiment of the invention.

FIG. 36 illustrates a method 400 for inducing hypothermia in a body to a preset temperature. In one arrangement, a user, such as a medical technician, performs the method 350.

In step 402, a user places a head-cooling device 1 on a head of a body. For example, the head-cooling device 1 allows contact between the patient's head and a cooling fluid pumped into the head-cooling device 1 to induce systemic hypothermia in the patient.

In step 404, the user places at least one body-cooling device 6 on a second part of the body. For example, in the case where the body-cooling device 6 is configured as a neck-cooling device 90, the user places the device 90 onto the patient in the region of the left carotid artery and the left jugular vein and in the region of the right carotid artery and the right jugular vein.

In such an arrangement, the neck-cooling device 90 effectively cools the blood flowing through the carotid arteries and jugular veins and increases the rate of induction of systemic hypothermia within the patient.

In step 406, the user cools the patient with the head-cooling device 1 and the body-cooling device 6 until the body temperature of the patient reaches a preset temperature. For example, assume the user measures the core body temperature of the patient using the body temperature sensor 10. When the core body temperature reaches a preset level of between approximately 32° C. and 37° C. the body temperature sensor 10 indicates the temperature to the user, thereby notifying the user that systemic hypothermia has been achieved in the patient.

In step 408, the user discontinues the head cooling with the head-cooling device 1 while continuing cooling of the second part of the body with the body-cooling device 6 to maintain the patient's body temperature at the preset temperature. By removing the head-cooling device 1, the user minimizes the risk of lowering the temperature of the patient below a low-level threshold (e.g., below approximately 32° C.), thereby potentially endangering the patient.

While this invention has been particularly shown and described with references to preferred embodiments thereof, it will be understood by those skilled in the art that various changes in form and details may be made therein without departing from the spirit and scope of the invention as defined by the appended claims.

As described above, the cooling system 100 includes a console 2 and a tissue cooling device. As indicated above, in one arrangement, the tissue cooling device is configured as the head-cooling device 1. Also as indicated above, the tissue cooling device is configured as the body-cooling device 6 where the body-cooling device 6 has a heat transfer membrane 33. During operation, jets of fluid 40 are directed at the inner surface of heat transfer membrane 33 and create fluid turbulence at the inner surface of heat transfer membrane 33. During operation, (e.g., when the heat transfer membrane contacts a body portion or tissue region of interest of a patient), such turbulence increases the heat transfer from the patient's body, across heat transfer membrane 33, and into cooling fluid contained in fluid circulation chamber 44. Such a configuration of the body-cooling device 6 is by way of example only. In one arrangement, the body-cooling device 6 is configured as having an aspiration channel oriented about an edge of the body-cooling device 6.

For example, the body-cooling device 6 includes a tissue covering portion (e.g., such as substrate 31) having an outer surface and an inner surface. The tissue covering portion defines an edge and is configured to cover a tissue region of interest. For example, in the case where the body-cooling device 6 is a neck-cooling device 90, the body-cooling device 6 covers the neck of the wearer. The body-cooling device 6 further includes an inlet in communication with the tissue covering portion. The inlet receives pressurized fluid from a pressure source (e.g., from the positive gage pressure source of the console 2) and distributes the cooling fluid to the tissue region of interest. For example, as the inlet distributes the cooling fluid to the tissue region of interest (e.g., to the neck), the cooling fluid contacts the tissue (e.g., neck) covered by the tissue covering portion.

The body-cooling device 6 further includes an aspiration channel disposed on the inner surface of the tissue covering portion about the edge defined by the tissue covering portion. For example, in one arrangement, the aspiration channel is configured as the aspiration channel illustrated in FIG. 4 (e.g., is defined by a first sealing member, a second sealing member, and a second inner surface of the tissue covering portion). The aspiration channel fluidly communicates with a suction source. For example, in one arrangement, the aspiration channel connects to the negative gage pressure source of the console 2. During operation, the suction source removes air from a space defined by the aspiration channel to seal the edge of the tissue covering portion to a periphery of the tissue region of interest (e.g., to a periphery of the neck of a patient). For example, in one arrangement, the space defined by the aspiration channel includes the volumetric space between the periphery of the tissue region of interest and the aspiration channel, as indicated in FIG. 4. By sealing the edge of the tissue covering portion to the periphery of the tissue region of interest, the aspiration channel minimizes leakage of the pressurized fluid beyond the edge of the tissue covering portion.

While the above-described arrangement of the body-cooling device indicates that the body-cooling device covers a body portion of a patient, such as a patient's neck, such indication is by way of example only. In one arrangement, the body-cooling device 6 is configured to surround substantially an entire body surface of the patient. For example, the body-cooling device is configured as a bag or a pouch defining an edge having an aspiration channel. In one arrangement, the pouch is configured to surround at least a portion of a limb, (e.g., arm or leg) of the patient. During operation, the aspiration channel seals the edge of the pouch to the limb while cooling fluid circulates within a fluid circulation space defined between the limb and an interior surface of the pouch. In another arrangement, the pouch is configured as a body suit to surround the body surface of a patient. For example, in such a configuration, the body suit surrounds the arms, legs, pelvis and torso of a patient. During operation, the aspiration channel seals the edge of the pouch to a neck area of the patient while cooling fluid circulates within a fluid circulation space defined between the body (e.g., hands, arms, feet, legs, pelvis, and torso) of the patient and an interior surface of the pouch. Such a configuration reduces the core body temperature of the patient while minimizing leakage of the cooling fluid beyond the edge of the body suit.

As indicated above, the neck-cooling device 90 has a heat transfer membrane 33. During operation, jets of fluid 40 are directed at the inner surface of heat transfer membrane 33 and create fluid turbulence at the inner surface of heat transfer membrane 33. Such turbulence increases the heat transfer from the patient's body, across heat transfer membrane 33, and into cooling fluid contained in fluid circulation chamber 44. Such a configuration of the neck-cooling device 90 is by way of example only. In one arrangement, the neck-cooling device 90 is configured similar to the cooling cap 15. For example, after a user applies the neck-cooling device 90 to a patient's neck, a cooling fluid flows into a fluid circulation space defined between the neck-cooling device 6 and the patient's neck such that the cooling fluid directly contacts the patient's neck. In such an arrangement, the neck-cooling device 90 also has an aspiration system to scavenge the cooling fluid (e.g., saline) from the fluid circulation space.

In one arrangement, the neck-cooling device 90 forms part of a head immobilizer device (e.g., a device that provides head and cervical immobilization). In such an arrangement, the head immobilizer device provides both neck cooling to a patient at risk for ischemic injury and minimizes inadvertent motion of the patient's head during operation of the neck-cooling device 90.

As indicated above, the head-cooling device 1 and the neck-cooling device 90 are formed as distinct (e.g., separate) devices that provide cooling to a patient's head and neck, respectively. In one arrangement, the head-cooling device 1 and the neck-cooling device 90 are integrated into a single unit having a single connector, or umbilical, that provides cooling fluid from the console 2 to the integrated unit. In one arrangement, the head-cooling device 1 and neck-cooling device 90 are provided in a variety of sizes to accommodate a variety of head sizes and neck sizes, such as corresponding to a patient's age (e.g., newborn to adult).

As indicated above, the head-cooling device 1 is configured such that cooling fluid enters the fluid circulation space defined by the head-cooling device 1 and the patient's head via multiple jets 20. Such a configuration is by way of example only. In another arrangement, the cooling fluid enters the fluid circulation space and directly contacts the scalp without the use of jets. For example, in one arrangement, fluid enters the infusion manifold 16 via inlet tube 4 and flows directly to the patient's scalp.

As indicated above, the cooling system has a body temperature sensor 10 removably connected to console 2 by a body temperature sensor lead 11. The cooling system 100 utilizes the body temperature sensor 10 to modulate patient cooling in order to maintain the patient's body at a predetermined hypothermic temperature. In one arrangement, the cooling system 100 includes physiological sensors placed on or into the patient to monitor body cooling and control the operation of the console so as to control body cooling. For example, the cooling system 100 includes electrocardiogram (EKG) sensors or pulse oximetry sensors for attachment to the patient to aid in adjusting or maintaining the patient's body temperature.

As described above, the console 2 provides a cooling fluid to a fluid circulation space located between the head-cooling device 1 and the patient's head, via a positive gage pressure source to induce systemic hypothermia in the patient. In one arrangement, the console 2 allows a user to select (e.g., set) a predetermined body temperature prior to the initiation of therapy or during therapy. For example, using a control panel of the console 2, the user programs into a memory (e.g., computer memory) associated with the console 2 a target temperature of the patient. Based upon a feedback loop created between the body temperature sensor 10 (e.g., as placed on the patient) and the console 2 and based upon the target temperature stored in the console's memory, the console automatically adjusts the amount or rate of delivery of the cooling fluid to the patient. In one arrangement, the console 2 allows the user to select a rate at which the patient's body is cooled or re-warmed.

In one arrangement, the cooling system includes interlocks that prevent operation of the system 100 if the user does not operate the system 100 correctly or if the system 100 malfunctions. For example, assume the user incorrectly programs the console 2 to induce a hypothermic temperature within the patient that could potentially damage the patient. In such an arrangement, based upon the detection of an improper temperature, the interlocks of the cooling system 100 become activated and prevent operation of the cooling system 100 (e.g., prevent delivery of the cooling fluid to the patient).

In one arrangement, control panel of the console 2 includes user feedback mechanisms that provide to the user the status of the patient during induction of systemic hypothermia. For example, the control panel of the console 2 includes an electronic display or mechanical indicator that provide the user with information regarding the operation of the system, activation of one or more interlocks, or the status of the patient's body cooling.

As indicated above, the console 2 of the cooling system 100 includes a positive gage pressure source (e.g., fluid pump) and a negative gage pressure source (e.g., aspiration pump) to respectively provide and remove fluid from the fluid circulation space 25. Such an arrangement is by way of example only. In another arrangement, the console has three pumps: a positive gage pressure source to provide cooling fluid to the circulation space 25 of the head-cooling device, a first negative gage pressure source to provide a seal about the rim of the head-cooling device, and a second negative gage pressure source to assist the egress of water from the fluid circulation space 25.

As indicated above, the aspiration channel 21, in one arrangement, is disposed about the entire circumference of the inner surface 102 at the bottom edge (e.g., rim 110) of the head cap 15 and, in one arrangement, is sized such that the inner diameter of aspiration channel 21 as defined by the inner diameter of inner seal 22 and/or outer seal 23 is approximately 2 to 30 percent smaller than the circumference of the patient's head 29. Since the circumference of the aspiration channel 21 is smaller than the patient's head 29, the force generated by the aspiration channel 21 on the patient's head maintains the head cap 15 on the patient's head during operation of the cooling system 100 and minimizes cooling fluid from leaking past the rim of the head cap 15 during operation. Such an arrangement is by way of example only.

In one arrangement, during operation, a portion of the cooling fluid within the fluid circulation space 25 contacts the inner seal 22 and the outer seal 23 of the aspiration channel 21 in a location between the seals 22, 23 and the patient's head 29. In such an arrangement, the cooling fluid contributes to sealing the aspiration channel 21 against the patient's head, thereby minimizing cooling fluid from leaking past the rim of the head cap 15 during operation. In another arrangement, the inner seal 22 and the outer seal 23 of the aspiration channel 21 each have a fluid resistant coating, such as a gel, grease, or adhesive, located between the seals 22, 23 and the patient's head 29. The fluid resistant coating contributes to sealing the aspiration channel 21 against the patient's head, thereby minimizing cooling fluid from leaking past the rim 110 of the head cap 15 during operation of the cooling system 100. In another arrangement, the rim 110 of the head cap 15 includes a constricting band disposed about the circumference of the cap 15. For example, in one arrangement, the constricting band is a drawstring in communication with, and disposed about the circumference of, the cap 15. Prior to operation of the cooling system 100, a user tightens the drawstring of the cap 15 to compress the cap 15 against a patient's head 29. Such compression minimizes cooling fluid from leaking past the rim 110 of the head cap 15 during operation of the cooling system 100.

As indicated above, the cap 15 of the head-cooling device 1 is formed as a rigid structure (e.g., thermoplastic) or as a flexible structure (e.g., elastomer). In one arrangement, the head-cooling device 1 is formed of a radio-translucent material to allow a user (e.g., medical technician) to perform an X-ray or CT scan on a patient wearing the head-cooling device 1 without requiring removal of the head-cooling device 1. In one arrangement, the head-cooling device 1 is configured to decompose or destruct after a single use to minimize reuse of the head-cooling device 1. For example, in one arrangement, when exposed to sterilization, such as through autoclaving, the material of the head-cooling device 1 degrades (e.g., becomes damaged), thereby indicating prior use of the head-cooling device 1.

Figure 37:
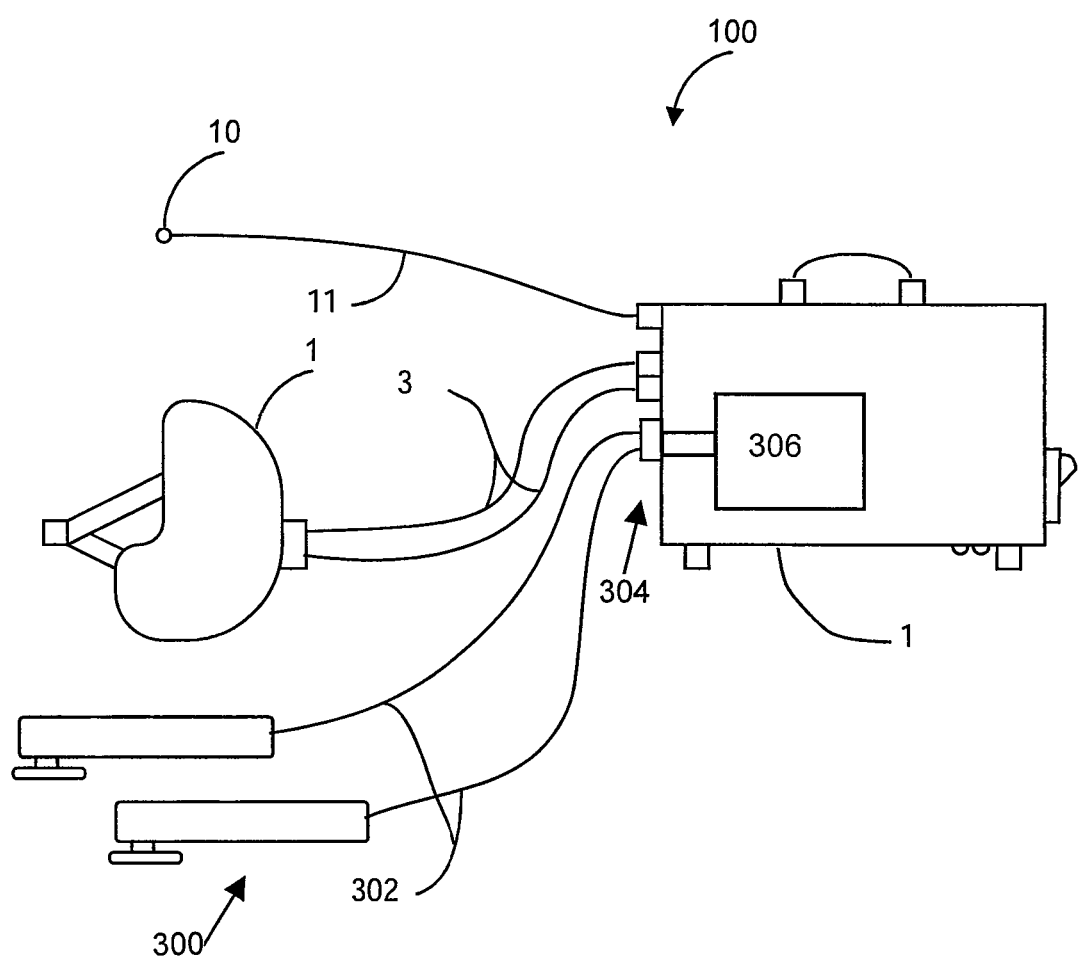
FIG. 37 illustrates a flowchart of a cooling system, according to another embodiment of the invention.

FIG. 37 illustrates an arrangement of a cooling system 100 having cardiopulmonary resuscitation equipment as part of the console 2. In such an arrangement, the cooling system 100 has a console 2, a head-cooling device 1, an umbilical 13 connecting the head-cooling device 1 to the console 2, a temperature sensor 10 in electrical communication with the console 2 via lead 11, and defibrillator electrode paddles 300 in electrical communication with the console 2 via defibrillator leads 302. The console 1 has defibrillator lead connectors 304 coupled to a defibrillator 306 associated with the console 1. The defibrillator lead connectors 304 provide electrical communication between the defibrillator paddles 300 and the defibrillator 306 of the console 2.

The cooling system 100 of FIG. 37 allows resuscitation of a patient stricken with cardiac arrest. For example, during operation, a user (e.g., medical technician) carries the cooling system 100 to a patient undergoing cardiac arrest. The user applies the defibrillator paddles 300 to the patient, engages the defibrillator 306 of the console 1 (e.g., places the defibrillator in an "on" mode of operation), and defibrillates the patient. The user places the head-cooling device on the patient's head, places the temperature sensor 10 on or into the patient's body, and connects the temperature sensor 10 to the console 2 using the lead 11. The user connects the head-cooling device 1 to the console 2 using the umbilical 3. The user activates the console 2 to provide cooling fluid to the head of the patient to minimize ischemic injury in the patient.

While FIG. 37 illustrates the console as having a defibrillator 306 as cardiopulmonary resuscitation equipment, such illustration is by way of example only. In one arrangement, the console 2 includes cardiopulmonary resuscitation equipment such as a chest compression system (CPR system). In another arrangement, the console 2 includes cardiopulmonary resuscitation equipment (e.g., ventilation equipment), such as a cardiopulmonary ventilation system. The CPR system and the ventilation system allow a user (e.g. medical technician) to attempt to restore circulation of blood in, and provide oxygen to, a patient such as a patient undergoing cardiac arrest.

Figure 38:
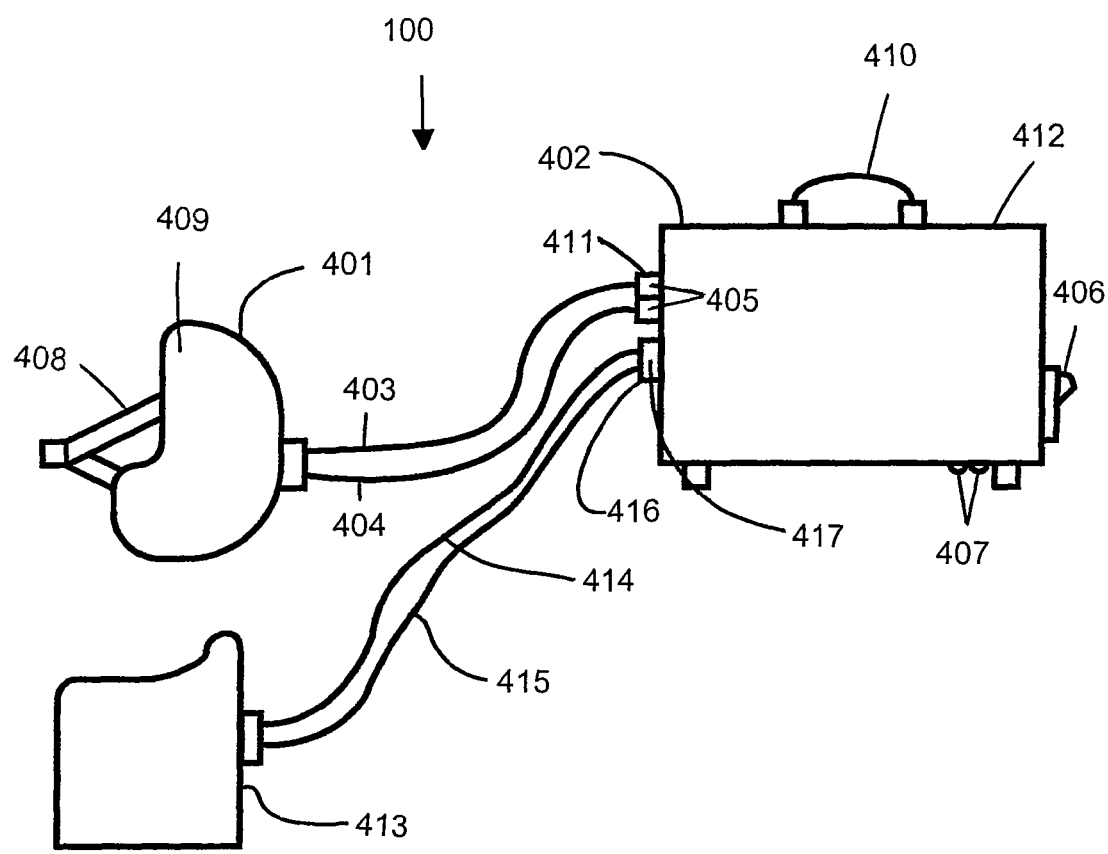
FIG. 38 illustrates an arrangement of the cooling system, according to one embodiment of the invention.

FIG. 38 illustrates an arrangement of the cooling system 100. Cooling cap 401 is connected to console 402 by an umbilical comprising cooling fluid inlet tube 403, and aspiration tube 404. Cooling cap 401 consists of inner liner (FIG. 40), outer liner 409, chin strap 408, and umbilical comprising cooling fluid inlet tube 403 and aspiration tube 404, and tube fittings 405. Components of the console 401 depicted are the console case 412, carrying handle 410, on/off switch 406, electrical battery recharging contacts 407, and tube fitting receptacles 411. The internal components of the console are described later. The cooling cap 401 is removably connectable to console 402 by tube fittings 405 mounted on the end of cooling fluid inlet tube 403, and aspiration tube 404, and by tube fitting receptacles 411 mounted on console 402. Tube fittings 405 and tube fitting receptacles 411 are readily commercially available. Chinstrap 408 holds cooling cap 401 to the patient's head. Outer liner 409 is an insulating cover made from closed cell foam with a woven outer covering. Chinstrap 408 is bonded to outer liner 408 by thread and adhesive. Console 402 provides cold saline to cooling cap 401 under pressure through cooling fluid inlet tube 403, and removes saline from cooling cap 401 by providing suction to cooling cap 401 through aspiration tube 404. The system is turned on and off by on/off switch 406. An internal electrical battery (not shown) may be recharged by a recharging cradle (not shown) through electrical battery recharging contacts 407. The console, in one arrangement, is approximately eighteen inches long, twelve inches high and eight inches deep and weighs between 6 and 15 pounds. Carrying handle 410 allows the console 402 to be carried my emergency medical personnel in close proximity to the patient during patient transport.

FIG. 38 also illustrates a cooling collar 413 connected to console 402 by an umbilical comprising cooling fluid inlet tube 414, and cooling fluid return tube 415. The cooling collar 413 is removably connected to the console 402 by tube fittings 416 mounted on the end of cooling fluid inlet tube 414, and cooling fluid return tube 415, and tube fitting receptacles 417 mounted on console 402. Tube fittings 416 and tube fitting receptacles 417 are readily commercially available. Console 402 provides cold saline to cooling cap 401 as described in FIG. 38, and also provides cold saline to cooling collar 413 under pressure. The cold saline circulates through channels in the wall of cooling collar 413 to cool the neck of the patient (see FIGS. 41 and 42) and returns to the console through cooling fluid return tube 415.

Figure 39:
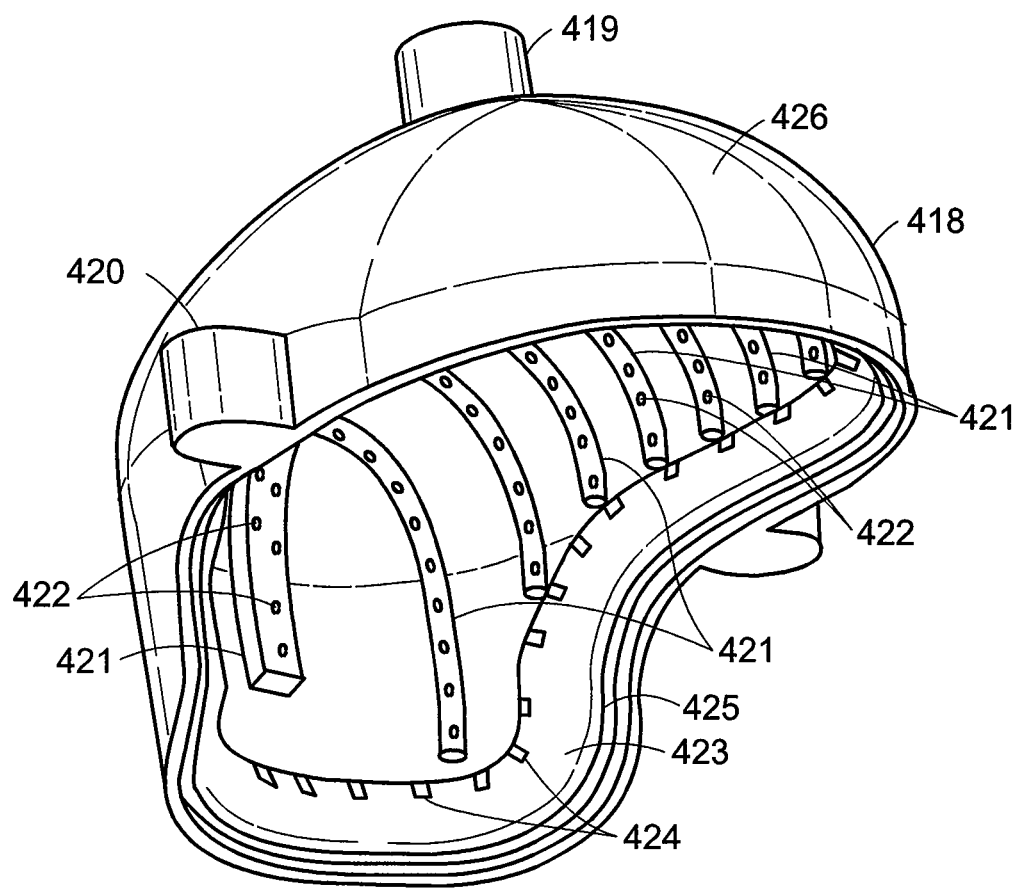
FIG. 39 illustrates an arrangement of an inner liner of the cooling cap of FIG. 38, according to one embodiment of the invention.

FIG. 39 depicts the inner liner 418 of cooling cap 1 (FIG. 38). Inner liner 418 consists of inner shell 425, and outer shell 426. Inner shell 425 and outer shell 426 are molded from an elastomer material such as silicone rubber. Inner shell 425, and outer shell 426 are bonded together with adhesive. Channels molded in inner shell 425 form fluid channels 421, and aspiration channel 423 once the inner shell 425, and outer shell 426 are bonded together. Inlet manifold 419 is in fluid communication with fluid channels 421. Aspiration manifold(s) 20 are in fluid communication with aspiration channel 423. Inlet manifold is connected to cooling fluid inlet tube 3 (FIG. 38) with tube fitting (not shown). Aspiration manifold(s) is connected to aspiration tube 404 (FIG. 38) with tube fitting (not shown). Fluid jets 422 are located incrementally along fluid channels 421 as shown. Aspiration ports 424 are located incrementally along aspiration channel 423 as shown. Cold saline enters inner liner 318 through inlet manifold under pressure as provided by console 402, and cooling fluid inlet tube 3 (FIG. 38). The cold saline is distributed through the walls of inner liner 418 by fluid channels 421. The cold saline exits fluid channels 421 through fluid jets 422 which direct the cold saline at the patient's head. Cooling jets 422 are holes through the wall of inner shell 425 and are sized such that the cold saline exits the fluid channel with sufficient velocity that the saline penetrates the patients hair, and reaches the patients scalp. Fluid jets are between 0.010 and 0.040 inches in diameter. The inner liner 418 contains between 25 and 150 fluid jets 422 which provides for even distribution of saline about the patient's head. Cold saline is provided to the inner liner 418 at a pressure of between 5 PSI and 50 PSI by the control console 42 (FIG. 38). Suction is applied to aspiration manifold(s) 420 by the console 402 and aspiration tube 404 (FIG. 38) which is in fluid communication with aspiration channel 423. Air and saline are drawn into aspiration channel 423 through aspiration ports 424 and is returned to console 402 through aspiration tube 404 (FIG. 38). The combination of suction, and the construction of aspiration channel 423 as shown when placed on a patient's head induces a pressure between the patient's head and inner liner 418 below atmospheric pressure thereby containing the saline under the inner liner 418.

Figure 40:
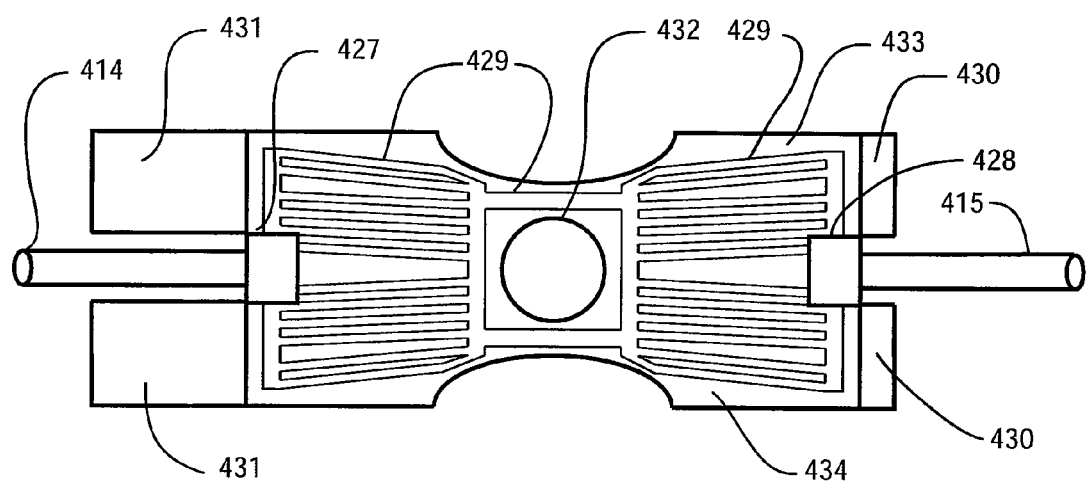
FIG. 40 illustrates a front view of the cooling collar of FIG. 38, according to one embodiment of the invention.
Figure 41:
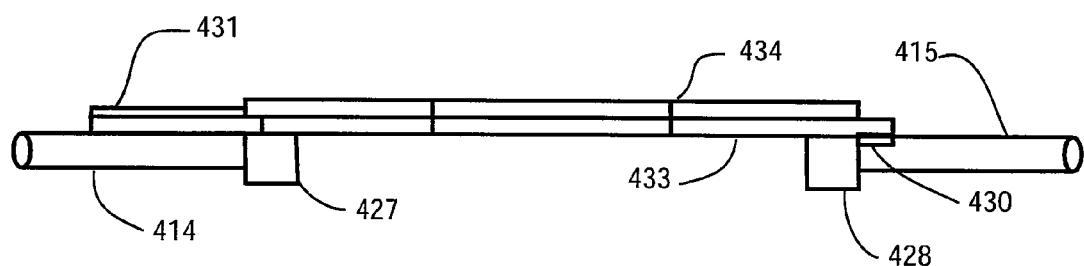
FIG. 41 illustrates a side view of the cooling collar of FIG. 38, according to one embodiment of the invention.

FIG. 40 depicts a front view of cooling collar 413. Cooling collar 413 consists of cooling fluid inlet tube 414, cooling fluid return tube 415, inlet manifold 427, outlet manifold 428, cooling channels 429 formed between inner layer 434 (opposite surface shown), and outer layer 433, Velcro® hook 430 (opposite surface shown), Velcro® loop 431, and tracheotomy hole 432. Cold saline is supplied to cooling collar 413 by console 402 (FIG. 38) under pressure through cooling fluid inlet tube 414. Cold saline enters cooling collar 413 through inlet manifold 427, then flows through multiple cooling channels 429 as shown, and exits cooling collar 413 through outlet manifold 428, and is returned to console 2 (FIG. 38) through cooling fluid return tube 15. Cooling collar 13 is wrapped around the patient's neck in a circular manner and fasted with Velcro Hook® 430, and Velcro® loop 431. Tracheotomy hole 432 is positioned over the patient's trachea to provide for emergency tracheotomy. Inner layer 434 is bonded to outer layer 433 by adhesive, or by a thermal bonding method depending on the material selected for the inner layer 434, and outer layer 433. Cooling channels are formed by masking, where there is no bond between inner layer 434, and outer layer 433. Inner layer 434 is formed from a sheet of polymer, or metal foil, or a lamination of polymer and metal foil. Inner layer 434 is between 0.001 and 0.008 inches thick. Outer layer 433 is formed from a sheet of polymer and is between 0.015 and 0.125 inches thick. Inlet manifold 427, and outlet manifold 428 are integrated into the cooling collar 413 during the bonding process (see FIG. 42). Velcro® hook 30, and Velcro® loop are bonded to cooling collar 413 with adhesive and thread. Cooling fluid inlet tube 414, and cooling fluid return tube 415 are made from vinyl tubing or a suitable equivalent and are 0.25 to 0.375 inches in diameter and have a wall thickness of 0.010 to 0.060. Fluid fittings (not shown) mounted on opposite ends of cooling fluid inlet tube 414, and cooling fluid return tube 415 provide removable connection to console 402 (FIG. 38). FIG. 41 depicts a side view of cooling collar 413. Cooling collar 413 is between 4 and 6 inches high, and has a length of between 12 and 20 inches to accommodate the circumference of a variety of patient's necks. The construction of the Velcro® fastening means 430 and 431 as shown provides for proper fit among various patients.

Figure 42:
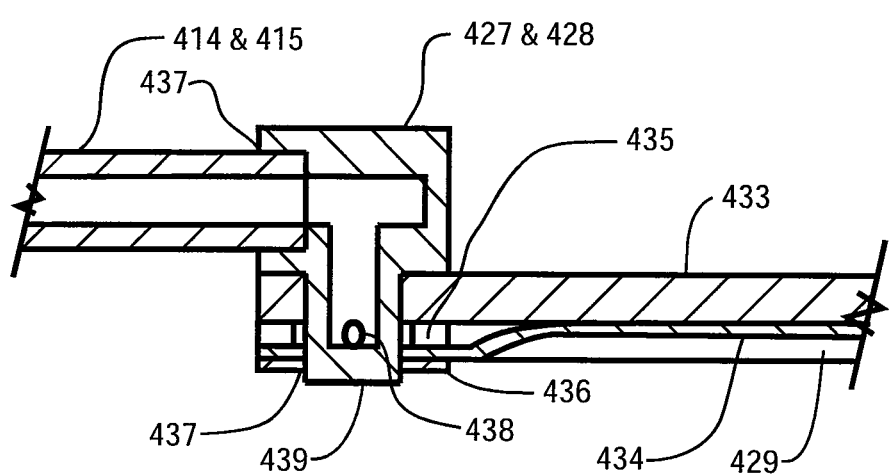
FIG. 42 illustrates a sectional view of the cooling collar of FIG. 38, according to one embodiment of the invention.

FIG. 42 depicts in sectional view the attachment of both the inlet manifold 427, and outlet manifold 428 to cooling collar 413. Cooling fluid inlet tube 414 is joined to inlet manifold 427 using adhesive 437, or a barbed tube fitting (not shown). Spacer 435 separates inner layer 434 from outer layer 433 about the circumference of manifold stem 439. Hole 438 is in radial alignment with a hole (not shown) in spacer 435. Inner liner 434 is sandwiched between spacer 435 and washer 436. The assembly is held together with adhesive 437, or is thermally bonded together. Cold saline flows from cooling fluid inlet tube 414 into inlet manifold 427, though hole 438, and through hole (not shown) in space 435 and into fluid channels 429.

What is claimed is:

1. A head-cooling device for inducing hypothermia comprising:
    a cap adapted to at least partially surround a patient's head and having at least one inner seal for sealing the cap against the patient's head to define a fluid circulation space into which a cooling fluid can be introduced to contact the patient's head;
    at least one inlet for introducing the cooling fluid into the fluid circulation space;
    at least one fluid outlet for withdrawing the cooling fluid from the fluid circulation space; and
    at least one vent comprising a check valve, to open the fluid circulation space to the atmosphere for introducing air into the fluid circulation space.

2. The head-cooling device of claim 1 wherein the inner seal further comprises at least one sealing member for sealing the fluid circulation space.

3. The head-cooling device of claim 1 wherein the inner seal further comprises an aspiration channel.

4. The head-cooling device of claim 3 wherein the aspiration channel cooperates with the at least one fluid outlet to remove fluid and/or air at a rate sufficient to inhibit leakage from the fluid circulation space.

5. The head-cooling device of claim 1 wherein the vent is configured to maintain the pressure within the fluid circulation space at substantially atmospheric pressure.

6. The head-cooling device of claim 1 wherein the cap further includes at least one rib or stud on an inner surface of the cap to maintain the fluid circulation space.

7. The head-cooling device of claim 1 further comprising a body-cooling device in fluid communication with the cap such that the cooling fluid can flow into and out of the body-cooling device, which body-cooling device optionally further comprises at least one heat transfer membrane configured to cover a body portion.

8. The head-cooling device of claim 7 wherein the body-cooling device further comprises a neck-cooling device.

9. The head-cooling device of claim 1 wherein the cap further comprises a flexible material.

10. The head-cooling device of claim 1 wherein the cap further comprises a substantially rigid shell.

11. The head-cooling device of claim 1 wherein the at least one inlet or the at least one fluid outlet or both further comprises a swivel joint configured to allow rotation of an inlet connector or outlet connector relative to the head-cooling device.

12. The head-cooling device of claim 1 wherein the device further comprises a fluid distribution manifold removably coupled to the at least one inlet of the head-cooling device, the fluid distribution manifold configured to distribute the cooling fluid from a fluid source within the fluid circulation space.

13. The head-cooling device of claim 1 wherein the at least one inlet further comprises at least one jet for creating fluid turbulence within the fluid circulation space.

14. The head-cooling device of claim 1 wherein the cap comprises at least one flow channel protrusion extending from an inner surface of the cap, the at least one flow channel protrusion configured to direct fluid flow within the fluid circulation space.

15. The head-cooling device of claim 1 wherein the cap comprises at least one head support disposed on an inner surface of the cap.

16. A cooling system for inducing hypothermia comprising: a head-cooling device having:
    a cap adapted to at least partially surround a patient's head and having at least one inner seal for sealing the cap against the patient's head to define a fluid circulation space into which a cooling fluid can be introduced to contact the patient's head;
    at least one inlet for introducing the cooling fluid into the fluid circulation space;
    at least one fluid outlet for withdrawing the cooling fluid from the fluid circulation space; and
    at least one vent comprising a check valve, to open the fluid circulation to the atmosphere for introducing air into the fluid circulation space; and
    a console having a fluid reservoir to hold a cooling fluid, and fluid conduits to couple the console and cooling device together for circulation of a cooling fluid therebetween.

17. The cooling system of claim 16 wherein the console further comprises at least one pump to deliver cooling fluid from the reservoir to the head-cooling device.

18. The cooling system of claim 16 wherein the console further comprises at least one negative pressure source to remove cooling fluid from the head-cooling device.

19. The head-cooling device of claim 1 wherein the at least one inlet, the at least one fluid outlet, and the at least one vent are each coupled to the cap at different locations around the cap.

20. The head-cooling device of claim 1 wherein the at least one ent substantially prevents the cooling fluid from exiting the fluid circulation space through the at least one vent.

21. The cooling system of claim 16 wherein the fluid reservoir and the head-cooling device form a closed loop fluid circulation system.

* * * * *